US008975070B2

(12) United States Patent
Sagawa et al.

(10) Patent No.: US 8,975,070 B2
(45) Date of Patent: *Mar. 10, 2015

(54) PROCESS FOR PRODUCING CYTOTOXIC LYMPHOCYTE

(71) Applicant: Takara Bio Inc., Otsu-shi (JP)

(72) Inventors: Hiroaki Sagawa, Kusatsu (JP); Mitsuko Ideno, Kyoto (JP); Ikunoshin Kato, Koka-gun (JP)

(73) Assignee: Takara Bio Inc., Otsu-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/250,227

(22) Filed: Apr. 10, 2014

(65) Prior Publication Data

US 2014/0212972 A1    Jul. 31, 2014

Related U.S. Application Data

(62) Division of application No. 10/509,055, filed as application No. PCT/JP03/03575 on Mar. 25, 2003, now Pat. No. 8,728,811.

(30) Foreign Application Priority Data

Mar. 25, 2002  (JP) .................................. 2002-84414

(51) Int. Cl.
| C12N 5/071 | (2010.01) |
| C12N 5/00 | (2006.01) |
| C12N 5/02 | (2006.01) |
| C12N 5/0783 | (2010.01) |
| A61K 35/12 | (2006.01) |

(52) U.S. Cl.
CPC ............ C12N 5/0638 (2013.01); C12N 5/0636 (2013.01); *A61K 2035/124* (2013.01); *C12N 2501/58* (2013.01); *C12N 2510/00* (2013.01)
USPC ....................................... 435/372.3; 435/377

(58) Field of Classification Search
None
See application file for complete search history.

(56) References Cited

U.S. PATENT DOCUMENTS

| 5,102,988 A | 4/1992 | Kimizuka et al. |
| 5,198,423 A | 3/1993 | Taguchi et al. |
| 5,354,686 A | 10/1994 | Haberman |
| 5,827,642 A | 10/1998 | Riddell et al. |
| 5,866,115 A | 2/1999 | Kanz et al. |
| 6,287,864 B1 | 9/2001 | Bagnis et al. |
| 6,316,257 B1 | 11/2001 | Flyer et al. |
| 6,472,204 B1 | 10/2002 | Asada et al. |
| 6,692,964 B1 | 2/2004 | June et al. |
| 6,734,014 B1 | 5/2004 | Hwu et al. |
| 6,821,778 B1 | 11/2004 | Engleman et al. |
| 7,067,318 B2 | 6/2006 | June et al. |
| 7,172,869 B2 | 2/2007 | June et al. |
| 2002/0119568 A1 | 8/2002 | Berenson et al. |
| 2003/0022210 A1 | 1/2003 | Bonyhadi et al. |
| 2004/0101519 A1 | 5/2004 | June et al. |
| 2004/0115809 A1 | 6/2004 | Sagawa et al. |
| 2005/0042208 A1 | 2/2005 | Sagawa et al. |
| 2005/0227354 A1 | 10/2005 | Sagawa et al. |
| 2006/0166924 A1 | 7/2006 | Kato et al. |
| 2006/0246587 A1 | 11/2006 | June et al. |
| 2008/0227204 A1 | 9/2008 | Sagawa et al. |

FOREIGN PATENT DOCUMENTS

| EP | 0 207 751 A1 | 1/1987 |
| EP | 0 409 655 A2 | 1/1991 |
| EP | 0 523 948 A2 | 1/1993 |
| EP | 0 795 606 A1 | 9/1997 |
| EP | 0 870 839 A1 | 10/1998 |
| EP | 1 424 387 A1 | 6/2004 |
| EP | 1 496 109 A1 | 1/2005 |
| EP | 1 666 589 A1 | 6/2006 |
| JP | 3-80076 A | 4/1991 |
| JP | 3-284700 A | 12/1991 |
| JP | 4-297494 A | 10/1992 |
| JP | 5-271291 A | 10/1993 |
| JP | 6-172203 A | 6/1994 |
| JP | 6-306096 A | 11/1994 |
| JP | 9-25299 A | 1/1997 |
| JP | 10-29952 A | 2/1998 |
| JP | 2729712 B2 | 3/1998 |
| JP | 11-505419 A | 5/1999 |
| JP | 3104178 B2 | 10/2000 |
| JP | 2001-314183 A | 11/2001 |
| JP | 2003-80817 A | 3/2003 |
| JP | 2004-500095 A | 1/2004 |
| WO | WO 88/02774 A1 | 4/1988 |
| WO | WO 89/01942 A1 | 3/1989 |
| WO | WO 90/13653 A1 | 11/1990 |
| WO | WO 95/04078 A1 | 2/1995 |

(Continued)

OTHER PUBLICATIONS

Animal Cell Culture: A Practical Approach, Edited by R. I. Freshney, IRL Press, Oxford, Washington, DC, 1986, pp. 26-41.
Animal Cell Culture: A Practical Approach, Edited by R. I. Freshney, IRL Press, Oxford, Washington, DC, 1989, pp. 44, 53, 77.
Animal Cell Culture: A Practical Approach, Freshney, Ed. 1986, IRL Press, Oxford, Washington, DC, Sections 2.1, 3.2.2-3.2.6, 5, 6.1-6.3, 3.1-3.4.
Aruga et al., "Enhancement of In Vitro Cytolytic Reactivity of T Cells Stimulated with Tumor-Pulsed Dendritic Cells", Biotherapy, vol. 12, No. 5, May 1998, pp. 875-877.
Avdalovic et al., "Adhesion and costimulation of proliferative responses of human $\gamma\delta$T cells by interaction of VLA-4 and VLA-5 with fibronectin", Immunology Letters, vol. 35, 1993, XP-002381602, pp. 101-108.
Azuma et al., "Functional Expression of B7/BB1 on Activated T Lymphocytes", J. Exp. Med., vol. 177, Mar. 1993, pp. 845-850.

(Continued)

Primary Examiner — Amy Juedes
(74) Attorney, Agent, or Firm — Birch, Stewart, Kolasch & Birch, LLP

(57) ABSTRACT

The present invention relates to a method for preparing a cytotoxic lymphocyte characterized in that the method comprises the step of carrying out at least one of induction, maintenance and expansion of a cytotoxic lymphocyte in the presence of fibronectin, a fragment thereof or a mixture thereof.

10 Claims, 1 Drawing Sheet

(56) References Cited

FOREIGN PATENT DOCUMENTS

| | | |
|---|---|---|
| WO | WO 95/11963 A1 | 5/1995 |
| WO | WO 95/28479 A1 | 10/1995 |
| WO | WO 96/00782 A1 | 1/1996 |
| WO | WO 96/06929 A2 | 3/1996 |
| WO | WO 96/16674 A1 | 6/1996 |
| WO | WO 97/01194 A1 | 1/1997 |
| WO | WO 97/05239 A1 | 2/1997 |
| WO | WO 97/11604 A1 | 4/1997 |
| WO | WO 97/11694 A1 | 4/1997 |
| WO | WO 97/18318 A1 | 5/1997 |
| WO | WO 97/32970 A1 | 9/1997 |
| WO | WO 98/12306 A1 | 3/1998 |
| WO | WO 98/33888 A1 | 8/1998 |
| WO | WO 99/05301 A1 | 2/1999 |
| WO | WO 99/33863 A1 | 7/1999 |
| WO | WO 99/33869 A2 | 7/1999 |
| WO | WO 00/09168 A1 | 2/2000 |
| WO | WO 00/56368 A1 | 9/2000 |
| WO | WO 01/62895 A2 | 8/2001 |
| WO | WO 02/14481 A1 | 2/2002 |
| WO | WO 03/016511 A1 | 2/2003 |
| WO | WO 03/080817 A1 | 10/2003 |
| WO | WO 2004/018667 A1 | 3/2004 |
| WO | WO 2005/019450 A1 | 3/2005 |

OTHER PUBLICATIONS

Bednarek et al., "The Minimum Peptide Epitope from the Influenza Virus Matrix Protein: Extra and Intracellular Loading of HLA-A2", The Journal of Immunology, vol. 147, No. 12, Dec. 15, 1991, pp. 4047-4053.
Benigni et al., "Phenotype and Homing of CD4 Tumor-Specific T Cells is Modulated by Tumor Bulk," The Journal of Immunology, vol. 175, 2005, pp. 739-748.
Blue et al. "Enhancement of CD2-Mediated T Cell Activation by the Interaction of VLA-4 with Fibronectin", Cellular Immunology, vol. 138, 1991, pp. 238-244.
Canadian Office Action, dated Feb. 28, 2012, for Application No. 2,479,288.
Cardarelli et al., "Fibronectin Augments Anti-CD3-Mediated IL-2 Receptor (CD25) Expression on Human Peripheral Blood Lymphocytes", Cellular Immunology, vol. 135, 1991, pp. 105-117.
Carter et al., "Development and maintenance of bovine cytotoxic lymphocytes with recombinant human interleukin-2", Immunology, vol. 57, 1986, pp. 123-129.
Chen et al., "Retroviral Transduction of Protein Kinase C-γ into Tumor-Specific T Cells Allows Antigen-Independent Long-Term Growth in IL-2 with Retention of Functional Specificity in Vitro and Ability to Mediate Tumor Therapy in Vivo", J. Immunol., vol. 153, 1994, pp. 3630-3638.
Chinese Office Action, dated Jan. 15, 2010, for Chinese Application No. 200480024172.7, with an English translation.
Chinese Office Action, dated Nov. 30, 2007, for Chinese Application No. 200480024172.7 with an English translation.
Dardalhon et al., "Highly efficient gene transfer in naive human T cells with a murine leukemia virus-based vector," Blood, vol. 96, No. 3, Aug. 1, 2000, pp. 885-893.
Davis et al., "Fibronectin Promotes Proliferation of Naive and Memory T Cells by Signaling Through both the VLA-4 and VLA-5 Integrin Molecules", The Journal of Immunology, vol. 145, No. 3, Aug. 1, 1990, pp. 785-793.
Del Pozo et al., "Chemokines Regulate Cellular Polarization and Adhesion Receptor Redistribution During Lymphocyte Interaction with Endothelium and Extracellular Matrix, Involvement of cAMP Signaling Pathway", The Journal of Cell Biology, vol. 131, No. 2, Oct. 1995, pp. 495-508.
European Search Report, dated Dec. 8, 2009, for European Application No. 09004189.8.
Funaro et al., "Stimulation of T Cells via CD44 Requires Leukocyte-Function-Associated Antigen Interactions and Interleukin-2 Production", Human Immunology, vol. 40, No. 4, Aug. 1994, pp. 267-278.
Galandrini et al., "Antibodies to CD44 Trigger Effector Functions of Human T Cell Clones", The Journal of Immunology, vol. 150, No. 10, May 15, 1993, pp. 4225-4235.
Galandrini et al., "CD44 Triggering Enhances Human NK Cell Cytotoxic Functions", Journal of Immunology, vol. 153, No. 10, Nov. 15, 1994, pp. 4399-4407 (abstract only).
Galandrini et al., "Hyaluronate is Costimulatory for Human T Cell Effector Functions and Binds to CD44 on Activated T Cells", The Journal of Immunology, vol. 153, 1994, pp. 21-31.
Galandrini et al., "Ligation of the Lymphocyte Homing Receptor CD44 Triggers T-Helper and Cytolytic Functions of Human T-Cells", Cytotechnology, vol. 11, Suppl. 1, 1993, pp. S100-102 (abstract only).
Gallagher et al., "Interleukin-3 and interleukin-4 each strongly inhibit the induction and function of human LAK cells", Clin. exp. Immunol., vol. 74, 1988, pp. 166-170.
Gattinoni et al., "Acquisition of full effector function in vitro paradoxically impairs the in vivo antitumor efficacy of adoptively transferred CD8+ T cells," J. Clin. Invest., vol. 115, No. 6, Jun. 2005, pp. 1616-1626.
Genetic Medicine, vol. 3, No. 2, 1999, pp. 114-119 (with a partial English translation).
GIBCO/Invitrogen Publication, "A Guide to Serum-Free Cell Culture", 2003, 7 pages.
Greenberg, "Adoptive T Cell Therapy of Tumors: Mechanisms Operative in the Recognition and Elimination of Tumor Cells", Advances in Immunology, vol. 49, 1991, pp. 281-355.
Halvorson et al., "α4 and α5 Integrins Costimulate the CD3-dependent Proliferation of Fetal Thymocytes," Cell. Immunol., vol. 189, Article No. CI981368, 1998, pp. 1-9.
Hanenberg et al., "Optimization of Fibronectin-Assisted Retroviral Gene Transfer into Human CD34+ Hematopoietic Cells", Human Gene Therapy, vol. 8, No. 2, Dec. 10, 1997, pp. 2193-2206.
Hibino et al., "Tenascin Suppresses CD3-Mediated T Cell Activation", Biochemical and Biophysical Research Communications, vol. 250, Article No. RC989258, 1998, pp. 119-124.
Ho et al., "A Phase 1 Study of Adoptive Transfer of Autologous CD8+ T Lymphocytes in Patients With Acquired Immunodeficiency Syndrome (AIDS)-Related Complex or AIDS", Blood, vol. 81, No. 8, Apr. 15, 1993, pp. 2093-2101.
Ideno et al., "Novel expansion methods of CTL using recombinant fibronectin fragments," Dai 62 Kai Annual Meeting of the Japan Cancer Association Kiji, Sep. 25-27, 2003, pp. 175.
Ideno et al., "T cell expansion using RetroNectin(II): RN-T cells contain high portion of Naive T-like cells and show high ability of antigen recognition (p. 708)," 2006, pp. 330.
International Preliminary Report on Patentability (Forms PCT/IB/373), dated Apr. 1, 2008 and Written Opinion of the International Searching Authority, dated Jan. 9, 2007, for International Application No. PCT/JP2006/319105 (Form PCT/ISA/237).
International Preliminary Report on Patentability (Forms PCT/IB/373), dated Feb. 20, 2008, and Written Opinion of the International Searching Authority, dated Oct. 10, 2010, for International Application No. PCT/JP2006/315881 (Form PCT/ISA/210).
International Search Report (Form PCT/ISA/210), dated Nov. 27, 2001, for International Application No. PCT/JP01/07032.
International Search Report, dated Dec. 3, 2002, for International Application No. PCT/JP02/08298.
Janeway et al., "Immuno Biology: The Immune System in Health and Disease", Third Edition, 1997, p. 4:2.
Japanese Office Action, dated Mar. 5, 2010, for Japanese Application No. 2005-513357.
Japanese Office Action, dated Nov. 14, 2011, for Japanese Application No. 2007-530976 with an English translation.
Johnson et al, "Expression and Function of Insulin-Like Growth Factor Receptors on Anti-CD3-Activated Human T Lymphyocytes", The Journal of Immunology, vol. 148, No. 1, Jan. 1, 1992, pp. 63-71.
Johnston et al., "Induction of B16 Melanoma Melanogenesis by a Serum-Free Synthetic Medium," Experimental Cell Research, vol. 201, 1992, pp. 91-98.
Jung et al., "Induction of Cytotoxicity in Human Peripheral Blood Mononuclear Cells by Monoclonal Antibody OKT3", The Journal of Immunology, vol. 139, No. 2, Jul. 15, 1987, pp. 639-644.

(56) References Cited

OTHER PUBLICATIONS

Kaldjian et al., "Enhancement of lymphocyte proliferation assays by use of serum-free medium", Journal of Immunological Methods, vol. 147, No. 2, 1992, pp. 189-195.

Kanto et at, "Neutralization of Transforming Growth Factor β-1 Augments Hepatitis C Virus-Specific Cytotoxic T Lymphocyte Induction In Vitro", Journal of Clinical Immunology, vol. 17, No. 6, 1997, pp. 462-471.

Kato et al., "Kaisou shokumotsu sen-i ni yoru gan risk keigen", Jpn. J. Phycol., vol. 48, Mar. 10, 2000, pp. 13-19, with an English abstract.

Katzman et al., "Fibronectin and cellular cytotoxicity: Evidence against a role for fibronectin in natural killer activity", J Lab Clin Med, vol. 110, No. 1, Jul. 1987, pp. 75-82.

Kim et al., "4-1BB Costimulation Promotes Human T Cell Adhesion to Fibronectin", Cellular Immunology, vol. 192, pp. 13-23, 1999.

Kimizuka et al., "Production and Characterization of Functional Domains of Human Fibronectin Expressed in *Escherichia coli*", J. Biochem., vol. 110, No. 2, 1991, pp. 284-291.

Koberda et al., "Effect of anti-CD3/anti-CD28/interleukin-2 stimulation of mononuclear cells on transforming growth factor β inhibition of lymphokine-activated killer cell generation," J. Cancer Res. Clin. Oncol., vol. 119, 1993, pp. 131-136.

Kornblihtt et al., "Isolation and characterization of cDNA clones for human and bovine fibronectins", Proc. Natl. Acad. Sci., vol. 80, Jun. 1983, pp. 3218-3222.

Kornblihtt et al., "Primary structure of human fibronectin: differential splicing may generate at least 10 polypeptides from a single gene", The EMBO Journal, vol. 4, No. 7, 1985, pp. 1755-1759.

Kornblihtt et al., "The fibronectin gene as a model for splicing and transcription studies," The FASSEB Journal, vol. 10, Feb. 1996, pp. 248-257.

Lamers et al., "Protocol for Gene Transduction and Expansion of Human T Lymphocytes for Clinical Immunogene Therapy of Cancer", Cancer Gene Therapy, vol. 9, 2002, pp. 613-623.

Lehnert et al., "MAdCAM-1 costimulates T cell proliferation exclusively through integrin α4β7, whereas VCAM-1 and CS-1 peptide use α4β1: evidence for "remote" costimulation and induction of hyperresponsiveness to B7 molecules", Eur. J. Immunol., vol. 28, 1998, pp. 3605-3615.

Li et al., "Enhancement of Lymphokine-Activated Killer Cell Activity by Fibronectin," Journal of Immunotherapy, vol. 20, No. 2, 1997, pp. 123-130.

Lucivero et al., "Functional Characteristics of Cord Blood T Lymphocytes After Lectin and Anti-CD3 Stimulation", Int. J. Clin. Lab. Res., vol. 26, 1996, pp. 255-261.

Matsuyama et al., "Activation of CD4 Cells by Fibronectin and Anti-CD3 Antibody: A Synergistic Effect Mediated by the VLA-5 Fibronectin Receptor Complex," The Journal of Experimental Medicine, vol. 170, No. 4, Oct. 1989, pp. 1133-1148.

Mazumder et al., "Phase I Study of the Adoptive Immunotherapy of Human Cancer with Lectin Activated Autologous Mononuclear Cells", Cancer, vol. 53, No. 4, Feb. 1984, pp. 896-905.

Mikamo, "Bulk Culture of Human Lymphocytes", Cell Technology, vol. 14, No. 2, 1995, pp. 223-227.

Mizobata et al., "Fibronectin promotes the proliferation of cytotoxic T lymphocytes generated from cancer patients", British Journal of Cancer, vol. 74, 1996, XP008058177, pp. 1598-1604.

Mizobata et al., "Study of fibronectin on the proliferation and the activation of cytotoxic T lymphocytes generated by immobilized anti-CD 3 monoclonal antibody and interleukin-2", J. Wakayama Med. Soc., vol. 46, No. 4, 1995, pp. 457-467 (with an English abstract).

Muraki et al., "T cell expansion using RetroNectin (I): Useful method to expand T cells, characterized by high portion of Naive T-like cells," Dai 65 Kai Annual Meeting of the Japan Cancer Association Kiji, Aug. 28, 2006, pp. 330.

Neri et al., "Calcein-Acetyoxymethyl Cytotoxicity Assay: Standardization of a Method Allowing Additional Analyses on Recovered Effector Cells and Supernatants", Clinical and Diagnostic Laboratory Immunology, vol. 8, No. 6, Nov. 2001, pp. 1131-1135.

Noguchi et al., "Polysaccharide Preparation PSK Augments the Proliferation and Cytotoxicity of Tumor-Infiltrating Lymphocytes in Vitro", Anticancer Research, vol. 15, 1995, pp. 255-258.

Nunclon*(Delta) MicroWell* Plates, Sterile, VWR LabShop, http://vwrlabshop.com/product.asp, retrieved Apr. 19, 2007, 1 page.

Ochoa et al., "Long-Term Growth of Lymphokine-Activated Killer (LAK) Cells: Role of Anti-CD3, β-IL 1, Interferon-γ and -β¹", The Journal of Immunology, vol. 138, No. 8, Apr. 15, 1987, pp. 2728-2733.

Ochoa et al., "Lymphokine-Activated Killer Activity in Long-Term Cultures with Anti-CD3 Plus Interleukin 2: Identification and Isolation of Effector Subsets", Cancer Research, vol. 49, Feb. 15, 1989, pp. 963-968.

Ostergaard et al., "Fibronectin Induces Phosphorylation of a 120-kDa Protein and Synergizes with the T Cell Receptor to Activate Cytotoxic T Cell Clones", Eur. J. Immunol., vol. 25, 1995, pp. 252-256.

Palmieri et al., "Cross-Linking of α4β1 and α5β1 Fibronectin Receptors Enhances Natural Killer Cell Cytotoxic Activity", The Journal of Immunology, vol. 155, 1995, XP-002381601, pp. 5314-5322.

Parhar et al., "Anti-tumor cytotoxic potential and effect on human bone marrow GM-CFU of human LAK cells generated in response to various cytokines", Eur. Cytokine Netw., vol. 3, No. 3, May-Jun. 1992, pp. 299-306.

Parker et al., "Expansion and Characterization of T Cells Transduced with a Chimeric Receptor against Ovarian Cancer," Human Gene Therapy, vol. 11, Nov. 20, 2000, pp. 2377-2387.

Partial European Search Report, dated Aug. 3, 2009, for European Application No. 09004189.8.

Paul et al., "Long-term growth and cloning of non-transformed lymphocytes", Nature, vol. 294, Dec. 1981, pp. 697-699.

Pawelec et al., "Extrathymic T cell differentiation in vitro from human CD34+ stem cells", Journal of Leukocyte Biology, vol. 64, Dec. 1998, pp. 733-739.

Petersen et al., "Primary Structure of Fibronectin", Fibronectin, Academic Press, Inc., 1989. pp. 1-24.

Pierschbacher et al., "Location of the Cell-Attachment Site in Fibronectin with Monoclonal Antibodies and Proteolytic Fragments of the Molecule", Cell, vol. 26, Part 2, Oct. 1981, XP-002381682, pp. 259-267.

Pollok et al., "High-Efficiency Gene Transfer into Normal and Adenosine Deaminase-Deficient T Lymphocytes Is Mediated by Transduction on Recombinant Fibronectin Fragments", Journal of Virology, vol. 72, No. 6, Jun. 1998, pp. 4882-4892.

Rao et al., "Potent Costimulation of Effector T Lymphocytes by Human Collagen Type I", The Journal of Immunology, vol. 165, 2000, pp. 4935-4940.

Retronectin, Cat. #T100A/B, v1009, 2010, Takara Bio. Inc., http://catalog.takara-bio.co.jp/en/PDFFiles/T100A_B_e.pdf, www.takara-bio.com, p. 1-8.

Reusser et al., "Cytotoxic T-Lymphocyte Response to Cytomegalovirus After Human Allogeneic Bone Marrow Transplantation: Pattern of Recovery and Correlation With Cytomegalovirus Infection and Disease", Blood, vol. 78, No. 5, Sep. 1, 1991, pp. 1373-1380.

Riddell et al., "Class I MHC-Restricted Cytotoxic T Lymphocyte Recognition of Cells Infected with Human Cytomegalovirus does not Require Endogenous Viral Gene Expression", The Journal of Immunology, vol. 146, No. 8, Apr. 15, 1991, pp. 2795-2804.

Riddell et al., "Restoration of Viral Immunity in Immunodeficient Humans by the Adoptive Transfer of T Cell Clones", Science, vol. 257, Jul. 10, 1992, pp. 238-241.

Riddell et al., "The use of anti-CD3 and anti-CD28 monoclonal antibodies to clone and expand human antigen-specific T cells", Journal of Immunological Methods, vol. 128, 1990, pp. 189-201.

Rider et al., "Phorbol Diesters and Dioctanoylglycerol Stimulate Accumulation of Both Diacylglycerols and Alkylacylglycerols in Human Neutrophils", The Journal of Immunology, vol. 140, No. 1, Jan. 1, 1988, pp. 200-207.

Rosenberg et al., "A progress report on the treatment of 157 patients with advanced cancer using lymphokine-activated killer cells and interleukin-2 or high-dose interleukin-2 alone", The New England Journal of Medicine, vol. 316, No. 15, Apr. 9, 1987, pp. 889-897.

(56) References Cited

OTHER PUBLICATIONS

Rosenberg et al., "Use of Tumor-Infiltrating Lymphocytes and Interleukin-2 in the Immunotherapy of Patients with Metastatic Melanoma", The New England Journal of Medicine, vol. 319, No. 25, Dec. 22, 1988, pp. 1676-1680.
Rostagno et al., "Comparison of the fibrin-binding activities in the N- and C-termini of fibronectin", Biochem. J., vol. 338, 1999, pp. 375-386.
Ruoslahti et al., "Alignment of Biologically Active Domains in the Fibronectin Molecule", The Journal of Biological Chemistry, vol. 256, No. 14, Jul. 25, 1981, pp. 7277-7281.
Sagawa et al., "Improvement of LAK cells expansion method with combined use of RetroNectin and anti-CD3 antibody," Dai 62 Kai Annual Meeting of the Japan Cancer Association Kiji, 2003, p. 438, with English abstract.
Sekiguchi et al., "Human Liver Fibronectin Complementary DNAs: Identification of Two Different Messenger RNAs Possibly Encoding the $\alpha$ and $\beta$ Subunits of Plasma Fibronectin", Biochemistry, vol. 25, 1986, pp. 4936-4941.
Sekine, "Expansion of Lymphocytes by Culture with Immobilized Anti-CD3 Monoclonal Antibody and Interleukin-2 for Use in Adoptive Immunotherapy of Cancer Patients", Saibo Baiyo (Cell Culture), vol. 17, No. 6, 1991, pp. 192-195, with English abstract.
Seth et al., "T-Cell-Receptor-Independent Activation of Cytolytic Activity of Cytotoxic T Lymphocytes Mediated Through CD44 and gp90MEL-14", Proc. Natl. Acad. Sci. U.S.A., vol. 88, No. 17, Sep. 1991, pp. 7877-7881.
Shimizu et al., "Costimulation of Proliferative Responses of Resting CD4+ T Cells by the Interaction of VLA-4 and VLA-5 with Fibronectin or VLA-6 with Laminin[1]", The Journal of Immunology, vol. 145, No. 1, Jul. 1, 1990, XP-002362286, pp. 59-67.
Shun et al., "An experimental study on immunoregulatory effect of fucoidan", Zhongguo Haiyang Yaowu, vol. 14, No. 3, 1995, pp. 9-13 (with an English abstract).
Shuqin et al., "Induction of Allogeneic Cytotoxic T Lymphocytes and Their Culture", Journal of South China Normal University, No. 4, 1994, pp. 11-17 (abstract only provided).
Sigma-Aldrich D5156 Product sheet for "1,2-Dioctanoyl-sn-glycerol", 2 pages, downloaded on Mar. 8, 2011 from http://www.sigmaaldrich.com/catalog/ProductDetail.do?D7=0&N5=SEARCH_CONCAT_PNO%7CBRAND_KEY&N4=D5156%7CSIGMA&N25=0&QS=ON&F=SPEC.
Simon et al., "The outer surface lipoprotein A of Borrelia burgdorferi provides direct and indirect augmenting/co-stimulatory signals for the activation of CD4+ and CD8+ T cells", Immunology Letters, vol. 45, No. 3, 1995, pp. 137-142.
Stohl et al., "Generation of Cytolytic Activity with Anti-CD3 Monoclonal Antibodies Involves both IL-2-Independent and -Dependent Components", The Journal of Immunology, vol. 144, No. 10, May 15, 1990, pp. 3718-3725.
Sturm et al., "Dual Function of the Extracellular Matrix: Stimulatory for Cell Cycle Progression of Naive T Cells and Antiapoptotic for Tissue-Derived Memory T Cells", The Journal of Immunology, vol. 173, 2004, pp. 3889-3900.
Supplementary European Search Report issued in European Application No. 06782667.7 on Sep. 16, 2009.
Takahashi et al., "Antigen-independent T-cell activation mediated by a very late activation antigen-like extracellular matrix receptor", Eur. J. Immunol., vol. 21, 1991, pp. 1559-1562.
Takayama et al., "Adoptive immunotherapy to lower postsurgical recurrence rates of hepatocellular carcinoma: a randomised trial", The Lancet, vol. 356, Sep. 2, 2000, pp. 802-807.
Tamura et al., "Expression and Function of c-Met, a Receptor for Hepatocyte Growth Factor, During T-Cell Development", Scandinavian Journal of Immunology, vol. 47, 1998, pp. 296-301.
Tani et al., "Gan tokuiteki men'eki ryoho-CTL ryoho no genjo to shorai", Cancer Therapy & Host, vol. 12, No. 4, Oct. 2000, pp. 330-335.
U.S. Communication, dated Aug. 31, 2010, for U.S. Appl. No. 11/990,443.
U.S. Interview Summary, dated Aug. 2, 2007, for U.S. Appl. No. 10/486,512.
U.S. Interview Summary, dated Jun. 4, 2008, for U.S. Appl. No. 10/344,534.
U.S. Interview Summary, dated Jun. 7, 2010, for U.S. Appl. No. 11/831,423.
U.S. Interview Summary, dated Mar. 19, 2007, for U.S. Appl. No. 10/344,534.
U.S. Interview Summary, Feb. 5, 2008, for U.S. Appl. No. 10/344,534.
U.S. Notice of Allowance, dated Jun. 16, 2010, for U.S. Appl. No. 10/344,534.
U.S. Notice of Allowance, dated Oct. 29, 2010, for U.S. Appl. No. 10/486,512.
U.S. Office Action dated Jul. 12, 2010, for U.S. Appl. No. 10/568,745.
U.S. Office Action, dated Apr. 19, 2010, for U.S. Appl. No. 10/486,512.
U.S. Office Action, dated Apr. 2, 2010, for U.S. Appl. No. 11/790,025.
U.S. Office Action, dated Apr. 24, 2006, for U.S. Appl. No. 10/486,512.
U.S. Office Action, dated Dec. 18, 2009, for U.S. Appl. No. 11/790,025.
U.S. Office Action, dated Dec. 19, 2013, for U.S. Appl. No. 10/568,745.
U.S. Office Action, dated Dec. 28, 2010, for U.S. Appl. No. 11/992,661.
U.S. Office Action, dated Feb. 23, 2007, for U.S. Appl. No. 10/486,512.
U.S. Office Action, dated Jan. 18, 2008, for U.S. Appl. No. 10/344,534.
U.S. Office Action, dated Jan. 5, 2009, for U.S. Appl. No. 10/486,512.
U.S. Office Action, dated Jan. 5, 2009, for U.S. Appl. No. 11/790,025.
U.S. Office Action, dated Jul. 12, 2010, for U.S. Appl. No. 11/990,443.
U.S. Office Action, dated Jul. 12, 2013, for U.S. Appl. No. 11/992,661.
U.S. Office Action, dated Jul. 23, 2009, for U.S. Appl. No. 10/344,534.
U.S. Office Action, dated Jul. 25, 2006, for U.S. Appl. No. 10/486,512.
U.S. Office Action, dated Jul. 26, 2010, for U.S. Appl. No. 10/344,534.
U.S. Office Action, dated Jul. 9, 2009, for U.S. Appl. No. 10/568,745.
U.S. Office Action, dated Jun. 18, 2009, for U.S. Appl. No. 10/344,534.
U.S. Office Action, dated Jun. 20, 2005, for U.S. Appl. No. 10/344,534.
U.S. Office Action, dated Jun. 23, 2009, for U.S. Appl. No. 10/486,512.
U.S. Office Action, dated Jun. 9, 2011, for U.S. Appl. No. 11/992,661.
U.S. Office Action, dated Mar. 16, 2011, for U.S. Appl. No. 11/990,443.
U.S. Office Action, dated Mar. 18, 2010, for U.S. Appl. No. 11/831,423.
U.S. Office Action, dated Mar. 18, 2011, for U.S. Appl. No. 10/568,745.
U.S. Office Action, dated Mar. 28, 2006, for U.S. Appl. No. 10/344,534.
U.S. Office Action, dated Mar. 5, 2009, for U.S. Appl. No. 11/831,423.
U.S. Office Action, dated May 13, 2008, for U.S. Appl. No. 10/344,534.
U.S. Office Action, dated May 16, 2007, for U.S. Appl. No. 10/344,534.
U.S. Office Action, dated May 27, 2009, for U.S. Appl. No. 11/831,423.
U.S. Office Action, dated May 28, 2010, for U.S. Appl. No. 10/344,534.
U.S. Office Action, dated May 30, 2008 for U.S. Appl. No. 10/486,512.

(56) References Cited

OTHER PUBLICATIONS

U.S. Office Action, dated May 7, 2009, for U.S. Appl. No. 11/790,025.
U.S. Office Action, dated Nov. 22, 2010, for U.S. Appl. No. 10/486,512.
U.S. Office Action, dated Nov. 24, 2009, for U.S. Appl. No. 10/344,534.
U.S. Office Action, dated Nov. 27, 2009, for U.S. Appl. No. 10/568,745.
U.S. Office Action, dated Nov. 4, 2009, for U.S. Appl. No. 11/831,423.
U.S. Office Action, dated Nov. 6, 2009, for U.S. Appl. No. 10/344,534.
U.S. Office Action, dated Oct. 10, 2007, for U.S. Appl. No. 10/486,512.
U.S. Office Action, dated Oct. 11, 2005, for U.S. Appl. No. 10/344,534.
U.S. Office Action, dated Oct. 14, 2010, for U.S. Appl. No. 11/992,661.
U.S. Office Action, dated Oct. 25, 2010, for U.S. Appl. No. 10/568,745.
U.S. Office Action, dated Sep. 24, 2007, for U.S. Appl. No. 10/344,534.
U.S. Office Action, dated Sep. 25, 2006, for U.S. Appl. No. 10/344,534.
U.S. Office Action, dated Sep. 30, 2009, for U.S. Appl. No. 10/486,512.
U.S. Office Office Action, dated Jul. 8, 2011, for U.S. Appl. No. 11/990,443.
Uberti et al., "Preclinical Studies Using Immobilized OKT3 to Activate Human T Cells for Adoptive Immunotherapy: Optimal Conditions for the Proliferation and Induction of Non-MHC-Restricted Cytotoxicity", Clinical Immunology and Immunopathology, vol. 70, No. 3, Mar. 1994, pp. 234-240.
Van Der Loo et al., "VLA-5 is Expressed by Mouse and Human Long-Term Repopulating Hematopoietic Cells and Mediates Adhesion to Extracellular Matrix Protein Fibronectin", J. Clin. Invest., vol. 102, No. 5, Sep. 1998, pp. 1051-1061.
Whiteside et al., "Isolation of Human NK Cells and Generation of LAK Activity", Current Protocols in Immunology, Supp. 17, Unit 7.7, 1996, 11 pages.
Williams et al., "Fibronectin and VLA-4 in haematopoietic stem cell-microenvironment interactions," Nature, vol. 352, Aug. 1, 1991, pp. 438-441.
Wills, et al, "Identification of Naive or Antigen-Experienced Human CD8+ T Cells by Expression of Costimulation and Chemokine Receptors: Analysis of the Human Cytomegalovirus-Specific CD8+ T Cell Response", The Journal of Immunology, vol. 168, 2002, pp. 5455-5464.
Wolf et al., "Leukapheresis for the extraction of monocytes and various lymphocyte subpopulations from peripheral blood: product quality and prediction of the yield using different harvest procedures", Vox Sanguinis, vol. 88, 2005, pp. 249-255.
Ybarrondo et al., "Cytotoxic T-lymphocyte interaction with fibronectin and vitronectin: activated adhesion and cosignalling", Immunology, vol. 91, 1997, pp. 186-192.
Yoneda et al., "Role of the Heparin-Binding Domain of Chimeric Peptides Derived from Fibronectin in Cell Spreading and Motility", Experimental Cell Research, vol. 217, 1995, pp. 169-179.
Yu et al., "The Study of Human LAK and LI-LAK Cells' Proliferation and Activation of Antitumor in Vitro", Journal of Jinan University (Natural Science & Medicine Edition), vol. 19 Suppl., Dec. 1998, pp. 56-60, with English abstract.
Zhou et al., "Molecular Mechanisms Underlying Differential Contribution of CD28 Versus Non-CD28 Costimulatory Molecules to IL-2 Promoter Activation," The Journal of Immunology, vol. 168, 2002, pp. 3847-3854.

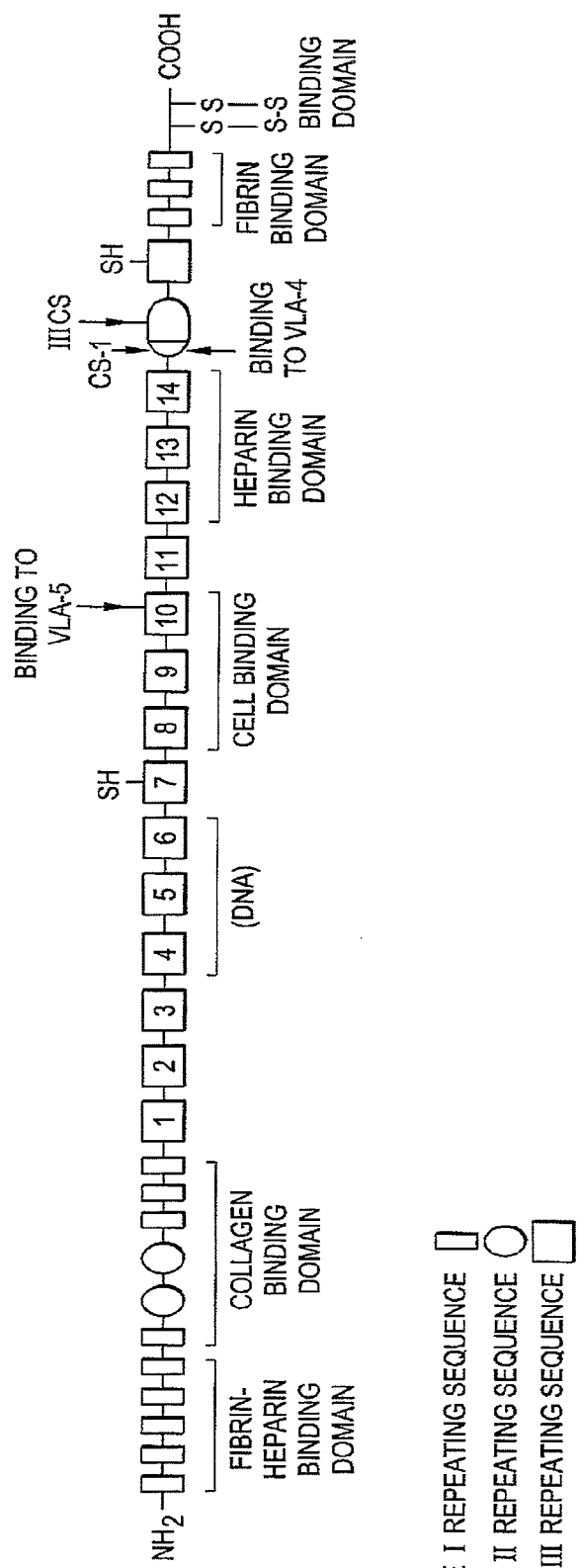

PROCESS FOR PRODUCING CYTOTOXIC LYMPHOCYTE

This application is a Divisional of co-pending U.S. application Ser. No. 10/509,055 filed on Sep. 24, 2004 and for which priority is claimed under 35 U.S.C. §120. U.S. application Ser. No. 10/509,055 is the national phase of PCT International Application No. PCT/JP03/03575 filed on Mar. 25, 2003 under 35 U.S.C. §371. U.S. application Ser. No. 10/509,055 also claims the benefit of priority of 2002-84414 under 35 U.S.C. §119, which was filed in Japan on Mar. 25, 2002. The entire contents of each of the above-identified applications are hereby incorporated by reference.

TECHNICAL FIELD

The present invention relates to a method for preparing a cytotoxic lymphocyte, which is useful in the medical field.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (which may be hereinafter referred to as B cell) and T lymphocyte (which may be hereinafter referred to as T cell), both of which specifically recognize an antigen and act on the antigen to protect the living body.

T cell is subclassified to helper T cell having CD(Cluster Designation)4 marker (hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like in B cell, but directly recognizes and acts on antigens (antigenic peptide) from a target cell which is associated with major histocompatibility complex [MHC, which may be also referred to as human leukocyte antigen (HLA) in human] Class I molecules existing on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is derived from itself or nonself. Target cell which has been determined to be from nonself is then specifically destroyed and eliminated by CTL.

Recent years, a therapy which would cause a heavier physical burden on a patient, such as pharmacotherapy and radiotherapy, has been reconsidered, and an interest has increased in an immunotherapy with a lighter physical burden on a patient. Especially, there has been remarked an effectiveness of adoptive immunotherapy in which CTL capable of specifically reacting with an antigen of interest is induced in vitro from lymphocyte derived from a human having normal immune function, or the lymphocyte is expanded without induction, and then transferred to a patient. For instance, it has been suggested that in an animal model adoptive immunotherapy is an effective therapy for virus infection and tumor [authored by Greenberg, P. D., *Advances in Immunology*, published in 1992; Reusser P., et al., *Blood*, 78(5), 1373-1380 (1991)]. In this therapy, it is important to maintain or increase the cell number in a state in which the antigen-specific cytotoxic activity of the CTL is maintained or enhanced.

In the adoptive immunotherapy as described above, it is necessary to administer cytotoxic lymphocytes in the number of cells of a given amount or higher in order to obtain a therapeutic effect. In other words, it can be said that it is a major problem to obtain the above number of cells in vitro in a short period of time.

In order to maintain and enhance an antigen-specific cytotoxic activity of CTL, there has been generally employed a method of repeating stimulation with an antigen of interest when a specific response to an antigen for CTL is induced. However, in this method, the number of CTL finally obtained may usually be decreased, so that a sufficient number of cells cannot be obtained.

As a method for preparing T cell which is effective for the treatment of a disease, there has been known, for instance, adoptive immunotherapy using tumor-infiltrating lymphocyte (TIL) induced with IL-2 in a high concentration [*N. Engl. J. Med.*, 316, 1310-1321 (1986); Rosenberg S. A. et al, *N. Engl. J. Med.*, 319(25), 1676-1680 (1988); Ho M. et al., *Blood*, 81(8), 2093-2101 (1993)].

Next, regarding the preparation of the antigen-specific CTL, there has been reported a method for isolating and expanding a CMV-specific CTL clone using self-CMV infected fibroblast and IL-2 [Riddell S. A. et al., *J. Immunol.*, 146(8), 2795-2804 (1991)] or using anti-CD3 monoclonal antibody (anti-CD3 mAb) and IL-2 [Riddell S. A. et al., *J. Immunol. Methods*, 128(2), 189-201 (1990)].

Furthermore, WO 96/06929 discloses an REM method (rapid expansion method). This REM method is a method for expanding a primary T cell population containing antigen-specific CTL and $T_H$ in a short period of time. In other words, this method is characterized in that a large amount of T cell can be provided by proliferating individual T cell clones, and that the number of antigen-specific CTL is increased using an anti-CD3 antibody, IL-2, and PBMC (peripheral blood mononuclear cell) made deficient in an ability for proliferation by irradiation, and Epstein-Barr virus (hereinafter simply referred to as EBV)-infected cells.

In addition, WO 97/32970 discloses a modified REM method, wherein the method is a method using as a feeder cell an undifferentiated mammal cell strain expressing a T-cell stimulating component which is distinguishable from PBMC to reduce an amount of PBMC used.

The lymphokine-activated killer cell (LAK cell) is a functional cell population having an cytotoxic activity, which is obtained by adding IL-2 to peripheral blood (peripheral blood leukocyte), umbilical cord blood, tissue fluid or the like containing lymphocytes, and culturing the cells in vitro for several days. During the culture, proliferation of the LAK cell is further accelerated by adding an anti-CD3 antibody thereto and culturing the cell. The LAK cell thus obtained has a cytotoxic activity non-specifically to various cancer cells and other targets. The LAK cell is also used in the adoptive immunotherapy in the same manner as the above-mentioned CTL.

As described above, utilization of IL-2 is essential in the step of obtaining a cytotoxic lymphocyte, for instance, CTL, LAK cell, TIL or the like. The cell is further activated by binding IL-2 to interleukin-2 receptor (IL-2R) on a cell surface. In addition, IL-2R has been known as an activation marker for a lymphocyte. From these viewpoints, it is important to improve IL-2R expression on the cell surface. In addition, in the induction of CTL, it is important to improve an efficiency for inducing a precursor cell of CTL subjected to stimulation by an antigen as CTL, i.e., to improve a proportion (ratio) of the CD8-positive cell in a group of cells after the induction.

Fibronectin is a gigantic glycoprotein having a molecular weight of 250 thousands, which exists in an animal blood, on the surface of a cultured cell, or in an extracellular matrix of a tissue, and has been known to have various functions. A domain structure thereof is divided into seven portions (hereinafter refer to FIG. 1), wherein three kinds of similar sequences are contained in an amino acid sequence thereof; repetitions of each of these sequences constituting the entire sequence. Three kinds of the similar sequences are referred to as type I, type II and type III. Among them, the type III is constituted by 71 to 96 amino acid residues, wherein a coincidence ratio of these amino acid residues is 17 to 40%. In fibronectin, there are fourteen type III sequences, among which the 8th, 9th or 10th sequence (each being hereinafter referred to as III-8, III-9 or III-10) is contained in a cell binding domain, and the 12th, 13th or 14th sequence (each being hereinafter referred to as III-12, III-13 or III-14) is contained in a heparin binding domain. In addition, a VLA (very late activation antigen)-5 binding region is contained in III-10, and its core sequence is RGDS. In addition, a region referred to as IIICS exists at a C-terminal side of the heparin binding domain. A region referred to as CS-1 consisting of 25 amino acids and having a binding activity to VLA-4 exists in IIICS (Deane F. Momer, *FIBRONECTIN*, ACADEMIC PRESS INC., 1-8 (1988); Kimizuka F. et al., *J. Biochem.* 110, 284-291 (1991); Hanenberg H. et al., *Human Gene Therapy* 8, 2193-2206 (1997)).

DISCLOSURE OF INVENTION

An object of the present invention is to a method for preparing a cytotoxic lymphocyte having a cytotoxic activity at a high level, which is suitably used in the medical field.

Concretely, the present invention relates to:

[1] a method for preparing a cytotoxic lymphocyte characterized in that the method comprises the step of carrying out at least one of induction, maintenance and expansion of a cytotoxic lymphocyte in the presence of fibronectin, a fragment thereof or a mixture thereof;

[2] the method according to the above [1], wherein the cytotoxic lymphocyte highly expresses an interleukin-2 receptor as compared to a cytotoxic lymphocyte obtained by carrying out at least one of induction, maintenance and expansion in the absence of fibronectin, a fragment thereof or a mixture thereof;

[3] the method according to the above [1], wherein the cytotoxic lymphocyte contains CD8-positive cell in a higher ratio as compared to a cytotoxic lymphocyte obtained by carrying out at least one of induction, maintenance and expansion in the absence of fibronectin, a fragment thereof or a mixture thereof;

[4] the method according to any one of the above [1] to [3], wherein the cytotoxic lymphocyte highly maintains cytotoxic activity as compared to a cytotoxic lymphocyte obtained by carrying out at least one of induction, maintenance and expansion in the absence of fibronectin, a fragment thereof or a mixture thereof;

[5] the method according to any one of the above [1] to [4], wherein fibronectin, a fragment thereof or a mixture thereof is immobilized in a solid phase;

[6] the method according to the above [5], wherein the solid phase is a cell culture equipment or a cell culture carrier;

[7] the method according to the above [6], wherein the cell culture equipment is a petri dish, a flask or a bag, and the cell culture carrier is beads, a membrane or a slide glass;

[8] the method according to any one of the above [1] to [4], wherein at least one of induction, maintenance and expansion of a cytotoxic lymphocyte is carried out in a medium containing fibronectin, a fragment thereof or a mixture thereof;

[9] the method according to any one of the above [1] to [8], wherein the fibronectin fragment is a polypeptide comprising at least one of the amino acid sequences represented by SEQ ID NOs: 1 to 7 of Sequence Listing, or a polypeptide having substitution, deletion, insertion or addition of one or more amino acids in the amino acid sequence of the above polypeptide, wherein the polypeptide has functions equivalent to that of the above polypeptide;

[10] the method according to the above [9], wherein the fibronectin fragment has cell adhesion activity and/or heparin binding activity;

[11] the method according to the above [9], wherein the fibronectin fragment is a polypeptide selected from polypeptides comprising any one of the amino acid sequences shown in SEQ ID NOs: 8 to 19 of Sequence Listing;

[12] the method according to the above [1] comprising carrying out at least one of induction, maintenance and expansion of a cytotoxic lymphocyte in the presence of fibronectin, a fragment thereof or a mixture thereof in a cell culture equipment containing a medium, wherein the method satisfies any one of the conditions of:

(a) a ratio of the number of cells at initiation of culture to a culture area in the cell culture equipment being 1 to $5 \times 10^5$ cells/cm$^2$; and (b) a concentration of cells in a medium at initiation of culture being 1 to $5 \times 10^5$ cells/ml;

[13] the method according to the above [12], wherein the method excludes a dilution step or a step of exchanging a cell culture equipment;

[14] a cytotoxic lymphocyte obtained by the method of any one of the above [1] to [13];

[15] a medicament comprising as an effective ingredient a cytotoxic lymphocyte obtained by the method of any one of the above [1] to [13];

[16] an agent for enhancing an interleukin-2 receptor expression of a cell, characterized in that the agent comprises as an effective ingredient fibronectin, a fragment thereof or a mixture thereof;

[17] the agent according to the above [16], wherein the fibronectin fragment is a polypeptide comprising at least one of the amino acid sequences represented by SEQ ID NOs: 1 to 7 of Sequence Listing, or a polypeptide having substitution, deletion, insertion or addition of one or more amino acids in the amino acid sequence of the above polypeptide, wherein the polypeptide has functions equivalent to that of the above polypeptide;

[18] the agent according to the above [17], wherein the fibronectin fragment has cell adhesion activity and/or heparin binding activity;

[19] the agent according to the above [17], wherein the fibronectin fragment is a polypeptide selected from polypeptides comprising any one of the amino acid sequences shown in SEQ ID NOs: 8 to 19 of Sequence Listing;

[20] an agent for improving a ratio of CD8-positive cell in a lymphocyte, characterized in that the agent comprises as an effective ingredient fibronectin, a fragment thereof or a mixture thereof;

[21] the agent according to the above [20], wherein the fibronectin fragment is a polypeptide comprising at least one of the amino acid sequences represented by SEQ ID NOs: 1 to 7 of Sequence Listing, or a polypeptide having substitution, deletion, insertion or addition of one or more amino acids in the amino acid sequence of the above polypeptide, wherein the polypeptide has functions equivalent to that of the above polypeptide;

[22] the agent according to the above [21], wherein the fibronectin fragment has cell adhesion activity and/or heparin binding activity;

[23] the agent according to the above [21], wherein the fibronectin fragment is a polypeptide selected from polypeptides comprising any one of the amino acid sequences shown in SEQ ID NOs: 8 to 19 of Sequence Listing;

[24] an agent for improving or maintaining cytotoxic activity in a cytotoxic lymphocyte, characterized in that the agent comprises as an effective ingredient fibronectin, a fragment thereof or a mixture thereof;

[25] the agent according to the above [24], wherein the fibronectin fragment is a polypeptide comprising at least one of the amino acid sequences represented by SEQ ID NOs: 1 to 7 of Sequence Listing, or a polypeptide having substitution, deletion, insertion or addition of one or more amino acids in the amino acid sequence of the above polypeptide, wherein the polypeptide has functions equivalent to that of the above polypeptide;

[26] the agent according to the above [25], wherein the fibronectin fragment has cell adhesion activity and/or heparin binding activity;

[27] the agent according to the above [25], wherein the fibronectin fragment is a polypeptide selected from polypeptides comprising any one of the amino acid sequences shown in SEQ ID NOs: 8 to 19 of Sequence Listing;

[28] a method for increasing expression of an interleukin-2 receptor in a cytotoxic lymphocyte, characterized in that the method comprises the step of carrying out at least one of induction, maintenance and expansion of a cytotoxic lymphocyte in the presence of fibronectin, a fragment thereof or a mixture thereof;

[29] a method for improving a ratio of CD8-positive cell in a cytotoxic lymphocyte, characterized in that the method comprises the step of carrying out at least one of induction, maintenance and expansion of a cytotoxic lymphocyte in the presence of fibronectin, a fragment thereof or a mixture thereof;

[30] a method for improving or maintaining cytotoxic activity in a cytotoxic lymphocyte, characterized in that the method comprises the step of carrying out at least one of induction, maintenance and expansion of a cytotoxic lymphocyte in the presence of fibronectin, a fragment thereof or a mixture thereof;

[31] the method according to any one of the above [1] to [13], further comprising the step of transducing a foreign gene into a cytotoxic lymphocyte; and

[32] the method according to the above [31], wherein the foreign gene is transduced using retrovirus, adenovirus, adeno-associated virus or simian virus.

BRIEF DESCRIPTION OF THE DRAWINGS

FIG. 1 is a schematic view showing a domain structure of fibronectin.

BEST MODE FOR CARRYING OUT THE INVENTION

The present invention has been completed by the findings that in the cytotoxic lymphocyte prepared in the presence of fibronectin and/or a fragment thereof, a high cytotoxic activity is maintained, an expression level of IL-2R is significantly increased, and a ratio of the CD8-positive cell is improved.

Incidentally, the preparation of a cytotoxic lymphocyte as used herein refers to a step encompassing a step comprising each of the steps of induction (activation), maintenance and expansion of the cell, or the combined steps thereof. The preparation of a cytotoxic lymphocyte of the present invention is also referred to culture of a cytotoxic lymphocyte.

The present invention will be explained concretely hereinbelow.

(1) Fibronectin and Fragment Thereof Used in the Present Invention

The fibronectin and a fragment thereof as mentioned herein may be those obtained from nature, or those which are artificially synthesized. The fibronectin and a fragment thereof can be prepared in a substantially pure form from a substance of natural origin, on the basis of the disclosure of Ruoslahti E. et al. [*J. Biol. Chem.*, 256(14), 7277-7281 (1981)]. The term "substantially pure fibronectin or fibronectin fragment" as referred to herein means that these fibronectin and fibronectin fragment do not substantially contain other proteins and the like existing together with fibronectin in nature. Each of the above-mentioned fibronectin and a fragment thereof can be used in the present invention alone or in admixture of plural kinds.

The useful information relating to the fibronectin fragments which can be used in the present invention and the preparation of the fragments can be obtained from Kimiduka F., et al. [*J. Biochem.*, 110, 284-291 (1991)], Kornbrihtt A. R. et al. [*EMBO J.*, 4(7), 1755-1759 (1985)], Sekiguchi K., et al. [*Biochemistry*, 25(17), 4936-4941 (1986)], and the like.

In the present invention, the fibronectin fragment is exemplified by, for instance, a polypeptide comprising an amino acid sequence comprising at least any of the regions of III-8 (amino acid sequence shown in SEQ ID NO: 1 in Sequence Listing), III-9 (amino acid sequence shown in SEQ ID NO: 2 in Sequence Listing), III-10 (amino acid sequence shown in SEQ ID NO: 3 in Sequence Listing), III-12 (amino acid sequence shown in SEQ ID NO: 4 in Sequence Listing), III-13 (amino acid sequence shown in SEQ ID NO: 5 in Sequence Listing), III-14 (amino acid sequence shown in SEQ ID NO: 6 in Sequence Listing), and CS-1 (amino acid sequence shown in SEQ ID NO: 7 in Sequence Listing) (see FIG. 1).

In addition, as the fragment, a fragment having a cell adhesion activity and/or a heparin binding activity can be preferably used. The cell adhesion activity can be evaluated by assaying binding of the fragment (its cell binding domain) used in the present invention to a cell using a known method. For instance, the method as mentioned above includes a method of Williams D. A., et al. [*Nature*, 352, 438-441 (1991)]. The method is a method of determining the binding of a cell to a fragment immobilized to a culture plate. In addition, the heparin binding activity can be evaluated by assaying binding of the fragment (its heparin binding domain) used in the present invention to heparin using a known method. For instance, the binding of the fragment to heparin can be evaluated in the same manner by using heparin, for instance, a labeled heparin in place of the cell in the above-mentioned method of Williams D. A. et al.

Further, the fibronectin fragment is exemplified by a polypeptide selected from C-274 (amino acid sequence shown in SEQ ID NO: 8 in Sequence Listing), H-271 (amino acid sequence shown in SEQ ID NO: 9 in Sequence Listing)., H-296 (amino acid sequence shown in SEQ ID NO: 10 in Sequence Listing), CH-271 (amino acid sequence shown in SEQ ID NO: 11 in Sequence Listing), CH-296 (amino acid sequence shown in SEQ ID NO: 12 in Sequence Listing) or C-CS1 (amino acid sequence shown in SEQ ID NO: 13 in Sequence Listing).

Each of the above-mentioned fragments CH-271, CH-296, C-274 and C-CS 1 is a polypeptide having a cell binding domain with a binding activity to VLA-5. Also, C-CS1, H-296 or CH-296 is a polypeptide having a cell binding domain with a binding activity to VLA-4. Further, H-271, H-296, CH-271 or CH-296 is a polypeptide having a heparin binding domain.

In the present invention, a fragment in which each of the above domains is modified can also be used. The heparin binding domain of the fibronectin is constituted by three type III sequences (III-12, III-13 and III-14). A fragment containing a heparin binding domain having deletion of one or two of the type III sequences can also be used in the present invention. For instance, the fragments may be exemplified by CHV-89 (amino acid sequence shown in SEQ ID NO: 14 of Sequence Listing), CHV-90 (amino acid sequence shown in SEQ ID NO: 15 of Sequence Listing) or CHV-92 (amino acid sequence shown in SEQ ID NO: 16 of Sequence Listing), which is a fragment in which a cell binding site of the fibronectin (VLA-5 binding domain: Pro1239 to Ser1515) and one of the III type sequences are bound, or CHV-179 (amino acid sequence shown in SEQ ID NO: 17 of Sequence Listing) or CHV-181 (amino acid sequence shown in EQ ID NO: 18 of Sequence Listing), which is a fragment in which the cell binding site of the fibronectin and two of the type III sequences are bound. CHV-89, CHV-90 and CHV-92 contain III-13, III-14 and III-12, respectively, and CHV-179 contains III-13 and III-14, and CHV-181 contains III-12 and III-13, respectively.

In addition, a fragment having addition of an additional amino acid to each of the above-mentioned fragments can be used in the present invention. For instance, the fragment can be prepared by adding a desired amino acid to each of the above-mentioned fragment in accordance with the method for preparing H-275-Cys described in Preparation Examples set forth below. For instance, H-275-Cys (amino acid sequence shown in SEQ ID NO: 19 of Sequence Listing) is a fragment having a heparin binding domain of the fibronectin, and cysteine residue at a C-terminal.

The fragment used in the present invention may be those comprising a polypeptide comprising an amino acid sequence having substitution, deletion, insertion or addition of one or more amino acids in an amino acid sequence of a polypeptide constituting a fragment at least partially containing an amino acid sequence of naturally occurring fibronectin exemplified above, wherein the polypeptide has an equivalent function to the fragment, so long as the desired effects of the present invention are obtained.

It is preferable that the substitution or the like of the amino acids is carried out to an extent that it can change physico-chemical characteristics and the like of an inherent polypeptide within the range that the function of the polypeptide can be maintained. For instance, the substitution or the like of amino acids is conservative, within the range that the characteristics inherently owned by the polypeptide (for instance, hydrophobicity, hydrophilicity, electric charge, pK and the like) are not substantially changed. For instance, the substitution of the amino acids is substitutions within each of the groups of ① glycine, alanine; ② valine, isoleucine, leucine; ③ aspartic acid, glutamic acid, asparagine, glutamine; ④ serine, threonine; ⑤ lysine, arginine; ⑥ phenylalanine, tyrosine. Deletion, addition or insertion of amino acids is deletion, addition or insertion in the amino acids having characteristics similar to the characteristics of the surroundings of the subject site in the polypeptide within the range that the characteristics of the surroundings of the subject site are not substantially changed.

In addition, the phrase "having an equivalent function" refers to that having at least any of the functions of (i) a function of maintaining a cytotoxic activity of a cytotoxic lymphocyte, (ii) a function of enhancing an expression level of IL-2R, or (iii) a function of improving a ratio of CD8-positive cell. Whether or not the fragment comprising a polypeptide having substitution or the like of amino acids has those functions can be appropriately confirmed in accordance with the method described in Examples set forth below. In addition, as the fragment comprising a polypeptide having substitution or the like of amino acids, the fragment having a cell adhesion activity and/or a heparin binding activity is preferred. The cell adhesion activity and the heparin binding activity can be evaluated in accordance with the above-mentioned methods for determining those activities.

As the fragment comprising a polypeptide having substitution or the like of amino acids, for instance, a fragment having one or more amino acids inserted as a linker between two different domains can also be used in the present invention.

Incidentally, as the fibronectin per se, similarly, there can be used in the present invention a polypeptide having an amino acid sequence having substitution, deletion, insertion or addition of one or more amino acids in an amino acid sequence constituting the polypeptide of the fibronectin, wherein the polypeptide has at least any of the functions of the above-mentioned (i) to (iii).

The fibronectin fragment as referred to herein can also be prepared from a genetic recombinant on the basis of the description of, for instance, U.S. Pat. No. 5,198,423. For instance, each of the fragments of H-271 (SEQ ID NO: 9), H-296 (SEQ ID NO: 10), CH-271 (SEQ ID NO: 11) and CH-296 (SEQ ID NO: 12) and a method of preparing these fragments are described in detail in the specification of this patent. In addition, the above-mentioned C-274 (SEQ ID NO: 8) fragment can be obtained in accordance with the method described in U.S. Pat. No. 5,102,988. Further, a C-CS1 (SEQ ID NO: 13) fragment can be obtained in accordance with the method described in Japanese Patent Gazette No. 3104178. Each of the fragment of CHV-89 (SEQ ID NO: 14), CHV-90 (SEQ ID NO: 15) or CHV-179 (SEQ ID NO: 17) can be obtained in accordance with the method described in Japanese Patent Gazette No. 2729712. In addition, the CHV-181 (SEQ ID NO: 18) fragment can be obtained in accordance with the method described in WO 97/18318. The CHV-92 (SEQ ID NO: 16) fragment can be obtained by genetic engineering technique using a plasmid constructed in a usual manner on the basis of the plasmid described in these literatures by referring to Japanese Patent Gazette No. 2729712 and WO 97/18318.

These fragments or fragments which can be derived from these fragments in a usual manner can be prepared by using microorganisms deposited to the International Patent Organism Depositary, National Institute of Advanced Industrial Science and Technology, Tsukuba Central 6, 1-1, Higashi 1-chome, Tsukuba-shi, Ibaraki-ken, Japan (Zip code 305-

8566) under the following accession numbers, or by modifying a plasmid carried in each microorganism in accordance with a known method.

FERM BP-2264 (*Escherichia coli* carrying a plasmid encoding H-271, Date of Deposit: Jan. 30, 1989);

FERM BP-2800 (*Escherichia coli* carrying a plasmid encoding CH-296, Date of Deposit: May 12, 1989);

FERM BP-2799 (*Escherichia coli* carrying a plasmid encoding H-271, Date of Deposit: May 12, 1989);

FERM BP-7420 (*Escherichia coli* carrying a plasmid encoding H-296, Date of Deposit: May 12, 1989);

FERM BP-1915 (*Escherichia coli* carrying a plasmid encoding C-274, Date of Deposit: Jun. 17, 1988);

FERM BP-5723 (*Escherichia coli* carrying a plasmid encoding C-CS1, Date of Deposit: Mar. 5, 1990);

FERM P-12182 (*Escherichia coli* carrying a plasmid encoding CHV-89, Date of Deposit: Apr. 8, 1991); and FERM P-12183 (*Escherichia coli* carrying a plasmid encoding CHV-179, Date of Deposit: Apr. 8, 1991).

Since the fibronectin is a gigantic glycoprotein, it is not necessarily easy to prepare and use a naturally occurring protein for the industrial purpose and for the purpose of the preparation of the medicament. Further, the fibronectin exists in a large amount in plasma in a living body. Therefore, when a fibronectin obtained from plasma is used as a blood preparation, there is a risk of contamination of components other than the fibronectin, so that there is considered to have a problem from the aspect of safety. In addition, since the fibronectin is a multifunctional protein, there may be considered some disadvantages caused by a region different from the region exhibiting the effect by the method of the present invention depending on the circumstances of its use. For these reasons, a fibronectin fragment can be preferably used in the present invention, more preferably a recombinant fibronectin fragment obtained as described above can be used from the viewpoints of availability, easy handling and safety. Further, there can be especially preferably used a fibronectin fragment which can exhibit an effect such as improvement in an expansion ratio of a lymphocyte, increase in an expression level of IL-2R in an expanded lymphocyte, or improvement in a ratio of CD8-positive cell in an expanded lymphocyte population as described below. In addition, the molecular weight of the fibronectin fragment used in the present invention is, but not particularly limited to, preferably from 1 to 200 kD, more preferably from 5 to 190 kD, even more preferably from 10 to 180 kD.

(2) Method for Preparing Cytotoxic Lymphocyte of the Present Invention

The method for preparing the cytotoxic lymphocyte of the present invention will be concretely explained below. The method of the present invention is a method for preparing cytotoxic lymphocyte comprising the step of carrying out at least any one of induction, maintenance and expansion of a cytotoxic lymphocyte in the presence of the above-mentioned fibronectin, a fragment thereof or a mixture thereof.

The "cytotoxic lymphocyte" as used herein means a group of cells containing a cytotoxic lymphocyte. In a narrow sense, the cytotoxic lymphocyte may be referred only to a cytotoxic lymphocyte contained in the above-mentioned group of cells in some cases. In addition, the preparation of the cytotoxic lymphocyte in the present invention encompasses any of induction from a precursor cell which can be formed into the lymphocyte of the present invention to a lymphocyte having a cytotoxic activity, maintenance of the cytotoxic lymphocyte, and expansion of the cytotoxic lymphocyte using the cytotoxic lymphocyte and/or the precursor cell.

The cytotoxic lymphocyte of the present invention includes, but not particularly limited to, for instance, cytotoxic T cell (CTL), lymphokine-activated killer cell (LAK cell), tumor-infiltrating lymphocyte (TIL), NK cell and the like, each having an antigen-specific cytotoxic activity.

In the present invention, the precursor cell which can be formed into a cytotoxic lymphocyte, i.e., the precursor cell which has an ability of differentiating into the lymphocyte, is exemplified by PBMC, NK cell, naive cell, memory cell, hemopoietic stem cell, umbilical cord blood mononuclear cell and the like. In addition, so long as a cell is a hemocyte, the cell can be used as a precursor cell in the present invention. Any of these cells which are collected from a living body can be used directly or those which are subjected to frozen storage can be used. Incidentally, in the method for preparing a cytotoxic lymphocyte of the present invention, a material containing the above-mentioned cells, for instance, a blood such as peripheral blood or umbilical cord blood; one obtained by removing components such as erythrocyte and plasma from the blood; a marrow fluid and the like can be used.

One of the major characteristics of the method for preparing a cytotoxic lymphocyte of the present invention resides in that the cytotoxic lymphocyte is prepared in the presence of an effective ingredient selected from fibronectin, a fragment thereof or a mixture thereof.

In the method of the present invention, the induction, maintenance and/or expansion of the cytotoxic lymphocyte is usually performed in a medium containing given components in the presence of the above-mentioned effective ingredient of the present invention.

For instance, in the method of the present invention, when the induction or expansion of the cytotoxic lymphocyte is intended, the number of cells (cytotoxic lymphocytes and/or precursor cells) at the initiation of culture used in the present invention is not particularly limited. For instance, the number is preferably from 1 to $1 \times 10^8$ cells/ml. In addition, the culture conditions are not particularly limited, and usual conditions for cell culture can be employed. For instance, cells can be cultured under the conditions of 37° C. in the presence of 5% $CO_2$ and the like. In addition, the medium can be exchanged with a fresh medium at appropriate intervals.

The medium used in the method for preparing a cytotoxic lymphocyte of the present invention is not particularly limited, and a known medium prepared by mixing components necessary for maintaining and growing a cytotoxic lymphocyte or its precursor cell can be used. For instance, a commercially available medium may be used. These media may contain appropriate proteins, cytokines and other components in addition to the inherent constituents. Preferably, a medium containing IL-2 is used in the present invention. The concentration of IL-2 in the medium is, but not particularly limited to, for instance, preferably from 0.01 to $1 \times 10^5$ U/ml, more preferably from 0.1 to $1 \times 10^4$ U/ml.

In addition, a precursor cell which can be formed into a cytotoxic lymphocyte can be co-cultured in a medium further containing an anti-CD3 antibody. The concentration of the anti-CD3 antibody in a medium is, but not particularly limited to, for instance, preferably from 0.01 to 100 µg/ml. The anti-CD3 antibody can be added for the purpose of activating a receptor on a lymphocyte. Also, besides the above, a lymphocyte-stimulating factor such as lecithin can be added. The concentration of the component in a medium is not particularly limited, so long as the desired effects can be obtained.

Besides the coexistence of these components by dissolving the components in a medium, there may be used by immobilization to an appropriate solid phase, for instance, a cell culture equipment (including any of those of open system and closed system), such as a petri dish, a flask or a bag, or to a cell culture carrier such as beads, a membrane or a slide glass. The materials for those solid phases are not particularly limited so long as the materials can be used for cell culture. When the components are immobilized to, for instance, the above-mentioned equipment, it is preferable to immobilize a given amount of each component to the amount of the medium to be placed in the equipment so that the medium has a similar proportion to a desired concentration of the case where the components are used by dissolving the components in a medium upon placing the medium in the equipment. The amount of the components immobilized is not particularly limited, so long as the desired effects can be obtained. The above-mentioned carrier is used by immersing the carrier in a culture medium in the cell culture equipment during the cell culture. When the above-mentioned components are immobilized to the above-mentioned carrier, it is preferable to immobilize a given amount of each component to the amount of the medium to be placed in the equipment so that the medium has a similar proportion to a desired concentration of the case where the components are used by dissolving the components in a medium upon placing the carrier in the medium. The amount of the components immobilized is not particularly limited, so long as the desired effects can be obtained.

In both cases, the immobilization of the above-mentioned components can be carried out by a known method, for instance, a method for immobilizing a fibronectin fragment set forth below.

Furthermore, there may be used together with the above-mentioned components a compound selected from the group consisting of acidic polysaccharides, acidic oligosaccharides, acidic monosaccharides and salts thereof which are effective for induction of a cytotoxic T cell having an antigen-specific cytotoxic activity, described in WO 02/14481, or a substance selected from the following (A) to (D):
(A) a substance having a binding activity to CD44;
(B) a substance capable of regulating a signal emitted by binding a CD44 ligand to CD44;
(C) a substance capable of inhibiting binding of a growth factor to a growth factor receptor; and
(D) a substance capable of regulating a signal emitted by binding of a growth factor to a growth factor receptor.

The above-mentioned substance having a binding activity to CD44 is exemplified by, for instance, a CD44 ligand and/or an anti-CD44 antibody. The substance capable of regulating a signal emitted by binding a CD44 ligand to CD44 includes, for instance, various inhibitors for phosphoenzymes. The substance capable of inhibiting binding of a growth factor to a growth factor receptor includes, for instance, a substance having a binding activity to a growth factor and forming a complex with the growth factor, thereby inhibiting the binding of the growth factor to a growth factor receptor, or a substance having a binding activity to a growth factor receptor, thereby inhibiting the binding of the growth factor to a growth factor receptor. Furthermore, the substance capable of regulating a signal emitted by binding of a growth factor to a growth factor receptor includes, for instance, various inhibitors for phosphoenzymes. The concentration of these components in the medium is not particularly limited, so long as the desired effects can be obtained. Also, these components may be used by immobilization to the appropriate solid phase as mentioned above in addition to the coexistence of these components in the medium by dissolving the components in the medium.

Here, each of various substances mentioned above can be used alone or in admixture of two or more kinds.

In the present invention, the phrase "in the presence of the above-mentioned effective ingredient" refers to the fact that the effective ingredient is present in a state that the above-mentioned effective ingredient can exhibit its function when the induction, maintenance and expansion of the cytotoxic lymphocyte is carried out, and the existing manner is not particularly limited. For instance, when the effective ingredient is dissolved in the medium to be used, the content of the effective ingredient of the present invention in the medium in which co-culture is carried out is not particularly limited, so long as the desired effects are obtained. The content of the effective ingredient is, for instance, preferably from 0.01 to 1000 µg/ml, more preferably from 0.1 to 1000 µg/ml, even more preferably from 1 to 100 µg/ml. Besides the coexistence of the effective ingredient by dissolving the effective ingredient in a medium as above, there may be used by immobilization to an appropriate solid phase, for instance, a cell culture equipment (including any of those of open system and closed system), such as a petri dish, a flask or a bag, or to a cell culture carrier such as beads, a membrane or a slide glass. From the viewpoint of administering the cultured cytotoxic lymphocyte to a living body, it is desired that the above-mentioned effective ingredient is immobilized, but it is not particularly limited thereto.

Once various components mentioned above or the effective ingredient of the present invention is immobilized to the solid phase, the cytotoxic lymphocyte can be easily separated from the effective ingredient or the like after the lymphocyte is obtained by the method of the present invention only by separating the lymphocyte from the solid phase, so that the contamination of the effective ingredient into the lymphocyte can be prevented.

When the effective ingredient of the present invention is immobilized to, for instance, the above-mentioned equipment, it is preferable to immobilize a given amount of each effective ingredient to the amount of the medium to be placed in the equipment so that the medium has a similar proportion to a desired concentration in a case where the effective ingredient is used by dissolving the effective ingredient in a medium upon placing the medium in the equipment. The amount of the effective ingredient is not particularly limited, so long as the desired effects are obtained. When the effective ingredient is immobilized to the above-mentioned carrier, it is preferable to immobilize a given amount of each effective ingredient to the amount of the medium to be placed into a equipment so that the medium has a similar proportion to a desired concentration in a case where the effective ingredient is used by dissolving the effective ingredient in a medium upon placing the carrier into the medium. The amount of the effective ingredient is not particularly limited, so long as the desired effects are obtained.

For instance, the immobilization of the fibronectin fragment can be carried out in accordance with the methods described in WO 97/18318 and WO 00/09168.

When the expression level of IL-2R is determined for the cytotoxic lymphocyte obtained by the method of the present invention, a significant increase in expression level of IL-2R is recognized as compared to a cytotoxic lymphocyte obtained by carrying out at least any one of induction, maintenance and expansion in the absence of fibronectin, a fragment thereof or a mixture thereof. Here, the expression level of IL-2R can be determined by a known method, for instance, using an anti-IL-2R antibody.

As described above, the cytotoxic lymphocyte obtained by the method of the present invention has an increased expression level of IL-2R. IL-2R is an activation marker which is expressed on a surface of an activated T cell, and with the expression of this molecule, cytokine production, cytotoxic activity, proliferation activation or the like is activated. Therefore, the cytotoxic lymphocyte obtained by the method of the present invention is a group of cells having a high function.

In addition, since the cytotoxic lymphocyte obtained by the method of the present invention has an increased expression level of IL-2R, the cytotoxic lymphocyte has an increased sensitivity to a stimulation by IL-2 added to a medium, or IL-2 produced by a precursor cell of a cytotoxic lymphocyte, a lymphocyte itself or other coexisting cell. For this reason, the cytotoxic lymphocyte can be activated by itself even under the environment of a smaller amount of IL-2 (for instance, in a living body or the like).

Further, in the cytotoxic lymphocyte obtained by the method of the present invention, the existence ratio of (CD8-positive) cell having a CD8 marker is high as compared to that of the cytotoxic lymphocyte obtained by carrying out at least any one of induction, maintenance and expansion in the absence of fibronectin, a fragment thereof or a mixture thereof. This fact has some advantages, for instance, ① that the CD8-positive cell produces a cytokine such as interferon-γ, thereby causing immunological activation to change a helper T cell balance into the Th1 dominant system, ② that the CD8-positive cell is a cellular immunocyte that can efficiently exclude a foreign substance such as a virus or a tumor cell, ③ that when the CD8-positive cell is obtained, the CD8-positive cell can be enriched with culturing the cell in accordance with the method of the present invention, while the CD8-positive cell has been conventionally purified with magnet beads or a flow cytometer, ④ that the cytotoxic lymphocyte is suitably used as a precursor cell during the induction of CTL, because the ratio of the CD8-positive cell is high, ⑤ that even a cell population having a lower ratio of the CD8-positive cell can be cultured with increasing the ratio of the CD8-positive cell and the like. Therefore, the method of the present invention is very useful in the preparation of a cytotoxic lymphocyte.

Here, the ratio of the CD8-positive cell in the cytotoxic lymphocyte obtained by the method of the present invention can be determined by, for instance, but not particularly limited to, using an anti-CD8 antibody.

In addition, the cytotoxic lymphocyte, especially CTL, prepared according to the method of the present invention has an excellent characteristic that there is no drastic decrease in cytotoxic activity as previously observed, even when a cell after the culture is maintained over a long period of time, or the cell is proliferated. In other words, the cytotoxic lymphocyte maintains a high cytotoxic activity as compared to a cytotoxic lymphocyte obtained by carrying out at least any one of induction, maintenance and expansion in the absence of fibronectin, a fragment thereof or a mixture thereof. Therefore, there can be maintained as a lymphocyte having a stable cytotoxic activity by cloning the cultured cytotoxic lymphocyte. In addition, the induced CTL can be proliferated and expanded by stimulating the CTL with an antigen, various kinds of cytokines, or an anti-CD3 antibody. A known method can be used for the maintenance or expansion of the cytotoxic lymphocyte without being particularly limited.

The maintenance of the above-mentioned cytotoxic lymphocyte refers to the maintenance of the cytotoxic lymphocyte with keeping its cytotoxic activity. The culture conditions during the maintenance are not particularly limited, and the conditions used for ordinary cell culture can be used. For instance, the cells can be cultured under the conditions of 37° C. in the presence of 5% $CO_2$, and the like. In addition, the medium can be exchanged with a fresh one at appropriate time intervals. The medium to be used and other components simultaneously used therewith and the like are the same as those mentioned above.

One of the major characteristics of the maintenance and expansion of the cytotoxic lymphocyte in the method of the present invention resides in that the method comprises respectively continuously culturing and expanding the cytotoxic lymphocyte in a medium in the presence of the effective ingredient of the present invention, i.e. fibronectin, a fragment thereof or a mixture thereof. According to the expansion, the cell number of the cytotoxic lymphocyte can be increased in a state that the cytotoxic activity owned by the cytotoxic lymphocyte is maintained. In other words, as one embodiment of the method of the present invention, there is provided a method for expanding a cytotoxic lymphocyte.

In the method for expanding a cytotoxic lymphocyte of the present invention, the culture conditions are not particularly limited, and the conditions used for ordinary cell culture can be used. For instance, the cells can be cultured under the conditions at 37° C. in the presence of 5% $CO_2$, and the like. In addition, the medium can be exchanged with a fresh one at appropriate time intervals. The medium to be used and other components simultaneously used therewith and the like are the same as those mentioned above.

According to the method for expansion of the present invention, for instance, in the case of the expansion of CTL, CTL of which cell number is increased 100- to 1000-folds can be obtained by expansion for 14 days. In addition, as one example of the case of expansion of LAK cell, there can be obtained LAK cell increased in about 200-folds by culturing the cell for 7 days, and in about 1000-folds by culturing the cell for 9 days. Further, the thus obtained cytotoxic lymphocyte, especially CTL, has a higher cytotoxic activity as compared to one obtained by a conventional method for expanding a cytotoxic lymphocyte, for instance, a REM method or a modified REM method. The effects of the present invention as described above can be confirmed by determining a cytotoxic activity owned by CTL or the like expanded by the method of the present invention, in accordance with the method described in Examples set forth below.

Further, the method for preparing a cytotoxic lymphocyte of the present invention has the feature that the culture can be initiated at a low number of cells. A large amount of lymphocytes is required in order to carry out adopted immunotherapy, but it is difficult to obtain a large amount of lymphocytes from a patient. In addition, in an ordinary expansion of the cytotoxic lymphocyte, there have been necessitated selection of a cell culture equipment having an appropriate culture area depending upon the number of cells to be used, and culture at an appropriate amount of the medium. In other words, usually, the culture is initiated under the high density conditions that the amount (number) of cells to a culturing area in a cell culture equipment [i.e. area ($cm^2$) of a surface area of the equipment contacting with the medium] is $1 \times 10^6$ cells/$cm^2$ or more, and the cell concentration is $1 \times 10^6$ cells/ml or more. When the culture is carried out under the conditions below this cell level, an expansion ratio [a ratio of the number of cells after the expansion to the number of cells before the expansion (number of cells after expansion/number of cells before expansion)] becomes very low, whereby requiring a long-term culture period before the cytotoxic lymphocytes are obtained in a large amount. Therefore, generally, a large number of lymphocytes are currently prepared by, for instance, initiating the culture using a small cell culture equipment, and thereafter using a stepwise, large-scaled cell culture equipment, or a method of increasing the number of cell culture equipments and repeating dilution procedures. As described above, a plurality of culture systems are required in the ordinary expansion of the cytotoxic lymphocyte.

According to the method of the present invention, even when initiated with a small amount of cells, the cell can be cultured with a high expansion ratio regardless of the size of a cell culture equipment. Therefore, a complicated procedure such as an exchange of the cell culture equipment and the dilution procedures as described above become unnecessary. In other words, according to the method of the present invention, the expansion of the cytotoxic lymphocyte can be satisfactorily carried out by culture procedures using one cell culture equipment, i.e., one culture system. Therefore, the method of the present invention is a method for preparing a cytotoxic lymphocyte which excludes the dilution step or the step of exchanging a cell culture equipment. Especially, when LAK cell is expanded according to the method of the present invention, LAK cell can be expanded by adding a cell which can be formed into a LAK cell and a medium to a large-volume cell culture equipment, and adding only IL-2 thereto in subsequent steps. The present invention is very useful in the aspect that a large amount of LAK cell can be obtained by a simple procedure. Here, the fibronectin fragment can be preferably used as the effective ingredient of the present invention to be used from the viewpoint of obtaining a higher expansion ratio. As described above, according to the method of the present invention, a necessary amount of the cytotoxic lymphocyte can be obtained in a shorter time period.

For instance, when at least any one of induction, maintenance and expansion of a cytotoxic lymphocyte is initiated at a low number of cells in a cell culture equipment containing a medium in the presence of the effective ingredient of the present invention, the induction, maintenance or expansion can be carried out by using an amount of the cell satisfying the conditions selected from the followings (a) and (b) at the initiation of culture:

(a) the ratio of the amount of cells to the culture area in the cell culture equipment to be used being preferably from 1 to $5 \times 10^5$ cells/cm$^2$, more preferably from 10 to $1 \times 10^5$ cells/cm$^2$, especially preferably from $1 \times 10^2$ to $5 \times 10^4$ cells/cm$^2$; and (b) the concentration of the cells in the medium being preferably from 1 to $5 \times 10^5$ cells/ml, more preferably from 10 to $1 \times 10^5$ cells/ml, especially preferably from $1 \times 10^2$ to $5 \times 10^4$ cells/ml.

The amount of cells as used herein refers to the number of cytotoxic lymphocytes and/or precursor cells.

In addition, in the method of the present invention, there can be exemplified a method comprising carrying out at least any one of induction, maintenance and expansion of a cytotoxic lymphocyte in one culturing system, which excludes the step of exchange of a cell culture equipment or the step of the dilution procedure.

The method of the present invention will be explained by taking the preparation of CTL as an example.

The induction of CTL is carried out by incubating (culturing) a precursor cell capable of differentiating to CTL together with an appropriate antigen-presenting cell in the presence of the above-mentioned effective ingredient in, for instance, any of medium, in order to give CTL an ability of recognizing the desired antigen. The precursor cell is not particularly limited, so long as the precursor cell is a cell which is in a stage before the cell becomes CTL and fated to differentiate to CTL, and includes, for instance, peripheral blood mononuclear cell (PBMC), naive cell, memory cell, umbilical cord blood mononuclear cell, hemopoietic stem cell, and the like. The antigen-presenting cell is not particularly limited, so long as the cell has an ability to present an antigen to be recognized to T cell. For instance, mononuclear cell, B cell, T cell, macrophage, dendritic cell, fibroblast or the like which is allowed to present a desired antigen can be used in the present invention.

In the present invention, the culture conditions for a precursor cell or the like during the preparation of CTL may be, for instance, set in accordance with generally known conditions [see, for instance, Carter J. et al., Immunology 57(1), 123-129 (1986)].

In addition, the cell can be co-cultured with an appropriate feeder cell. When the CTL is co-cultured with the feeder cell, it is desired that the medium is one that is suitable for maintenance and growth of both the CTL and the feeder cell. As the medium, a commercially available medium can be used.

The feeder cell used for the method of the present invention is not particularly limited, so long as the feeder cell stimulates CTL cooperatively with an anti-CD3 antibody to activate T cell receptor. In the present invention, for instance, PBMC or B cell transformed with Epstein-Barr virus (EBV-B cell) is used. Usually, a feeder cell is used after its proliferating ability is taken away by means of irradiation or the like. Incidentally, the content of the feeder cell in the medium may be determined according to the known conditions. For instance, the content is preferably from $1 \times 10^{5-7}$ cells/ml.

In a particularly preferred embodiment of the present invention, non-virus-infected cell, for instance, a cell other than EBV-B cell, is used as a feeder cell. By using the non-virus-infected cell, the possibility that EBV-B cell is admixed in an expanded CTL can be eliminated, thereby making it possible to increase the safety in medical treatments utilizing CTL, such as adoptive immunotherapy.

The antigen-presenting cell can be prepared by adding an antigenic peptide to a cell having an antigen-presenting ability, thereby allowing the cell to present the antigenic peptide on its surface [see, for instance, Bendnarek M. A. et al., *J. Immunol.* 147(12), 4047-4053 (1991)]. In addition, in the case where a cell having an antigen-presenting ability has an ability to process an antigen, an antigen is added to the cell, whereby the antigen is incorporated into the cell and processed therein, and fragmented antigenic peptides are presented on the cell surface. Incidentally, when an antigenic peptide is added to a cell having an antigen-presenting ability, an antigenic peptide matching the MHC restriction of the antigen-presenting cell used and the CTL to be induced are used.

Incidentally, the antigen used in the present invention is not particularly limited, and includes, for instance, exogenous antigens such as bacteria and viruses, endogenous antigens such as tumor-associated antigens (cancer antigens), and the like.

In the present invention, it is preferable that the antigen-presenting cell is made non-proliferative. In order to make the cell non-proliferative, the cell may be, for instance, subjected to irradiation with X-ray or the like, or a treatment with an agent such as mitomycin.

In the present invention, common conditions for incubating (co-culturing) a precursor cell capable of differentiating to CTL together with an antigen-presenting cell in the presence of the effective ingredient selected from fibronectin, a fragment thereof or a mixture thereof to induce CTL may be known conditions [see, for instance, Bendnarek M. A. et al., *J. Immunol.*, 147(12), 4047-4053 (1991)]. The co-culture conditions are not particularly limited, and the conditions usually used for the cell culture can be used. For instance, the cells can be cultured under the conditions of 37° C. in the presence of 5% $CO_2$, and the like. The co-culture is usually carried out for about 2 to about 15 days, during which time the antigen-presenting cell may be exchanged with freshly prepared one for restimulation. In addition, the medium can be exchanged with a fresh one at appropriate time intervals.

The CTL thus obtained by the method of the present invention has an ability of specifically recognizing the desired antigen, for instance, specifically destroying a cell having the antigen by its cytotoxic activity. This cytotoxic activity of the CTL can be evaluated by a known method. For instance, the cytotoxic activity of the CTL against a target cell labeled with a radioactive substance, a fluorescent substance or the like can be evaluated by determining radioactivity or fluorescent intensity ascribed to the target cell destroyed by the CTL. In addition, there can be detected by determining the amount of a cytokine such as GM-CSF or IFN-γ released antigen-specifically from the CTL or a target cell. Besides them, the cytotoxic activity can be directly confirmed by using an antigenic peptide-MHC complex in which the peptide is labeled with a fluorescent pigment or the like. In this case, for instance, the CTL is contacted with a first fluorescent marker coupled with a CTL-specific antibody, and then with an antigenic peptide-MHC complex in which the peptide is coupled with a second fluorescent marker, and the presence of a double-labeled cell is detected by FACS (fluorescence-activated cell sorting) analysis, whereby the cytotoxic activity of CTL can be evaluated.

Incidentally, the method for expanding CTL of the present invention is not particularly limited, so long as the above-mentioned effective ingredient exists in the culture system used in the method. The present invention also encompasses an embodiment in which the method is carried out by the existence of the above-mentioned effective ingredient in the culture system in a conventional method for expansion of CTL other than those described above, i.e. the culture of a precursor cell or the like is carried out in the presence of the effective ingredient of the present invention (for instance, by adding the above-mentioned effective ingredient to a medium to be used in the culture).

Next, the method for culturing LAK cell will be explained in detail.

The culture of LAK cell is carried out by incubating a cell which can be formed into LAK cell together with IL-2 in the presence of the above-mentioned effective ingredient. The cell which can be formed into LAK cell includes, but not particularly limited to, for instance, peripheral blood mononuclear cell (PBMC), NK cell, umbilical cord blood mononuclear cell, hemopoietic stem cell, blood components containing these cells, and the like.

In addition, the general conditions for culturing LAK cell may be set in accordance with the known conditions [for instance, see *Saibo Kogaku*(*Cell Technology*), 14(2), 223-227 (1995); *Saibo Baiyo*(*Cell Culture*) 17(6), 192-195 (1991); *THE LANCET*, 356, 802-807 (2000); *Current Protocols in Immunology*, supplement 17, UNIT 7.7]. The co-culture conditions are not particularly limited, and the conditions which are used in ordinary cell culture can be employed. For instance, the culture can be carried out under the conditions of 37° C. in the presence of 5% $CO_2$, and the like This co-culture is usually carried out for about 2 to about 15 days. In addition, the medium may be exchanged with a fresh one at appropriate time intervals.

In the same manner as those for the above-mentioned induction, maintenance or expansion of the CTL or the LAK cell, as to TIL, a group of cells having a high cytotoxic activity can be prepared by culturing the cells in the presence of fibronectin, a fragment thereof or a mixture thereof. In the present invention, there are no particular limitation in the procedures of activating these cells so long as fibronectin, a fragment thereof or a mixture thereof is coexistent therewith, and the procedures can be carried out using a medium appropriate for culture or activation of the above-mentioned cells. As to the amount of fibronectin, a fragment thereof or a mixture thereof used, the method of adding the component and the like, appropriate ones may be selected in accordance with the above-mentioned method.

According to the above-mentioned method for preparing a cytotoxic lymphocyte of the present invention, there is obtained a cytotoxic lymphocyte in which a cytotoxic activity is maintained at a high level, an expression level of IL-2R is significantly increased, and a ratio of a CD8-positive cell is improved, the cytotoxic lymphocyte which is suitable for use in medicine. Accordingly, as one embodiment of the method of the present invention, there are further provided a method for increasing expression of an interleukin-2 receptor in a cytotoxic lymphocyte, comprising the step of carrying out at least any one of induction, maintenance and expansion of a cytotoxic lymphocyte in the presence of the effective ingredient of the present invention; a method for improving a ratio of CD8-positive cell in a cytotoxic lymphocyte, comprising the step of carrying out any one of induction, maintenance and expansion of a cytotoxic lymphocyte in the presence of the effective ingredient of the present invention; and a method for improving or maintaining a cytotoxic activity in a cytotoxic lymphocyte, comprising the step of carrying out at least any one of induction, maintenance and expansion of a cytotoxic lymphocyte in the presence of the effective ingredient of the present invention.

In another embodiment of the present invention, there is provided an agent for enhancing IL-2R expression on a cell surface, which comprises as an effective ingredient fibronectin, a fragment thereof or a mixture thereof. The enhancing agent comprises the effective ingredient itself and further other optional ingredient, for instance, a medium, a protein, and a cytokine (preferably IL-2) which are appropriate for a cell to be activated, and other desired components. Also, the medium containing the above-mentioned enhancing agent can be employed as a medium for enhancing IL-2R expression in a cytotoxic lymphocyte. The above-mentioned medium optionally contains basic components for the cell culture. Here, the enhancing agent and the medium for enhancing IL-2R expression mentioned above can be prepared using the effective ingredient of the present invention in accordance with a known method. The content of the effective ingredient of the present invention and the like in the enhancing agent or the medium for enhancing IL-2R expression mentioned above is not particularly limited, so long as the desired effects of the present invention are obtained. For instance, the content can be appropriately determined in accordance with the content of the effective ingredient and the like in the above-mentioned medium used in the method of the present invention as desired. In addition, the above-mentioned enhancing agent may be directly administered to a living body, whereby IL-2R expression on a cell in a living body can be enhanced.

In still another embodiment of the present invention, there is provided an agent for improving a ratio of CD8-positive cell in a cultured lymphocyte population, characterized in that the agent comprises as an effective ingredient fibronectin, a fragment thereof or a mixture thereof. The ratio-improving agent comprises the effective ingredient itself and further other optional ingredient, for instance, a medium, a protein, and a cytokine (preferably IL-2) which are appropriate for a cell to be activated, and other desired components. Also, the medium containing the above-mentioned ratio-improving agent can be employed as a medium for improving a ratio of CD8-positive cell in a cytotoxic lymphocyte. The above-mentioned medium optionally contains basic components for the cell culture. Here, the ratio-improving agent and the medium for improving the ratio mentioned above can be prepared using the effective ingredient of the present invention in accordance with a known method. The content of the effective ingredient of the present invention and the like in the ratio-improving agent or the medium for improving a ratio of CD8-positive cell mentioned above can be appropriately determined as desired in the same manner as in the case of the above-mentioned agent for expressing IL-2R and the like. In addition, the above-mentioned ratio-improving agent may be directly administered to a living body, whereby the ratio of a cytotoxic lymphocyte in a living body can be improved.

In another embodiment of the present invention, there is provided an agent for improving or maintaining cytotoxic activity in a cytotoxic lymphocyte, characterized in that the agent comprises as an effective ingredient fibronectin, a fragment thereof or a mixture thereof. The improving or maintaining agent comprises the effective ingredient itself and further other optional ingredient, for instance, a medium, a protein, and a cytokine (preferably IL-2) which are suitable for a cell to be activated, and other desired components. Also, the medium containing the above-mentioned improving or maintaining agent can be employed as a medium for improving or maintaining a cytotoxic activity in a cytotoxic lymphocyte. The above-mentioned medium optionally contains basic components for the cell culture. Here, the improving or maintaining agent and the medium for improvement or maintenance mentioned above can be prepared using the effective ingredient of the present invention in accordance with a known method. The content of the effective ingredient of the present invention in the improving or maintaining agent and the medium for improvement or maintenance mentioned above are not particularly limited so long as the desired effects of the present invention are obtained. For instance, the content can be appropriately determined in accordance with the content of the effective ingredient in the medium mentioned above used in the method of the present invention as desired. In addition, the above-mentioned improving or maintaining agent may be directly administered to a living body, whereby the activity of the cytotoxic lymphocyte in a living body can be improved or maintained.

Furthermore, the expression-enhancing agent, the ratio-improving agent and the agent for improving or maintaining a cytotoxic activity mentioned above may be in the form in which the components are immobilized to an appropriate solid phase, for instance, a cell culture equipment such as a petri dish, a flask or a bag (including both of those of an open system and closed system), and a cell culture carrier such as beads, a membrane or a slide glass.

Usually, in the lymphocyte-containing culture obtained by using the method for preparing a cytotoxic lymphocyte as described above, cells other than cytotoxic lymphocyte such as helper T cell are admixed therein. However, since lymphocytes having a cytotoxic activity are contained in a large amount in the lymphocyte-containing culture obtained by the present invention, the cells in the culture can be harvested from the culture by centrifugation or the like, and directly used as a cytotoxic lymphocyte obtained by the method of the present invention. Moreover, if the above-mentioned effective ingredient or the like is immobilized to a cell culture equipment or the like, there is no risk of admixture of the component or the like in the resulting cytotoxic lymphocyte.

In addition, a cell population (or culture) rich in a cytotoxic lymphocyte can be further separated from the culture by a known method, and used as a cytotoxic lymphocyte of the present invention. In other words, the method for preparing a cytotoxic lymphocyte obtained by the method of the present invention can comprise the step of selecting a cell population rich in a cytotoxic lymphocyte from the culture obtained by the method.

The method of selecting a cell population rich in a cytotoxic lymphocyte is not particularly limited. The method is exemplified by, for instance, a method comprising selectively collecting only the desired cell from the culture using a cell culture equipment or carrier to which an antibody against a cell surface antigen expressed on the desired cell surface, for instance, an anti-CD8 antibody, is bound, or a method using a flow cytometer. The above-mentioned carrier is exemplified by magnetic beads or a column. In addition, the cell population rich in the desired cell can be obtained by removing by adsorbing out cells other than the desired cell from the culture. For instance, the helper T cell can be removed from the lymphocyte culture using an antibody against a cell surface antigen expressed on a surface of the helper T cell, for instance, an anti-CD4 antibody. In this step, a flow cytometer can be also used. The cell population rich in the cytotoxic lymphocyte thus obtained has a more potent cytotoxic activity, as compared to that of a cell population collected non-selectively from a culture, so that the cell population can be especially preferably used in the medical field.

Further, the present invention provides a cytotoxic lymphocyte obtained by the method for preparing a cytotoxic lymphocyte of the present invention mentioned above. The lymphocyte, especially CTL, has a high cytotoxic activity, which has a characteristic that there is little lowering of the cytotoxic activity, even when the lymphocyte is subjected to the continuous culture or expansion over a long period of time. In addition, the present invention provides a medicament (therapeutic agent) comprising the lymphocyte as an effective ingredient. Especially, the above-mentioned therapeutic agent comprising the lymphocyte is suitably used in adoptive immunotherapy. In the adoptive immunotherapy, the lymphocyte having a cytotoxic activity suitable for treating a patient is administered to the patient by, for instance, intravenous administration. The therapeutic agent can be prepared by, for instance, blending the lymphocyte prepared by the method of the present invention as an effective ingredient with, for instance, a known organic or inorganic carrier suitable for non-oral administration, an excipient, a stabilizing agent and the like, according to a method known in the pharmaceutical field. Incidentally, various conditions for the therapeutic agent, such as the content of lymphocyte of the present invention in the therapeutic agent and the dose of the therapeutic agent, can be appropriately determined according to the known adoptive immunotherapy.

The method for preparing a cytotoxic lymphocyte of the present invention may further comprise the step of transducing a foreign gene into the lymphocyte. In other words, one embodiment of the present invention provides a method for preparing a cytotoxic lymphocyte, further comprising the step of transducing a foreign gene into a cytotoxic lymphocyte. Here, the term "foreign" refers to those which are foreign to a lymphocyte into which a gene is to be transduced.

By carrying out the method for preparing a cytotoxic lymphocyte of the present invention, especially the method for expanding a cytotoxic lymphocyte, the DNA replication ability of the cultured lymphocyte is enhanced. Therefore, by including the step of transducing a gene in the method for preparing a cytotoxic lymphocyte of the present invention, increase in the gene-transducing method is expected.

Methods of transducing a foreign gene are not particularly limited, and an appropriate method can be selected from a known method for transducing a gene. The step of transducing a gene can be carried out at any given point during the preparation of a cytotoxic lymphocyte. For instance, it is preferable to carry out the step simultaneously with any step of the above-mentioned induction, maintenance and/or expansion of the lymphocyte or after the step, from the viewpoint of working efficiency.

As the above-mentioned method for transducing a gene, any of methods using a viral vector, and methods without using the vector can be employed in the present invention. The details of those methods have been already published in numerous literatures.

The above-mentioned viral vector is not particularly limited, and a known viral vector ordinarily used in the method for transducing a gene, for instance, retroviral vector, lentiviral vector, adenoviral vector, adeno-associated viral vector, simian viral vector, vaccinia viral vector, Sendai viral vector, or the like is used. Especially preferably, as the viral vector, retrovirus, adenovirus, adeno-associated virus or simian virus is used. As the above-mentioned viral vector, those lacking replication ability so that the viral vector cannot self-replicate in an infected cell are preferable.

The retroviral vector is used for the purpose of gene therapy or the like because there can be stably incorporated a foreign gene inserted into the vector in chromosomal DNA in the cell into which the vector is to be transduced. Since the vector has a high infection efficiency to the cell during mitosis and proliferation, the gene transduction is preferably carried out in the method for preparing a cytotoxic lymphocyte, for instance, the step of expansion.

As the method for transducing a gene without using a viral vector, there can be employed, but not particularly limited to, for instance, a method using a carrier such as liposome or ligand-polylysine, calcium phosphate method, electroporation method, particle gun method or the like. In this case, there is transduced a foreign gene incorporated into plasmid DNA or linear DNA.

The foreign gene to be transduced into a cytotoxic lymphocyte in the present invention is not particularly limited, and an arbitrary gene which is desired to be transduced into the above-mentioned cell can be selected. As the gene as described above, besides a gene encoding a protein (for instance, an enzyme, a cytokine, a receptor or the like), for instance, a gene encoding an antisense nucleic acid or a ribozyme can be used. In addition, an appropriate marker gene which is capable of selecting a cell into which a gene is transduced may be transduced simultaneously.

The above-mentioned foreign gene can be, for instance, inserted into a vector, a plasmid or the like, so that the foreign gene is expressed under the control of an appropriate promoter, and used. In addition, in order to achieve an efficient transcription of a gene, there may exist in a vector other regulating element which cooperates with a promoter or a transcription initiation site, for instance, an enhancer sequence or a terminator sequence. In addition, for the purpose of inserting a foreign gene into a chromosome of a lymphocyte in which the gene is transduced by homologous recombination, for instance, a foreign gene may be arranged between flanking sequences comprising nucleotide sequences each having homology to nucleotide sequences located on both sides of the desired target insertion site of the gene in the chromosome. The foreign gene to be transduced may be one that is a naturally occurring or an artificially generated, or may be one in which DNA molecules having different origins from each other are bound by a known means such as ligation. Moreover, the foreign gene may be one having a sequence in which a mutation is introduced into a naturally occurring sequence depending upon its purpose.

According to the method of the present invention, for instance, a gene encoding an enzyme associated with the resistance to a drug used for the treatment of a patient with cancer or the like is transduced into a cytotoxic lymphocyte, thereby giving the lymphocyte a drug resistance. If the cytotoxic lymphocyte as described above is used, adoptive immunotherapy and drug therapy can be combined, and, therefore, higher therapeutic effects can be obtained. The drug resistance gene is exemplified by, for instance, a multidrug resistance gene.

On the other hand, conversely to the above-mentioned embodiment, a gene so as to give a sensitivity against a particular drug is transduced into a cytotoxic lymphocyte, thereby giving sensitivity against the drug. In this case, the lymphocyte after being transplanted to a living body can be removed by administering the drug. The gene for giving sensitivity against a drug is exemplified by, for instance, a thymidine kinase gene.

EXAMPLES

The present invention will be more concretely described by means of the examples, without by no means limiting the scope of the present invention thereto.

Preparation Example 1

Preparation of Fibronectin Fragment (1) Preparation of Fibronectin Fragment

H-271, a fragment derived from human fibronectin, was prepared from *Escherichia coli* HB101/pHD101 (FERM BP-2264) in accordance with the method described in U.S. Pat. No. 5,198,423.

In addition, H-296, CH-271 and CH-296, fragments derived from human fibronectin, were each prepared from a culture obtained by culturing *Escherichia coli* HB101/pHD102 (FERM BP-7420), *Escherichia coli* HB101/pCH101 (FERM BP-2799) or *Escherichia coli* HB101/pCH102 (FERM BP-2800), in accordance with the method described in the above-mentioned gazette.

C-274, a fragment derived from human fibronectin, was prepared from a culture obtained by culturing *Escherichia coli* JM109/pTF7221
(FERM BP-1915) in accordance with the method described in U.S. Pat. No. 5,102,988.

C-CS 1, a fragment derived from human fibronectin, was prepared from a culture obtained by culturing *Escherichia coli* HB101/pCS25 (FERM BP-5723) in accordance with the method described in Japanese Patent Gazette No. 3104178.

CHV-89 and CHV-179, fragments derived from human fibronectin, were each prepared from a culture obtained by culturing *Escherichia coli* HB101/pCHV89 (FERM P-12182) or *Escherichia coli* HB101/pCHV179 (FERM P-12183), in accordance with the method described in Japanese Patent Gazette No. 2729712.

In addition, CHV-90, a fragment derived from human fibronectin, was prepared in accordance with the method described in Japanese Patent Gazette No. 2729712. Concretely, a plasmid pCHV90 was constructed in accordance with the procedures described in the gazette, and thereafter a transformant carrying the plasmid was cultured, and CHV-90 was prepared from the culture.

CHV-181, a fragment derived from human fibronectin, was prepared by constructing the plasmid (pCHV181) comprising a DNA encoding CHV-181 in accordance with the method described in WO 97/18318, thereafter culturing *Escherichia coli* HB101/pCHV181 into which the plasmid had been introduced, and preparing the fragment from the culture in the same manner as that for the above CHV-179.

(2) Preparation of CHV-92

As to pCHV181, a plasmid for expressing the above-mentioned polypeptide CHV-181, there was constructed a plasmid CHV92 having deletion of a region encoding a III-13 region in the region encoding CHV-181. The deletion procedures were performed in accordance with procedures for deleting a III-14 coding region from a plasmid pCHV 179, which are described in Japanese Patent Gazette No. 2729712.

*Escherichia coli* HB101 (*Escherichia coli* HB101/pCHV92) transformed with the above-mentioned plasmid pCHV92 was cultured, and the purification procedures were carried out in accordance with the method of purifying the CHV-89 polypeptide described in Japanese Patent Gazette No. 2729712, to obtain a purified CHV-92 preparation from the resulting culture.

(3) Preparation of H-275-Cys

A plasmid for expressing a polypeptide H-275-Cys was constructed in accordance with the following procedures. Concretely, a plasmid pCH102 was prepared from *Escherichia coli* HB101/pCH102 (FERM BP-2800). PCR was carried out using a primer 12S having the nucleotide sequence shown in SEQ ID NO: 20 of Sequence Listing and a primer 14A having the nucleotide sequence shown in SEQ ID NO: 21 of Sequence Listing with the above plasmid as a template, to give a DNA fragment of about 0.8 kb, encoding a heparin binding polypeptide of fibronectin. The resulting DNA fragment was digested with NcoI and BamHI (both manufactured by Takara Bio Inc.), and thereafter ligated with pTV118N (manufactured by Takara Bio Inc.) digested with NcoI and BamHI, to construct a plasmid pRH1.

A plasmid vector pINIII-ompA$_1$ [Ghrayeb J. et al., *EMBO J.,* 3(10), 2437-2442 (1984)] was digested with BamHI and HincII (manufactured by Takara Bio Inc.) to collect a DNA fragment of about 0.9 kb, containing a lipoprotein terminator region. This fragment was mixed and ligated with the above-mentioned plasmid pRH1 which had been digested with BamHI and HincII, to give a plasmid pRH1-T containing a lac promoter, a DNA fragment encoding a heparin binding polypeptide and a lipoprotein terminator in this order.

The reaction for PCR was carried out by using a primer Cys-A having the nucleotide sequence shown in SEQ ID NO: 22 of Sequence Listing and a primer Cys-S having the nucleotide sequence shown in SEQ ID NO: 23 of Sequence Listing with this plasmid pRH1-T as a template. Thereafter, the collected amplified DNA fragment was digested with NotI (manufactured by Takara Bio Inc.), and the DNA fragment was further self-ligated. A cyclic DNA thus obtained was digested with SpeI and ScaI (manufactured by Takara Bio Inc.) to give a DNA fragment of 2.3 kb, and the resulting fragment was mixed and ligated with a DNA fragment of 2.5 kb, obtained by digesting the plasmid pRH1-T with SpeI and ScaI (manufactured by Takara Bio Inc.), to give a plasmid pRH-Cys. The plasmid encodes a polypeptide H-275-Cys in which four amino acids Met-Ala-Ala-Ser (residues 1-4 of SEQ ID NO: 19) were added to an N-terminal side of the above-mentioned H-271, and further Cys was added to a C-terminal of the H-271.

The polypeptide H-275-Cys was prepared by the following method. *Escherichia coli* HB101 transformed with the above-mentioned plasmid pRH-Cys (*Escherichia coli* HB101/pRH-Cys) was cultured overnight at 37° C. in 120 ml of an LB medium. The cells collected from the culture medium were suspended in 40 ml of a buffer for disruption (50 mM Tris-HCl, 1 mM EDTA, 150 mM NaCl, 1 mM DTT, 1 mM PMSF, pH 7.5), and the suspension was subjected to ultrasonic treatment to disrupt the cells. The supernatant obtained by centrifugation was subjected to HiTrap-heparin column (manufactured by Pharmacia) which had been equilibrated with a purifying buffer (50 mM Tris-HCl, pH 7.5). The non-adsorbed fraction in the column was washed with the same buffer, and thereafter the elution was carried out with a purifying buffer having a 0 to 1 M NaCl concentration gradient. The eluate was analyzed by SDS-polyacrylamide gel electrophoresis, and fractions corresponding to a molecular weight of H-275-Cys were collected to give a purified H-275-Cys preparation.

Example 1

Ratio of CD8-Positive Cells in CTLs (1) Isolation and Storage of PBMCs

Blood component was collected from a human normal individual donor having HLA-A2.1, obtained with informed consent. The collected blood component was diluted 2-folds with PBS(−), overlaid on Ficoll-paque (manufactured by Pharmacia), and centrifuged at 500×g for 20 minutes. The peripheral blood mononuclear cells (PBMCs) in the intermediate layer were collected with a pipette, and washed. The collected PBMCs were suspended in a storage solution of 90% FBS (manufactured by Bio Whittaker)/10% DMSO (manufactured by SIGMA), and stored in liquid nitrogen. During CTL induction, these stored PBMCs were rapidly melted in water bath at 37° C., and washed with RPMI 1640 medium (manufactured by Bio Whittaker) containing 10 μg/ml Dnase (manufactured by Calbiochem). Thereafter, the number of living cells was calculated by trypan blue staining method, and the cells were subjected to each experiment.

(2) Induction of Anti-Influenza Virus Memory CTLs

The induction of anti-influenza virus memory CTLs was performed by partially modifying the method of Bednarek et al. [*J. Immunology,* 147(12), 4047-4053 (1991)]. Concretely, PBMCs prepared in item (1) of Example 2 were suspended in RPMI 1640 medium (manufactured by Bio Whittaker) containing 5% human AB-type serum, 0.1 mM nonessential amino acids, 1 mM sodium pyruvate, 2 mM L-glutamine (hereinabove being all manufactured by Bio Whittaker), 10 mM HEPES (manufactured by nakalai tesque), 1% streptomycin-penicillin (manufactured by Gibco BRL) (hereinafter simply referred to as “5HRPMI”) so as to have a concentration of 1 to 4×10$^6$ cells/ml. Thereafter, the suspension was put on a 24-well cell culture plate (manufactured by Falcon) in a volume of 1 ml/well, and the cells were incubated in a 5% $CO_2$ wet-type incubator at 37° C. for 1.5 hours, to separate plastic-adherent monocytes. Thereafter, nonadherent cells were collected using RPMI 1640 medium, and stored on ice as responder cells. To separated monocytes was added 0.5 ml each of 5HRPMI containing as an antigen peptide 5 μg/ml epitope peptide derived from influenza virus protein (A2.1-binding peptide derived from the matrix protein of SEQ ID NO: 24 of Sequence Listing) and 1 μg/ml β2 microglobulin (manufactured by Scrips). The mixture was incubated at room temperature for 2 hours, and thereafter the cells were subjected to X-ray irradiation (5500R) to give antigen-presenting cells. The peptide solution was removed by suction from each of the wells, and the wells were washed with RPMI 1640 medium. Thereafter, the responder cells previously stored on ice were aspirated in 5HRPMI so as to have a concentration of 0.5 to 2×10⁶ cells/ml, and the suspension was added to antigen-presenting cells in an amount of 1 ml per well. At this time, each fibronectin fragment (hereinafter referred to as "FNfr") described in Preparation Example 1 was added so as to have a final concentration of 10 μg/ml. A group without addition of FNfr was set as the control. The plate was cultured at 37° C. in the presence of 5% $CO_2$. On the second day from the initiation of the culture, 1 ml of 5HRPMI containing 60 U/ml IL-2 (manufactured by Shionogi & Co., Ltd.) and 10 μg/ml FNfr was added to each well (the control containing only IL-2). Also, on the fifth day, a half of the culture supernatant was removed, and 1 ml each of IL-2- and FNfr-containing medium (the control containing only IL-2), the same as those mentioned above, was added thereto. On the seventh day, the antigen-presenting cells were prepared in the same manner as above, and thereafter the responder cells which had been cultured for one week were suspended in 5HRPMI so as to have a concentration of 0.5 to 2×10⁶ cells/ml. The suspension was added to the antigen-presenting cells prepared in an amount of 1 ml/well each to re-stimulate the cells. At this time, FNfr was added so as to have a final concentration of 10 μg/ml (the control being without addition). On the second day from re-stimulation, 1 ml of 5HRPMI containing 60 U/ml IL-2 and 10 μg/ml FNfr was added to each well (the control containing only IL-2). Also, on the fifth day, a half of the culture supernatant was removed, and 1 ml each of the medium having the same content as that before removal was added thereto. The culture was continued for additional two days, thereby inducing CTLs.

(3) Determination for Cytotoxic Activity of CTLs

The cytotoxic activity of CTLs prepared in item (2) of Example 1 on the fourteenth day after the initiation of induction was evaluated by a determination method for cytotoxic activity using Calcein-AM [R. Lichtenfels et al., *J. Immunological Methods*, 172(2), 227-239 (1994)]. HLA-A2.1-having EBV transformed B-cells (name of cells: 221A2.1), which were cultured overnight together with an epitope peptide or in the absence of the epitope peptide, were suspended in RPMI 1640 medium containing 5% FBS (manufactured by Bio Whittaker) so as to have a concentration of 1×10⁶ cells/ml. Thereafter, Calcein-AM (manufactured by Dotite) was added to the suspension so as to have a final concentration of 25 μM, and the cells were cultured at 37° C. for 1 hour. The cells were washed with a medium not containing Calcein-AM, and thereafter mixed with K562 cells (ATCC CCL-243) in an amount 20 times that of the cells, to give Calcein-labeled target cells. The K562 cells were used for excluding nonspecific cytotoxic activity by NK cells admixed in the responder cells.

The memory CTLs prepared in item (2) of Example 1 were stepwise diluted with 5HRPMI so as to have a concentration of from 1×10⁵ to 9×10⁶ cells/ml as effector cells. Thereafter, each of the dilutions was poured into each well of 96-well cell culture plate in an amount of 100 μl/well each. Thereto were added the Calcein-labeled target cells prepared to have a concentration of 1×10⁵ cells/ml in an amount of 100 μl/well each. The plate containing the above-cell suspension was centrifuged at 400×g for 1 minute, and thereafter incubated in a wet-type $CO_2$ incubator at 37° C. for 4 hours. After 4 hours, 100 μl of the culture supernatant was collected from each well, and the amount of calcein released (fluorescence intensity) into the culture supernatant was determined by using fluorescence plate reader (485 nm/538 nm). The cytotoxic activity of the CTLs was calculated by the following equation 1:

Cytotoxic Activity (%)=[(Found Value in Each Well−Minimum Released Amount)/(Maximum Released Amount−Minimum Released Amount)]×100    Equation 1:

In the above equation, the minimum released amount is the amount of calcein released in the well containing only target cells and K562 cells, showing the amount of calcein naturally released from the target cells. In addition, the maximum released amount refers to the amount of calcein released when the cells are completely disrupted by adding 0.1% of the surfactant Triton X-100 (manufactured by nakalai tesque) to the target cells. As a result, the cytotoxic activity was induced immediately after the induction, but there were hardly any differences in the cytotoxic activity by the presence or absence of the addition of FNfr during the induction.

(4) Determination of Content Ratio of CD8-Positive Cells in Cell Population of CTLs CTLs which were prepared in item (2) of Example 1 in an amount of 2×10⁵ cells were fixed with PBS (manufactured by Nissui) containing 1% paraformaldehyde (manufactured by nakalai tesque), and then washed with PBS. The fixed cells were suspended in 100 μl of PBS containing 1% BSA (manufactured by SIGMA), FITC-labeled mouse IgG1 or FITC-labeled mouse anti-human CD8 antibody (both manufactured by DAKO) was added thereto, and thereafter the mixture was incubated on ice for 30 minutes. After the incubation, the cells were washed with PBS, and suspended again in PBS containing 1% paraformaldehyde. The cells were subjected to flow cytometry using FACS Vantage (manufactured by Becton Dickinson), and the content ratio of the CD8-positive cells was determined. The results are shown in Table 1.

TABLE 1

| Fibronectin Fragment | Content Ratio of CD8-Positive Cells (%) |
|---|---|
| Control (Without Addition of FNfr) | 60.2 |
| CH-296 | 88.8 |
| CH-271 | 65.7 |
| H-271 | 81.4 |
| C-274 | 86.2 |
| H-275-Cys | 79.0 |
| CHV-89 | 70.2 |
| CHV-90 | 77.0 |
| CHV-181 | 73.1 |
| Control (Without Addition of FNfr) | 33.0 |
| H-296 | 40.1 |
| C-CS1 | 41.6 |
| CHV-92 | 44.0 |
| CHV-179 | 37.8 |

As shown in Table 1, in the group with addition of various fibronectin fragments during the CTL induction, the ratio of the CD8-positive cells on the fourteenth day after the initiation of the CTL induction is high, as compared to that of the control without addition of these fibronectin fragments. In other words, it was clarified that the CTLs could be induced with significantly proliferating the CD8-positive cells by the copresence of the fibronectin fragment.

Example 2

Induction of Expression of Interleukin-2 Receptor (1) Induction of Anti-Influenza Virus Memory CTLs The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of FNfr during the induction.

(2) Determination of Ratio of Interleukin-2 Receptor Expression in CTLs

The ratio of interleukin-2 receptor (IL-2R) expression in the CTLs which were prepared in item (1) of Example 2 on the fourteenth day from the initiation of induction was determined according to the method described in item (4) of Example 1. Here, in this procedure, an FITC-labeled mouse anti-human CD8 antibody was changed to an FITC-labeled mouse anti-human IL-2R(CD25) antibody (manufactured by DAKO). The results are shown in Table 2.

TABLE 2

| Fibronectin Fragment | Content Ratio of IL-2R Expression-Positive Cells (%) |
|---|---|
| Control (Without Addition of FNfr) | 29.8 |
| CH-296 | 65.9 |
| H-296 | 59.4 |
| H-271 | 54.6 |
| C-274 | 61.5 |
| H-275-Cys | 78.2 |
| CHV-89 | 82.3 |
| CHV-90 | 48.3 |
| CHV-92 | 55.6 |
| CHV-179 | 50.3 |
| CHV-181 | 44.8 |
| Control (Without Addition of FNfr) | 46.9 |
| CH-271 | 60.9 |
| C-CS1 | 72.3 |

As shown in Table 2, in all of CTLs induced with addition of various fibronectin fragments, an increase in the ratio of IL-2R expression in the cell population was observed. In other words, it was clarified that CTLs could be induced with increasing the expression level of IL-2R by carrying out induction in the copresence of the fibronectin fragment.

Example 3

Expansion of CTLs (1) Induction of Anti-Influenza Virus Memory CTLs

The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of FNfr during the induction.

(2) Expansion of CTLs

CTLs prepared in item (1) of Example 3 were washed with 5HRPMI, and then made into a suspension having a concentration of $3 \times 10^4$ cells/ml. On the other hand, allogenic PBMCs not having HLA-A2.1 which were collected in the same manner as in item (1) of Example 1 were subjected to X-ray irradiation (3300R), and the cells were washed with the medium and then made into a suspension having a concentration of 2 to $5 \times 10^6$ cells/mi. These CTLs ($3 \times 10^4$ cells) and allogenic PBMCs (4 to $10 \times 10^6$ cells) were suspended in 10 ml of 5HRPMI, or RPMI 1640 medium (manufactured by Bio Whittaker) containing 10% Hyclone FBS, 0.1 mM nonessential amino acids, 1 mM sodium pyruvate, 2 mM L-glutamine (all manufactured by Bio Whittaker), 10 mM HEPES (manufactured by nakalai tesque) and 1% streptomycin-penicillin (manufactured by Gibco BRL) (hereinafter simply referred to as 10HycloneRPMI), and anti-CD3 antibody (manufactured by Janssen-Kyowa) was further added thereto so as to give a final concentration of 50 ng/ml. The mixture was placed into a flask of 12.5 cm² (manufactured by Falcon), and the cells were cultured in a wet-type $CO_2$ incubator at 37° C. for 14 days. During the culture, FNfr was added so as to have a final concentration of 10 µg/ml which was the same as that added during the CTL induction. Also, FNfr was not added to a control group in which induction was carried out without addition of FNfr. Stimulation by a peptide was not added at all during this culture. On the first day after the initiation of the expansion, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 or 10HycloneRPMI to each flask were carried out every 2 to 3 days. During the culture, FNfr in the same concentration was added to the medium for the group with addition of FNfr. On the fourteenth day after the initiation of the expansion, the cytotoxic activity of CTLs was determined in the same manner as in item (3) of Example 1. The degree in which the cytotoxic activity before the expansion is maintained was calculated as "cytotoxic activity maintenance (%)."

The "cytotoxic activity maintenance (%)" was calculated according to the following equation 2:

Cytotoxic Activity Maintenance (%)=[Cytotoxic Activity (%) After Expansion/CytotoxicActivity (%) Before Expansion]×100  Equation 2:

The determination results are shown in Table 3. In the table, an E/T ratio means a ratio of the number of the effector cells (E) to the number of the target cells (T).

TABLE 3

| Medium | Fibronectin Fragment | Cytotoxic Activity Maintenance (%) E/T Ratio = 3 |
|---|---|---|
| 5HRPMI | Control (Without Addition of FNfr) | 17.3 |
| | CH-271 | 53.5 |
| | H-296 | 49.3 |
| | C-CS1 | 49.3 |
| | CHV-92 | 66.2 |
| 10HycloneRPMI | Control (Without Addition of FNfr) | 48.1 |
| | CH-271 | 250.8 |
| | H-296 | 162.3 |
| | H-271 | 72.2 |
| | C-CS1 | 100.2 |
| | CHV-92 | 157.8 |

TABLE 3-continued

| Medium | Fibronectin Fragment | Cytotoxic Activity Maintenance (%) E/T Ratio = 10 |
|---|---|---|
| 10HycloneRPMI | Control (Without Addition of FNfr) | 46.3 |
| | CHV-89 | 69.0 |
| | CHV-90 | 75.6 |

| Medium | Fibronectin Fragment | Cytotoxic Activity Maintenance (%) E/T Ratio = 3 |
|---|---|---|
| 10HycloneRPMI | Control (Without Addition of FNfr) | 70.4 |
| | CH-296 | 113.5 |
| 10HycloneRPMI | Control (Without Addition of FNfr) | 79.3 |
| | CHV-179 | 190.0 |
| | CHV-181 | 94.5 |

As shown in Table 3, the CTLs of the group with addition of various fibronectin fragments during the induction and the expansion maintained a specific, high cytotoxic activity even after the expansion for 14 days as compared to that of the control without addition of the fibronectin fragment. In other words, it was clarified that the CTLs could be expanded in a state in which a high cytotoxic activity was maintained for a long period of time by carrying out the induction and the expansion in the copresence of the fibronectin fragment.

Example 4

Expression of IL-2R in Cell Population After Expansion of CTLs (1) Induction of Anti-Influenza Virus Memory CTLs
The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of FNfr during the induction.
(2) Determination of Ratio of Interleukin-2 Receptor Expression in Expanded CTLs
The CTLs prepared in item (1) of Example 4 were expanded in the same manner as in item (2) of Example 3. The ratio of IL-2R expression-positive cells was determined for the CTLs after the expansion thus obtained in the same manner as in item (2) of Example 2. The results are shown in Table 4.

TABLE 4

| Fibronectin Fragment | Content Ratio of IL-2R Expression-Positive Cells (%) |
|---|---|
| Control (Without Addition of FNfr) | 19.5 |
| CH-271 | 45.3 |
| H-296 | 47.7 |
| H-271 | 48.3 |
| C-274 | 53.5 |
| C-CS | 39.7 |
| CHV-891 | 28.6 |
| CHV-90 | 60.0 |
| CHV-179 | 53.7 |
| CHV-181 | 50.3 |
| Control (Without Addition of FNfr) | 26.8 |
| CH-296 | 36.1 |
| Control (Without Addition of FNfr) | 18.4 |
| H-275-Cys | 56.5 |
| CHV-92 | 59.9 |

As shown in Table 4, in all of the groups with addition of various fibronectin fragments during the induction and the expansion of CTLs, an increase in the ratio of IL-2R expressing cells in the cell population was observed.
In other words, it was clarified that CTLs could be expanded with increasing the expression level of IL-2R by carrying out induction and expansion of CTLs in the presence of the fibronectin fragment.

Example 5

Induction and Expansion of CTLs in the Presence of Fibronectin (1) Induction of Anti-Influenza Virus Memory CTLs
The induction of anti-influenza virus memory CTLs was performed in accordance with the method described in item (2) of Example 1 using the PBMCs isolated and stored in accordance with the method described in item (1) of Example 1. During the induction, fibronectin (manufactured by Calbiochem) was added in place of FNfr so as to have a final concentration of 10 µg/ml (a control being without addition). The cytotoxic activity of CTLs on the fourteenth day after the initiation of the induction was determined in the same manner as in item (3) of Example 1. As a result, there were hardly any differences in the cytotoxic activity by the presence or absence of the addition of fibronectin during the induction.
(2) Determination of Ratio of Interleukin-2 Receptor Expression in CTLs
The ratio of IL-2R expression-positive cells was determined for the CTLs prepared in item (1) of Example 5 in the same manner as in item (2) of Example 2. The results are shown in Table 5.

TABLE 5

| Fibronectin | Content Ratio of IL-2R Expression-Positive Cells (%) |
|---|---|
| Control (Without Addition of Fibronectin) | 34.0 |
| Fibronectin | 64.6 |

As shown in Table 5, in CTLs induced in the presence of fibronectin, an increase in the expression level of IL-2R in the cell population was observed.
In other words, it was clarified that CTLs could be induced with increasing the expression level of IL-2R by carrying out induction of CTLs in the presence of the fibronectin.
(3) Expansion of CTLs
CTLs prepared in item (1) of Example 5 were expanded in the same manner as in item (2) of Example 3. During the expansion, to the group with addition of fibronectin during the induction, fibronectin (manufactured by Calbiochem) was added, so as to have a final concentration of 10 µg/ml (a control without addition). The cytotoxic activity of the CTLs obtained was determined in the same manner as that of item (3) of Example 1, and the degree in which the cytotoxic activity before the expansion is maintained was calculated as "cytotoxic activity maintenance (%)."

The determination results are shown in Table 6.

TABLE 6

| Fibronectin | Cytotoxic Activity Maintenance (%) E/T Ratio = 3 |
|---|---|
| Control (Without Addition of Fibronectin) | 48.1 |
| Fibronectin | 148.9 |

As shown in Table 6, the group in which the induction and the expansion of CTLs were carried out in the presence of fibronectin maintained a high cytotoxic activity. On the other hand, the cytotoxic activity of the control without addition of fibronectin during the induction and the expansion of CTLs was clearly lowered. In other words, it was clarified that CTLs could be expanded in a state in which a specific cytotoxic activity was maintained for a long period of time by adding fibronectin during the induction and the expansion of CTLs.

Example 6

Expansion of CTLs in the Presence of Immobilized Fibronectin (FN) Fragment (1) Immobilization of FN Fragment A fibronectin fragment was immobilized to a culture equipment (vessel) used in the following experiment. Concretely, PBS containing various fibronectin fragments (final concentration: 10 µg/ml) was added in an amount of 1 to 2 ml each to a 24-well cell culture plate and a 12.5 cm² flask. The plate and the flask were subjected to incubation at room temperature for 5 hours, and then stored at 4° C. until use. In addition, the plate and the flask were washed twice with PBS before use.

(2) Induction of Anti-Influenza Virus Memory CTLs

The induction of anti-influenza virus memory CTLs Ls was performed in accordance with the method described in item (2) of Example 1 using the PBMCs isolated and stored in accordance with the method described in item (1) of Example 1. During the induction, a plate immobilized with FNfr was used as a culture equipment (for a control, a plate without immobilization treatment was used). The cytotoxic activity of CTLs after the induction was evaluated in the same manner as in item (3) of Example 1. As a result, there were hardly any differences in the cytotoxic activity by the presence or absence of immobilization of FNfr to the plate used during the induction.

(3) Expansion of CTLs

The CTLs prepared in item (2) of Example 6 were expanded in the same manner as in item (2) of Example 3. During the expansion, flasks with various FNfr's immobilized thereto were used as culture equipments (for a control, a flask without immobilization treatment was used). In addition, 10HycloneRPMI was used as a medium.

The degree in which the cytotoxic activity of CTLs thus expanded was maintained as compared to that before the expansion was evaluated as "cytotoxic activity maintenance (%)."

The determination results are shown in Table 7.

TABLE 7

| Fibronectin Fragment | Cytotoxic Activity Maintenance (%) E/T Ratio = 3 |
|---|---|
| Control (Without Immobilization of FNfr) | 48.1 |
| CH-271 | 95.4 |
| H-296 | 95.0 |
| H-271 | 133.9 |
| C-CS1 | 73.8 |
| H-275-Cys | 137.7 |
| CHV-92 | 92.7 |
| Control (Without Immobilization of FNfr) | 18.7 |
| CH296 | 67.4 |
| C-CS1 | 78.5 |
| CHV-89 | 90.8 |
| CHV-90 | 73.0 |
| CHV-179 | 112.5 |
| CHV-181 | 25.6 |

As shown in Table 7, in the group in which the culture equipment (plate, flask) immobilized with the fibronectin fragment was used during the induction and the expansion of CTLs, the CTLs maintained a specific, high cytotoxic activity even after the expansion. On the other hand, in the control in which the equipment without immobilization with the fibronectin fragment was used during the induction and the expansion of CTLs, the cytotoxic activity was clearly lowered. In other words, it was clarified that the CTLs could be expanded in a state in which a high cytotoxic activity was maintained for a long period of time, comparable to that of the fragment dissolved in the medium, by using the immobilized fibronectin fragment.

Example 7

Content Ratio of CD8-Positive Cells in Cell Population After Expansion of CTLs (1) Induction of Anti-Influenza Virus Memory CTLs The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of FNfr during the induction.

(2) Determination of Content Ratio of CD8-Positive Cells in Expanded CTLs

The CTLs prepared in item (1) of Example 7 were expanded in the same manner as in item (2) of Example 3. The content ratio of CD8-positive cells was determined for the CTLs after the expansion thus obtained in the same manner as in item (4) of Example 1. The results are shown in Table 8.

TABLE 8

| Fibronectin Fragment | Content Ratio of CD8-Positive Cells (%) |
|---|---|
| Control (Without Addition of FNfr) | 40.9 |
| CH-296 | 85.1 |
| CH-271 | 72.1 |
| H-271 | 83.9 |
| Control (Without Addition of FNfr) | 75.4 |

TABLE 8-continued

| Fibronectin Fragment | Content Ratio of CD8-Positive Cells (%) |
|---|---|
| H-296 | 87.2 |
| C-CS1 | 86.5 |
| Control (Without Addition of FNfr) | 33.4 |
| CHV-90 | 72.9 |
| CHV-92 | 51.6 |
| CHV-179 | 57 |
| CHV-181 | 63.5 |

As shown in Table 8, in all of the groups with addition of various fibronectin fragments during the induction and the expansion of CTLs, an increase in the content ratio of CD8-positive cells in the cell population after the expansion was observed.

In other words, it was clarified that CTLs could be expanded with significantly proliferating CD8-positive cells by carrying out induction and expansion of CTLs in the presence of the fibronectin fragment.

Example 8

Induction of Interleukin-2 Receptor Expression in CTLs Induced in the Presence of Immobilized Fibronectin Fragment (1) Immobilization of FN Fragment
A fibronectin fragment was immobilized to a culture equipment (vessel) in the same manner as in item (1) of Example 6.
(2) Induction of Anti-Influenza Virus Memory CTLs
The induction of anti-influenza virus memory CTLs was performed in accordance with the method described in item (2) of Example 1 using the PBMCs isolated and stored in accordance with the method described in item (1) of Example 1. During the induction, a plate immobilized with FNfr prepared in item (1) of Example 8 was used as a culture equipment (for a control, a plate without immobilization treatment was used). The cytotoxic activity of CTLs after the induction was evaluated in the same manner as in item (3) of Example 1. As a result, there were hardly any differences in the cytotoxic activity by the presence or absence of immobilization of FNfr to the plate used during the induction.
(3) Expansion of CTLs
The CTLs prepared in item (2) of Example 8 were expanded in the same manner as in item (2) of Example 3. During the expansion, a flask with FNfr immobilized thereto prepared in item (1) of Example 8 was used as culture equipments (for a control, a flask without immobilization treatment was used). In addition, 10HycloneRPMI was used as a medium.
The ratio of IL-2R expression-positive cells was determined in the same manner as in item (2) of Example 2 for the CTLs before and after the expansion thus obtained.
The determination results are shown in Table 9.

TABLE 9

| Fibronectin Fragment | Content Ratio of IL-2R Expression-Positive Cells Before Expansion (%) | Content Ratio of IL-2R Expression-Positive Cells After Expansion (%) |
|---|---|---|
| Control (Without | 14.4 | 6.8 |

TABLE 9-continued

| Fibronectin Fragment | Content Ratio of IL-2R Expression-Positive Cells Before Expansion (%) | Content Ratio of IL-2R Expression-Positive Cells After Expansion (%) |
|---|---|---|
| Immobilization of FNfr) | | |
| CH-296 | 68.1 | 34.0 |
| CH-271 | 28.3 | 14.7 |
| H-296 | 21.3 | 22.9 |
| C-274 | 30.3 | 20.5 |
| C-CS1 | 56.8 | 34.1 |
| H-275-Cys | 43.6 | 17.2 |
| CHV-89 | 34.6 | 36.8 |
| CHV-90 | 47.3 | 29.1 |
| CHV-92 | 37.2 | 13.0 |
| CHV-179 | 52.3 | 16.3 |
| CHV-181 | 37.4 | 18.3 |

As shown in Table 9 for CTLs, in the group in which the culture equipment (plate, flask) immobilized with the fibronectin fragment was used during the induction and the expansion of CTLs, an increase in a ratio of IL-2R expression was observed as compared to that of the control group in both before and after the expansion. In other words, it was clarified that the CTLs could be expanded with maintaining a high IL-2R expression level, comparable to that of the fragment dissolved in the medium, by using the immobilized fibronectin fragment.

Example 9

Induction of Interleukin-2 Receptor Expression on Surface of CD8 Cells (1) Induction of Anti-Influenza Virus Memory CTLs
The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of FNfr during the induction.
(2) Determination of Ratio of Interleukin-2 Receptor Expression in CTLs
The ratio of interleukin-2 receptor (IL-2R) expression in the CTLs (especially on a surface of CD8 cells) prepared in item (1) of Example 9 on the fourteenth day from initiation of induction was determined according to the method described in item (4) of Example 1. Here, in this procedure, an FITC-labeled mouse anti-human CD8 antibody was used as a primary antibody, and a PE-labeled mouse anti-human IL-2R (CD25) antibody (manufactured by DAKO) was used as a secondary antibody. The results are shown in Table 10.

TABLE 10

| Fibronectin Fragment | Content Ratio of CD8/IL-2R-Double Positive Cell Population (%) |
|---|---|
| Control (Without Addition of FNfr) | 30.7 |
| CH-296 | 56.8 |

As shown in Table 10, in the CTLs induced with addition of various fibronectin fragments, an increase in the ratio of IL-2R expression in the CD8-positive cell population was observed. In other words, it was clarified that CTLs could be induced with increasing the expression level of IL-2R on the surface of CD8 cells by carrying out induction in the copresence of the fibronectin fragment.

Example 10

Content Ratios of CD8-Positive Cells in Cell Population Before and After Expansion of CTLs (Comparison of Fibronectin with Fibronectin Fragment)
(1) Induction of Anti-Influenza Virus Memory CTLs The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of fibronectin and FNfr during the induction.

(2) Determination of Content Ratio of CD8-Positive Cells in Expanded CTLs

The CTLs prepared in item (1) of Example 10 were expanded in the same manner as in item (2) of Example 3. The content ratio of CD8-positive cells was determined for the CTLs before and after the expansion thus obtained in the same manner as in item (4) of Example 1. The results are shown in Table 11.

TABLE 11

|  | Content Ratio of CD8-Positive Cells Before Expansion (%) | Content Ratio of CD8-Positive Cells After Expansion (%) |
| --- | --- | --- |
| Control (Without Addition of FNfr) | 50.5 | 31.2 |
| Fibronectin | 67.3 | 22.5 |
| H-271 | 75.1 | 51.3 |
| CHV-90 | 71.3 | 43.5 |

As shown in Table 11, in all of the groups with addition of various fibronectin fragments during the induction and the expansion of CTLs, an increase in the content ratio of CD8-positive cells in the cell population before the expansion and after the expansion was observed as compared to that of the control group.

In other words, it was clarified that CTLs could be favorably expanded with significantly proliferating CD8-positive cells in both before the expansion and after the expansion by carrying out induction and expansion of CTLs in the presence of the fibronectin fragment as compared to that of fibronectin per se.

Example 11

Induction of IL-2R Expression in Cell Population Before and After Expansion of CTLs (Comparison of Fibronectin with Fibronectin Fragment)
(1) Induction of Anti-Influenza Virus Memory CTLs The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of fibronectin and FNfr during the induction.

(2) Determination of Content Ratio of Il-2R Expression-Positive Cells in Expanded CTLs The CTLs prepared in item (1) of Example 11 were expanded in the same manner as in item (2) of Example 3. The content ratio of IL-2R expression-positive cells was determined for the CTLs before and after the expansion thus obtained in the same manner as in item (2) of Example 2. The results are shown in Table 12.

TABLE 12

|  | Content Ratio of IL-2R Expression-Positive Cells Before Expansion (%) | Content Ratio of IL-2R Expression-Positive Cells After Expansion (%) |
| --- | --- | --- |
| Control (Without Addition of FNfr) | 34.0 | 15.3 |
| Fibronectin | 64.6 | 50.6 |
| H-271 | 76.6 | 76.8 |

As shown in Table 12, in all of the groups with addition of fibronectin fragments during the induction and the expansion of CTLs, an increase in the content ratio of IL-2R expression-positive cells in the cell population before the expansion and after the expansion was observed as compared to that of the control group. This increase ratio was significantly high as compared to the group with the addition of fibronectin.

In other words, it was clarified that CTLs could be favorably expanded with significantly proliferating IL-2R expression-positive cells in both before the expansion and after the expansion by carrying out induction and expansion of CTLs in the presence of the fibronectin fragment as compared to that of fibronectin per se.

Example 12

Expansion of CTLs (Comparison of Fibronectin with Fibronectin Fragment)

(1) Induction of Anti-Influenza Virus Memory CTLs

The induction of anti-influenza virus memory CTLs was carried out in the same manner as in item (2) of Example 1 using the PBMCs which were isolated and stored in the same manner as in item (1) of Example 1. The cytotoxic activity of CTLs on the fourteenth day after the initiation of induction was evaluated in the same manner as in item (3) of Example 1. As a result, there were hardly any differences in the cytotoxic activity by the presence or absence of the addition of fibronectin and FNfr during the induction.

(2) Expansion of CTLs

The CTLs prepared in item (2) of Example 12 were expanded in the same manner as in item (2) of Example 3. In addition, 10HycloneRPMI was used as a medium.

The degree in which the cytotoxic activity of CTLs thus expanded was maintained as compared to that before the expansion was evaluated as "cytotoxic activity maintenance (%)."

The determination results are shown in Table 13.

TABLE 13

| | Cytotoxic Activity Maintenance (%) E/T Ratio = 3 |
|---|---|
| Control (Without Addition of FNfr) | 48.1 |
| Fibronectin | 148.9 |
| CH-271 | 250.8 |

As shown in Table 13, the CTLs of the group with addition of fibronectin fragment during the induction and the expansion maintained a specific, high cytotoxic activity even after the expansion for 14 days as compared to that of the control group without addition of fibronectin fragment. Also, its activity was significantly high as compared to the group with the addition of fibronectin.

In other words, it was clarified that the CTLs could be favorably expanded in a state in which a high cytotoxic activity was maintained for a long period of time by carrying out the induction and the expansion in the copresence of the fibronectin fragment as compared to that in the copresence of the fibronectin per se.

Example 13

Determination of Expansion Fold in Culture System of LAK Cells (Lymphokine-Activated Killer Cells)

(1) Immobilization of Anti-Human CD3 Antibody and FN or FN Fragment

An anti-human CD3 antibody and fibronectin or FN fragment were immobilized to a culture equipment (vessel) used in the following experiment. Concretely, 1 ml (in a case of a 24-well plate) or 2 ml (in a case of 12.5 cm² flask) each of PBS containing an anti-human CD3 antibody (manufactured by Janssen-Kyowa) (final concentration 5 μg/ml) was added to a 24-well cell culture plate or a 12.5 cm² cell culture flask (manufactured by Falcon). During the addition, fibronectin or each of the fibronectin fragments (FNfr) listed in Preparation Example 1 was added to the group with addition of fibronectin or FN fragment so as to have a final concentration of 10 μg/ml (in the case of the 24-well plate) or 25 μg/ml (in the case of the 12.5 cm² flask). As a control, there was also set a group without addition of fibronectin and FNfr.

After these culture equipments were incubated at room temperature for 5 hours, the culture equipments were stored at 4° C. until use. Immediately before use, PBS containing the antibody and FNfr was removed by aspiration from these culture equipments, and thereafter each well was washed twice with PBS, and then once with XVIVO20 medium (manufactured by Bio Whittaker) containing 5% human AB type serum (manufactured by Bio Whittaker) and 1% streptomycin-penicillin (manufactured by GIBCO BRL) (hereinafter simply referred to as 5HXVIVO20), and the culture equipments were subjected to each experiment.

(2) Induction and Culture of LAK Cells

PBMCs which were prepared in item (1) of Example 1 were suspended in 5HXVIVO20 so as to have a concentration of 0.5 to 1×10⁶ cells/ml, and thereafter the suspension was put on a plate immobilized with the anti-human CD3 antibody, or a plate immobilized with the anti-human CD3 antibody and fibronectin or FNfr prepared in item (1) of Example 13 in a volume of 1 ml/well, and IL-2 (manufactured by Shionogi & Co., Ltd.) was added thereto so as to have a final concentration of 1000 U/ml. These plates were subjected to culture at 37° C. in 5% $CO_2$ (zeroth day of culture). On the second and third days from the initiation of culture, 5HXVIVO20 containing 1000 U/ml IL-2 was added in a volume of 1 ml/well. On the fourth day from the initiation of culture, a culture medium properly diluted with 5HXVIVO20 was transferred to a fresh flask to which nothing was immobilized, and IL-2 was added so as to have a final concentration of 500 U/ml. The culture was continued, the culture medium was properly diluted with 5HXVIVO20 every 2 or 3 days in the same manner as the fifth day from the initiation of culture, and IL-2 was added so as to have a final concentration of 300 to 500 U/ml. On the seventh to fifteenth day from the initiation of culture, the number of living cells was counted by trypan blue staining method, and calculated as an expansion fold by comparing the number with the number of cells at the initiation of culture. The results are shown in Table 14.

TABLE 14

| Number of Cultured Days | FN/FN Fragment | Expansion Fold (folds) |
|---|---|---|
| 7 Days | Control (Without Immobilization of FN/FNfr) | ×103 |
| | Fibronectin | ×233 |
| | CH-296 | ×218 |
| | H-296 | ×247 |
| 9 Days | Control (Without Immobilization of FN/FNfr) | ×250 |
| | Fibronectin | ×1190 |
| | CH-296 | ×1286 |
| | H-296 | ×1075 |
| 11 Days | Control (Without Immobilization of FN/FNfr) | ×576 |
| | Fibronectin | ×2304 |
| | CH-296 | ×1728 |
| | H-296 | ×2088 |
| | Control (Without Immobilization of FN/FNfr) | ×660 |
| | C-CS1 | ×1170 |
| 15 Days | Control (Without Immobilization of FN/FNfr) | ×1980 |
| | Fibronectin | ×3348 |
| | CH-296 | ×5364 |
| | Control (Without Immobilization of FN/FNfr) | ×2906 |
| | C-CS1 | ×5117 |

As shown in Table 14, in the group using the culture equipment immobilized with each of the fibronectin fragments at an early stage of the induction of LAK cells, the expansion fold of LAK cells is high as compared to that of the control group. In addition, the expansion fold of the group immobilized with each of the fibronectin fragments was higher than the group using the culture equipment immobilized with fibronectin on the fifteenth day from the initiation of culture. Therefore, it was clarified that in a case where the expansion is carried out over a long period of time, induction and culture of LAK cells are suitably carried out in an even higher expansion fold by the copresence of the fibronectin fragment at an early stage of the induction of LAK cells, as compared to that of fibronectin per se.

Example 14

Determination of Proliferation Ratio in Culture System of LAK Cells (1) Induction and Culture of LAK Cells The induction and the culture of LAK cells were carried out in the same manner as in item (2) of Example 13. The proliferation ratio of the cells from the fourth day to the seventh day from the initiation of culture during this stage was calculated. The results are shown in Table 15.

TABLE 15

| Number of Cells at Initiation of Culture | Fibronectin Fragment | Proliferation Ratio from 4th Day to 7th Day (folds) |
|---|---|---|
| $5 \times 10^5$ cells/ml | Control (Without Immobilization of FNfr) | 2.7 folds |
| | CH-296 | 16.9 folds |
| | Control (Without Immobilization of FNfr) | 33.5 folds |
| | H-296 | 49.5 folds |
| $1 \times 10^6$ cells/ml | Control (Without Immobilization of FNfr) | 6.2 folds |
| | CH-296 | 20.4 folds |
| | Control (Without Immobilization of FNfr) | 23.5 folds |
| | H-296 | 43.5 folds |

As shown in Table 15, in the group using the culture equipment immobilized with each of the fibronectin fragments at an early stage of the induction of LAK cells, the proliferation ratio of LAK cells from the fourth day to the seventh day of the initiation of culture is high as compared to that of the control group. In other words, it was clarified that LAK cells could be induced and cultured at a faster proliferation rate by the copresence of the fibronectin fragment at an early stage of the induction of LAK cells.

Example 15

Determination of Expansion Fold in Culture System of LAK Cells (Induction and Culture of LAK Cells from Low Number of Cells)

(1) Induction and Culture of LAK Cells

The induction and the culture of LAK cells were carried out in the same manner as that of item (2) of Example 13. During this stage, the cell concentration at the initiation of culture was adjusted so as to have a concentration of $2 \times 10^5$ to $1 \times 10^6$ cells/ml ($1 \times 10^5$ to $5 \times 10^5$ cells/cm$^2$). On the fifteenth day from the initiation of culture, the number of living cells was counted by trypan blue staining method, and an expansion fold was calculated as compared to that with the number of cells at the initiation of culture. The results are shown in Table 16.

TABLE 16

| Number of Cells at Initiation of Culture | Fibronectin Fragment | Expansion Fold (folds) |
|---|---|---|
| $2 \times 10^5$ cells/ml ($1 \times 10^5$ cells/cm$^2$) | Control (Without Immobilization of FNfr) | ×48.6 |
| | CH-296 | ×1004 |
| $5 \times 10^5$ cells/ml ($2.5 \times 10^5$ cells/cm$^2$) | Control (Without Immobilization of FNfr) | ×438 |
| | CH-296 | ×1094 |
| $1 \times 10^6$ cells/ml ($5 \times 10^5$ cells/cm$^2$) | Control (Without Immobilization of FNfr) | ×1020 |
| | CH-296 | ×1476 |

As shown in Table 16, in the group using the culture equipment immobilized with each of the fibronectin fragments during the induction of LAK cells, a high expansion fold was obtained on the fifteenth day from the initiation of culture, regardless of the number of cells at the initiation of culture. By contrast, in the control group, the expansion fold on the fifteenth day from the initiation of culture was low when the number of cells at the initiation of culture was low. In other words, it was clarified that LAK cells could be induced and cultured at a high expansion fold by the copresence of the fibronectin fragment during the induction of LAK cells from the low number of cells, regardless of the number of cells at the initiation of culture.

Example 16

Determination of Expansion Fold in Culture System of LAK Cells (Induction and Culture of LAK Cells from Low Number of Cells/Culture Without Procedures of Dilution)

(1) Induction and Culture of LAK Cells

PBMCs which were prepared in item (1) of Example 1 were suspended in 5HXVIVO20 so as to have a concentration of $1 \times 10^4$ cells/ml, and thereafter the suspension was put on a plate immobilized with the anti-human CD3 antibody, or a E-well plate immobilized with the anti-human CD3 antibody and fibronectin or FNfr prepared in the same manner as in item (1) of Example 13 in a volume of 1 ml/well. Four milliliters of 5HXVIVO20 was added thereto ($1 \times 10^3$ cells/cm$^2$), and IL-2 (manufactured by Shionogi & Co., Ltd.) was added thereto so as to have a final concentration of 500 U/ml. These plates were subjected to culture at 37° C. in 5% CO$_2$ (zeroth day of culture). On the second, third and fourth days from the initiation of culture, IL-2 was added so as to have a final concentration of 500 U/ml. The culture was continued, and IL-2 was added every two to three days so as to have a final concentration of 500 U/ml from the seventh day and on from the initiation of culture. During the addition, the dilution procedure of the culture medium was not carried out at all.

On the fifteenth day from the initiation of culture, the number of living cells was counted by trypan blue staining method, and calculated as an expansion fold by comparing the number with the number of cells at the initiation of culture. The results are shown in Table 17.

TABLE 17

| Number of Cultured Days | FN/FN Fragment | Expansion Fold (folds) |
|---|---|---|
| 15 Days | Control (Without Immobilization of FN/FNfr) | ×15 |
| | Fibronectin | ×628 |
| | CH-296 | ×773 |
| | H-296 | ×960 |

As shown in Table 17, in the group using the culture equipment immobilized with each of the fibronectin fragments during the induction of LAK cells from the low number of cells, a high expansion fold was obtained on the fifteenth day from the initiation of culture, without requiring the dilution procedure of the cells during the course of the induction. Also, this expansion fold was high even when compared to the group using the culture equipment immobilized with the fibronectin. By contrast, in the control group, the cells hardly proliferated even on the fifteenth day from the initiation of culture. In other words, it was clarified that LAK cells could be induced and cultured at a high expansion fold by the copresence of the fibronectin or fibronectin fragment, preferably the fibronectin fragment, during the induction of LAK cells from the low number of cells, without requiring the dilution procedure at all.

Example 17

Induction of IL-2R Expression in LAK Cells (1) Induction and Culture of LAK Cells The induction and the culture of LAK cells were carried out in the same manner as that of item (2) of Example 13.

(2) Determination of Ratio of IL-2R Expression in LAK Cells

The ratio of IL-2R expression in the LAK cells which were subjected to induction and culture in item (1) of Example 17 was determined according to the method described in item (2)

of Example 2. The results are shown in Table 18. In the table, the content ratio of IL-2R expression-positive cells (%) is shown as ratio of IL-2R expression (%).

TABLE 18

| Number of Cultured Days | FN/FN Fragment | Ratio of IL-2R Expression (%) |
|---|---|---|
| 4 Days | Control (Without Immobilization of FN/FNfr) | 86.5 |
| | Fibronectin | 97.2 |
| | CH-296 | 97.6 |
| | H-296 | 97.7 |
| | C-CS1 | 94.9 |
| 7 Days | Control (Without Immobilization of FN/FNfr) | 59.3 |
| | Fibronectin | 77.6 |
| | CH-296 | 90.4 |
| | H-296 | 89.1 |
| | C-CS1 | 65.8 |

As shown in Table 18, in the group using the culture equipment immobilized with each of the fibronectin fragments at an early stage of the induction of LAK cells, a high ratio of IL-2R expression was obtained on the surface of LAK cells during the culture. Also, this ratio of IL-2R expression was high even when compared to the group using the culture equipment immobilized with the fibronectin. In other words, it was clarified that LAK cells could be induced and cultured with a ratio of IL-2R expression being favorably higher than that of the fibronectin per se by the copresence of the fibronectin fragment during the induction of LAK cells.

Example 18

Induction of IL-2R Expression in LAK Cells (1) Induction and Culture of LAK Cells
The induction and the culture of LAK cells were carried out in the same manner as that of item (2) of Example 13.
(2) Determination of Ratio of IL-2R Expression in LAK Cells
The ratio of IL-2R expression on the surfaces of CD4 cells and CD8 cells in the LAK cells which were induced and cultured in item (1) of Example 18 on the seventh day was determined according to the method described in item (2) of Example 9. Here, in this procedure, an FITC-labeled mouse anti-human CD4 antibody or an FITC-labeled mouse anti-human CD8 antibody was used as a primary antibody, and a PE-labeled mouse anti-human IL-2R(CD25) antibody was used as a secondary antibody. The results are shown in Table 19.

TABLE 19

| Fibronectin Fragment | Content Ratio of CD4/IL-2R Double Positive Cells (%) | Content Ratio of CD8/IL-2R Double Positive Cells (%) |
|---|---|---|
| Control (Without Immobilization of FN/FNfr) | 20.5 | 49.4 |
| CH-296 | 41.2 | 61.6 |
| C-CS1 | 24.4 | 54.6 |

As shown in Table 19, in the group using the culture equipment immobilized with each of the fibronectin fragments at an early stage of the induction of LAK cells, a high ratio of IL-2R expression could be induced on the surface of LAK cells (both CD4-positive and CD8-positive cells) during the culture. In other words, it was clarified that LAK cells could be induced and cultured with a high ratio of IL-2R expression on the cell surfaces of both CD4-positive and CD8-positive cells by the copresence of the fibronectin fragment during the induction of LAK cells.

Example 19

Content Ratio of CD8-Positive Cells in LAK Cell Population (1) Induction and Culture of LAK Cells
The induction and the culture of LAK cells were carried out in the same manner as that of item (2) of Example 13.
(2) Determination of Content Ratio of CD8-Positive Cell Population in LAK Cells
The content ratio of CD8-positive cells in the LAK cells which were induced and cultured in item (1) of Example 19 on the fifteenth day was determined according to the method described in item (4) of Example 1. The results are shown in Table 20.

TABLE 20

| Fibronectin Fragment | Content Ratio of CD8-Positive Cells (%) |
|---|---|
| Control (Without Immobilization of FN/FNfr) | 42.9 |
| CH-296 | 72.1 |
| H-296 | 76.0 |

As shown in Table 20, in the group using the culture equipment immobilized with each of the fibronectin fragments at an early stage of induction of LAK cells, a high content ratio of CD8-positive cells could be induced in LAK cells during the culture. In other words, it was clarified that LAK cells could be induced and cultured with a high content ratio of CD8-positive cells in LAK cells by the copresence of the fibronectin fragment during the induction of LAK cells.

Example 21

Determination of Expansion Fold in Culture System of LAK Cells (1) Induction and Culture of LAK Cells
PBMCs which were prepared in item (1) of Example 1 were suspended in 5HXVIVO20 so as to have a concentration of 0.5 to $1 \times 10^6$ cells/ml, and thereafter the suspension was put on a plate immobilized with the anti-human CD3 antibody, or a plate immobilized with the anti-human CD3 antibody and FNfr prepared in item (1) of Example 13 in a volume of 1 ml/well, and IL-2 (manufactured by Shionogi & Co., Ltd.) was added thereto so as to have a final concentration of 1000 U/ml. These plates were subjected to culture at 37° C. in 5% $CO_2$ (zeroth day of culture). On the second and third days from the initiation of culture, 5HXVIVO20 containing 1000 U/ml IL-2 was added in a volume of 1 ml/well. On the fourth day from the initiation of culture, a culture medium properly diluted with 5HXVIVO20 was transferred to a fresh flask to which nothing was immobilized, and IL-2 was added so as to have a final concentration of 500 U/ml. On the eighth or ninth day from the initiation of culture, a culture medium properly diluted with 5HXVIVO20 was transferred to a flask immobilized with the anti-human CD3 antibody, or a flask immobilized with the anti-human CD3 antibody and FNfr (provided that the concentration of the anti-human CD3 antibody used in the immobilization was 0.5 μg/ml) prepared in the same manner as in item (1) of Example 13, and IL-2 was added so as to have a final concentration of 500 U/ml. On the eleventh day or twelfth day from the initiation of culture, a culture medium properly diluted again with 5HXVIVO20 was transferred to a fresh flask to which nothing was immobilized, and IL-2 was added so as to have a final concentration of 500 U/ml. On the fifteenth day from the initiation of culture, the number of living cells was counted by trypan blue staining method, and calculated as an expansion fold by comparing the number with the number of cells at the initiation of culture. The results are shown in Tables 21 and 22. In the table, "Donor" denotes PBMC donors.

TABLE 21

| Donor | Fibronectin Fragment | Stimulation on 0th Day from Initiation of Culture | Stimulation on 8th Day from Initiation of Culture | Expansion Fold (folds) |
|---|---|---|---|---|
| A | Control (Without Immobilization of FNfr) | Anti-CD3 | None | ×80 |
|  |  | Anti-CD3 | Anti-CD3 | ×38 |
|  | CH-296 | Anti-CD3 + CH-296 | None | ×1452 |
|  |  | Anti-CD3 + CH-296 | Anti-CD3 | ×1620 |
|  |  | Anti-CD3 + CH-296 | Anti-CD3 + CH-296 | ×2700 |
| B | Control (Without Immobilization of FNfr) | Anti-CD3 | None | ×710 |
|  |  | Anti-CD3 | Anti-CD3 | ×2363 |
|  | CH-296 | Anti-CD3 + CH-296 | None | ×504 |
|  |  | Anti-CD3 + CH-296 | Anti-CD3 | ×5468 |
|  |  | Anti-CD3 + CH-296 | Anti-CD3 + CH-296 | ×14243 |
| C | Control (Without Immobilization of FNfr) | Anti-CD3 | None | ×1805 |
|  |  | Anti-CD3 | Anti-CD3 | ×4200 |
|  | CH-296 | Anti-CD3 + CH-296 | Anti-CD3 + CH-296 | ×35700 |
|  | H-296 | Anti-CD3 + H-296 | Anti-CD3 + H-296 | ×16950 |

TABLE 22

| Donor | Fibronectin Fragment | Stimulation on 0th Day from Initiation of Culture | Stimulation on 9th Day from Initiation of Culture | Expansion Fold (folds) |
|---|---|---|---|---|
| B | Control (Without Immobilization of FNfr) | Anti-CD3 | None | ×2074 |
|  |  | Anti-CD3 | Anti-CD3 | ×2880 |
|  | CH-296 | Anti-CD3 + CH-296 | Anti-CD3 + CH-296 | ×38400 |
|  | CH-271 | Anti-CD3 + CH-271 | Anti-CD3 + CH-271 | ×12672 |
|  | H-296 | Anti-CD3 + H-296 | Anti-CD3 + H-296 | ×67584 |
|  | H-271 | Anti-CD3 + H-271 | Anti-CD3 + H-271 | ×8755 |
|  | C-274 | Anti-CD3 + C-274 | Anti-CD3 + C-274 | ×8525 |
|  | C-CS1 | Anti-CD3 + C-CS1 | Anti-CD3 + C-CS1 | ×9677 |
|  | CHV-90 | Anti-CD3 + CHV-90 | Anti-CD3 + CHV-90 | ×10138 |
|  | CHV-179 | Anti-CD3 + CHV-179 | Anti-CD3 + CHV-179 | ×8294 |
|  | CHV-181 | Anti-CD3 + CHV-181 | Anti-CD3 + CHV-181 | ×5760 |

As shown in Tables 21 and 22, in the group using the culture equipment in which each of the fibronectin fragments and the anti-CD3 antibody were repeatedly immobilized at an early stage and an intermediate stage of the induction of LAK cells, an expansion fold of LAK cells is high as compared to that of the control group. These expansion ratios were far higher than the expansion fold in the group using the culture equipment in which only the anti-CD3 antibody was repeatedly immobilized at an early stage and an intermediate stage of the induction of LAK cells. In other words, it was clarified that LAK cells could be induced and cultured with a higher expansion fold by stimulation using the fibronectin fragment and the anti-CD3 antibody at an early stage and an intermediate stage of induction of LAK cells.

Example 21

Determination of Proliferation Ratio in Culture System of LAK Cells (1) Induction and Culture of LAK Cells The induction and the culture of LAK cells were carried out in the same manner as that of item (1) of Example 20. The proliferation ratio of the cells from the fourth day to the eighth day from the initiation of culture and the proliferation ratio of the cells from the eleventh day to the fifteenth day from the initiation of culture during the procedures were calculated. The results are shown in Tables 23 and 24.

TABLE 23

| Donor | Fibronectin Fragment | Stimulation on 0th Day from Initiation of Culture | Stimulation on 8th Day from Initiation of Culture | Proliferation Ratio from 11th to 15th Days (folds) |
|---|---|---|---|---|
| A | Control (Without Immobilization of FNfr) | Anti-CD3 | None | 6.7 folds |
|  |  | Anti-CD3 | Anti-CD3 | 8.3 folds |
|  | CH-296 | Anti-CD3 + CH-296 | None | 2.6 folds |
|  |  | Anti-CD3 + CH-296 | Anti-CD3 | 5.5 folds |
|  |  | Anti-CD3 + CH-296 | Anti-CD3 + CH-296 | 11.1 folds |
| B | Control (Without Immobilization of FNfr) | Anti-CD3 | None | 7.4 folds |
|  |  | Anti-CD3 | Anti-CD3 | 17.5 folds |
|  | CH-296 | Anti-CD3 + CH-296 | None | 0.9 folds |
|  |  | Anti-CD3 + CH-296 | Anti-CD3 | 19.8 folds |
|  |  | Anti-CD3 + CH-296 | Anti-CD3 + CH-296 | 60.3 folds |
| C | Control (Without Immobilization of FNfr) | Anti-CD3 | None | 5.2 folds |
|  |  | Anti-CD3 | Anti-CD3 | 22.2 folds |

TABLE 23-continued

| Donor | Fibronectin Fragment | Stimulation on 0th Day from Initiation of Culture | Stimulation on 8th Day from Initiation of Culture | Proliferation Ratio from 11th to 15th Days (folds) |
|---|---|---|---|---|
| | CH-296 | Anti-CD3 + CH-296 | Anti-CD3 + CH-296 | 94.0 folds |
| | H-296 | Anti-CD3 + H-296 | Anti-CD3 + H-296 | 35.0 folds |

TABLE 24

| Donor | Fibronectin Fragment | Stimulation on 0th Day from Initiation of Culture | Stimulation on 9th Day from Initiation of Culture | Proliferation Ratio from 11th to 15th Days (folds) |
|---|---|---|---|---|
| B | Control (Without Immobilization of FNfr) | Anti-CD3 | None | 5.7 folds |
| | | Anti-CD3 | Anti-CD3 | 15.6 folds |
| | CH-296 | Anti-CD3 + CH-296 | Anti-CD3 + CH-296 | 55.6 folds |
| | CH-271 | Anti-CD3 + CH-271 | Anti-CD3 + CH-271 | 25.0 folds |
| | H-296 | Anti-CD3 + H-296 | Anti-CD3 + H-296 | 88.9 folds |
| | H-271 | Anti-CD3 + H-271 | Anti-CD3 + H-271 | 23.8 folds |
| | C-274 | Anti-CD3 + C-274 | Anti-CD3 + C-274 | 61.7 folds |
| | C-CS1 | Anti-CD3 + C-CS1 | Anti-CD3 + C-CS1 | 28.0 folds |
| | CHV-90 | Anti-CD3 + CHV-90 | Anti-CD3 + CHV-90 | 44.0 folds |
| | CHV-179 | Anti-CD3 + CHV-179 | Anti-CD3 + CHV-179 | 32.7 folds |
| | CHV-181 | Anti-CD3 + CHV-181 | Anti-CD3 + CHV-181 | 41.7 folds |

As shown in Tables 23 and 24, in the group using the culture equipment in which each of the fibronectin fragments and the anti-CD3 antibody were repeatedly immobilized at an early stage and an intermediate stage of induction of LAK cells, the proliferation ratio of LAK cells was high in a later stage of the induction as compared to that of the control. These proliferation ratios were far higher than the proliferation ratio of LAK cells in the later stage of the induction in the group using the culture equipment in which only the anti-CD3 antibody was repeatedly immobilized at an early stage and an intermediate stage of induction of LAK cells. In other words, it was clarified that LAK cells could be induced and cultured with a higher proliferation ratio by stimulation using the fibronectin fragment and the anti-CD3 antibody at an early stage and an intermediate stage of induction of LAK cells.

Example 22

Induction of IL-2R Expression in LAK Cells (1) Induction and Culture of LAK Cells The induction and the culture of LAK cells were carried out in the same manner as that of item (1) of Example 20.

(2) Determination of Ratio of IL-2R Expression in LAK Cells

The ratio of IL-2R expression in the LAK cells which were subjected to induction and culture in item (1) of Example 22 on the fifteenth day was determined according to the method described in item (2) of Example 2. The results are shown in Tables 25 and 26. In the tables, the content ratio of the IL-2R expression-positive cells (%) is shown as ratio of IL-2R expression (%).

TABLE 25

| Fibronectin Fragment | Stimulation on 0th Day from Initiation of Culture | Stimulation on 9th Day from Initiation of Culture | Ratio of IL-2R Expression (%) |
|---|---|---|---|
| Control (Without Immobilization of FNfr) | Anti-CD3 | None | 4.8 |
| | Anti-CD3 | Anti-CD3 | 32.6 |
| CH-296 | Anti-CD3 + CH-296 | None | 2.5 |
| | Anti-CD3 + CH-296 | Anti-CD3 | 72.3 |
| | Anti-CD3 + CH-296 | Anti-CD3 + CH-296 | 94.7 |
| H-296 | Anti-CD3 + H-296 | None | 1.4 |
| | Anti-CD3 + H-296 | Anti-CD3 | 50.2 |
| | Anti-CD3 + H-296 | Anti-CD3 + H-296 | 89.6 |

TABLE 26

| Fibronectin Fragment | Stimulation on 0th Day from Initiation of Culture | Stimulation on 9th Day from Initiation of Culture | Ratio of IL-2R Expression (%) |
|---|---|---|---|
| Control (Without Immobilization of FNfr) | Anti-CD3 | None | 4.8 |
| | Anti-CD3 | Anti-CD3 | 18.0 |
| CH-296 | Anti-CD3 + CH-296 | Anti-CD3 + CH-296 | 84.0 |
| CH-271 | Anti-CD3 + CH-271 | Anti-CD3 + CH-271 | 67.1 |
| H-296 | Anti-CD3 + H-296 | Anti-CD3 + H-296 | 79.9 |
| H-271 | Anti-CD3 + H-271 | Anti-CD3 + H-271 | 51.6 |
| C-274 | Anti-CD3 + C-274 | Anti-CD3 + C-274 | 66.4 |
| C-CS1 | Anti-CD3 + C-CS1 | Anti-CD3 + C-CS1 | 72.5 |
| CHV-90 | Anti-CD3 + CHV-90 | Anti-CD3 + CHV-90 | 52.6 |
| CHV-179 | Anti-CD3 + CHV-179 | Anti-CD3 + CHV-179 | 63.4 |
| CHV-181 | Anti-CD3 + CHV-181 | Anti-CD3 + CHV-181 | 68.3 |

As shown in Tables 25 and 26, in the group using the culture equipment in which each of the fibronectin fragments and the anti-CD3 antibody were repeatedly immobilized at an early stage and an intermediate stage of the induction of LAK cells, the ratio of IL-2 expression on the surface of LAK cells on the fifteenth day after the initiation of culture was high as compared to that of the control. These ratios of IL-2R expression were far higher than the ratios of IL-2R expression in the group using the culture equipment in which only the anti-CD3 antibody was repeatedly immobilized at an early stage and an intermediate stage of the induction of LAK cells. In other words, it was clarified that LAK cells could be induced and cultured with a higher ratio of IL-2R expression by stimulation using the fibronectin fragment at an early stage and an intermediate stage of the induction of LAK cells.

Example 23

Determination of Ratio of CD8-Positive Cells in LAK Cells (1) Induction and Culture of LAK Cells The induction and the culture of LAK cells were carried out in the same manner as that of item (1) of Example 20.

(2) Determination of Content Ratio of CD8-Positive Cells in LAK Cell Population

The content ratio of CD8-positive cells in the LAK cell population which were subjected to induction and culture in item (1) of Example 23 on the fifteenth day was determined according to the method described in item (4) of Example 1. The results are shown in Table 27.

TABLE 27

| Fibronectin Fragment | Stimulation on 0th Day from Initiation of Culture | Stimulation on 8th Day from Initiation of Culture | Content Ratio of CD8-Positive Cells (%) |
|---|---|---|---|
| Control (Without Immobilization of FNfr) | Anti-CD3 | None | 42.9 |
|  | Anti-CD3 | Anti-CD3 | 55.2 |
| CH-296 | Anti-CD3 + CH296 | None | 72.1 |
|  | Anti-CD3 + CH296 | Anti-CD3 | 85.2 |
|  | Anti-CD3 + CH296 | Anti-CD3 + CH-296 | 75.9 |
| H-296 | Anti-CD3 + H296 | None | 76.0 |
|  | Anti-CD3 + H296 | Anti-CD3 | 82.0 |
|  | Anti-CD3 + H296 | Anti-CD3 + H296 | 77.1 |

As shown in Table 27, in the group using the culture equipment in which each of the fibronectin fragments and the anti-CD3 antibody were repeatedly immobilized at an early stage and an intermediate stage of the induction of LAK cells, the content ratio of CD8-positive cells in the LAK cell population on the fifteenth day from the initiation of culture was high as compared to that of the control. These content ratios of CD8-positive cells were far higher than the content ratios of CD8-positive cells in the group using the culture equipment in which only the anti-CD3 antibody was repeatedly immobilized at an early stage and an intermediate stage of the induction of LAK cells. In other words, it was clarified that LAK cells could be induced and cultured with a higher content ratio of CD8-positive cells by stimulation using the fibronectin fragment at an early stage and an intermediate stage of the induction of LAK cells.

Sequence Listing Free Text

SEQ ID NO: 1; Partial region of fibronectin named III-8.
SEQ ID NO: 2; Partial region of fibronectin named III-9.
SEQ ID NO: 3; Partial region of fibronectin named III-10.
SEQ ID NO: 4; Partial region of fibronectin named III-12.
SEQ ID NO: 5; Partial region of fibronectin named III-13.
SEQ ID NO: 6; Partial region of fibronectin named III-14.
SEQ ID NO: 7; Partial region of fibronectin named CS-1.
SEQ ID NO: 8; Fibronectin fragment named C-274.
SEQ ID NO: 9; Fibronectin fragment named H-271.
SEQ ID NO: 10; Fibronectin fragment named H-296.
SEQ ID NO: 11; Fibronectin fragment named CH-271.
SEQ ID NO: 12; Fibronectin fragment named CH-296.
SEQ ID NO: 13; Fibronectin fragment named C-CS1.
SEQ ID NO: 14; Fibronectin fragment named CHV-89.
SEQ ID NO: 15; Fibronectin fragment named CHV-90.
SEQ ID NO: 16; Fibronectin fragment named CHV-92.
SEQ ID NO: 17; Fibronectin fragment named CHV-179.
SEQ ID NO: 18; Fibronectin fragment named CHV-181.
SEQ ID NO: 19; Fibronectin fragment named H-275-Cys.
SEQ ID NO: 20; Primer 12S.
SEQ ID NO: 21; Primer 14A.
SEQ ID NO: 22; Primer Cys-A.
SEQ ID NO: 23; Primer Cys-S.
SEQ ID NO: 24; Designed peptide based on matrix protein derived from influenza virus.

Industrial Applicability

According to the process for preparing a cytotoxic lymphocyte of the present invention, there is obtained a cytotoxic lymphocyte in which a high cytotoxic activity is maintained, an expression level of IL-2R is significantly increased, and a ratio of a CD8-positive cell is improved. The lymphocyte is suitably used, for instance, in adoptive immunotherapy. Therefore, there is expected a great contribution of the process of the present invention to the medical field.

The invention claimed is:

1. A method for expanding cytotoxic lymphocytes which comprises:
culturing precursor cells, capable of differentiating to cytotoxic lymphocytes, wherein the precursor cells are selected from the group consisting of peripheral blood mononuclear cells and blood components containing these cells in the presence of at least one recombinant fibronectin fragment together with interleukin-2 and an anti-CD3 antibody,
wherein the recombinant fibronectin fragment is a polypeptide comprising an amino acid sequence selected from the group consisting of SEQ ID NOS: 8 to 19,
wherein the expanded cytotoxic lymphocytes maintain cytotoxic activity longer than cytotoxic lymphocytes expanded in the absence of at least one fibronectin fragment, and
wherein the expanded cytotoxic lymphocytes express more CD8 than cytotoxic lymphocytes expanded in the absence of at least one fibronectin fragment.

2. The method according to claim 1, wherein the expanded cytotoxic lymphocytes highly express an interleukin-2 receptor at a higher level than cytotoxic lymphocytes expanded in the absence of at least one fibronectin fragment.

3. The method according to claim 1, wherein said at least one recombinant fibronectin fragment is immobilized on a solid phase.

4. The method according to claim 3, wherein the solid phase is a cell culture vessel or a cell culture carrier.

5. The method according to claim 1, further comprising transducing a foreign gene into the cytotoxic lymphocytes.

6. The method according to claim 5, wherein the foreign gene is transduced using a retrovirus, adenovirus, adeno-associated virus or simian virus.

7. The method according to claim 1, wherein an expansion ratio of the cytotoxic lympohocytes is high as compared to that of a method for expanding cytotoxic lymphocytes in the absence of at least one recombinant fibronectin fragment.

8. The method according to claim 1, wherein the precursor cells are cultured with the recombinant fibronectin fragment for four days after initiation of culture.

9. A method for increasing the number of CD8 positive cells in a population of cytotoxic lymphocytes, which comprises:
culturing precursor cells, capable of differentiating to cytotoxic lymphocytes, wherein the precursor cells are selected from the group consisting of peripheral blood mononuclear cells and blood components containing these cells in the presence of at least one recombinant fibronectin fragment together with interleukin-2 and an anti-CD3 antibody, thereby increasing the number of CD8-positive cells in the cultured cells,
wherein the recombinant fibronectin fragment is a polypeptide comprising an amino acid sequence selected from the group consisting of SEQ ID NOS: 8 to 19,
wherein the cultured cytotoxic lymphocytes maintain cytotoxic activity longer than cytotoxic lymphocytes expanded in the absence of at least one recombinant fibronectin fragment.

10. The method according to claim 9, wherein the precursor cells are cultured with the recombinant fibronectin fragment for four days after initiation of culture.

* * * * *

SEQUENCE LISTING

```
<160> NUMBER OF SEQ ID NOS: 24

<210> SEQ ID NO 1
<211> LENGTH: 87
<212> TYPE: PRT
<213> ORGANISM: Artificial Sequence
<220> FEATURE:
<223> OTHER INFORMATION: partial region of fibronectin named III-8

<400> SEQUENCE: 1

Pro Thr Asp Leu Arg Phe Thr Asn Ile Gly Pro Asp Thr Met Arg
  1               5                  10                  15

Val Thr Trp Ala Pro Pro Pro Ser Ile Asp Leu Thr Asn Phe Leu
                 20                  25                  30

Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
                 65                  70                  75

His Glu Ser Thr Pro Leu Arg Gly Arg Gln Lys Thr
                 80                  85

<210> SEQ ID NO 2
<211> LENGTH: 90
<212> TYPE: PRT
<213> ORGANISM: Artificial Sequence
```

-continued

```
<220> FEATURE:
<223> OTHER INFORMATION: partial region of fibronectin named III-9

<400> SEQUENCE: 2

Gly Leu Asp Ser Pro Thr Gly Ile Asp Phe Ser Asp Ile Thr Ala
  1               5                  10                  15

Asn Ser Phe Thr Val His Trp Ile Ala Pro Arg Ala Thr Ile Thr
                 20                  25                  30

Gly Tyr Arg Ile Arg His His Pro Glu His Phe Ser Gly Arg Pro
             35                  40                  45

Arg Glu Asp Arg Val Pro His Ser Arg Asn Ser Ile Thr Leu Thr
         50                  55                  60

Asn Leu Thr Pro Gly Thr Glu Tyr Val Val Ser Ile Val Ala Leu
     65                  70                  75

Asn Gly Arg Glu Glu Ser Pro Leu Leu Ile Gly Gln Gln Ser Thr
 80                  85                  90

<210> SEQ ID NO 3
<211> LENGTH: 94
<212> TYPE: PRT
<213> ORGANISM: Artificial Sequence
<220> FEATURE:
<223> OTHER INFORMATION: partial region of fibronectin named III-10

<400> SEQUENCE: 3

Val Ser Asp Val Pro Arg Asp Leu Glu Val Val Ala Ala Thr Pro
  1               5                  10                  15

Thr Ser Leu Leu Ile Ser Trp Asp Ala Pro Ala Val Thr Val Arg
                 20                  25                  30

Tyr Tyr Arg Ile Thr Tyr Gly Glu Thr Gly Gly Asn Ser Pro Val
             35                  40                  45

Gln Glu Phe Thr Val Pro Gly Ser Lys Ser Thr Ala Thr Ile Ser
         50                  55                  60

Gly Leu Lys Pro Gly Val Asp Tyr Thr Ile Thr Val Tyr Ala Val
     65                  70                  75

Thr Gly Arg Gly Asp Ser Pro Ala Ser Ser Lys Pro Ile Ser Ile
 80                  85                  90

Asn Tyr Arg Thr

<210> SEQ ID NO 4
<211> LENGTH: 92
<212> TYPE: PRT
<213> ORGANISM: Artificial Sequence
<220> FEATURE:
<223> OTHER INFORMATION: partial region of fibronectin named III-12

<400> SEQUENCE: 4

Ala Ile Pro Ala Pro Thr Asp Leu Lys Phe Thr Gln Val Thr Pro
  1               5                  10                  15

Thr Ser Leu Ser Ala Gln Trp Thr Pro Pro Asn Val Gln Leu Thr
                 20                  25                  30

Gly Tyr Arg Val Arg Val Thr Pro Lys Glu Lys Thr Gly Pro Met
             35                  40                  45

Lys Glu Ile Asn Leu Ala Pro Asp Ser Ser Ser Val Val Val Ser
         50                  55                  60

Gly Leu Met Val Ala Thr Lys Tyr Glu Val Ser Val Tyr Ala Leu
     65                  70                  75

Lys Asp Thr Leu Thr Ser Arg Pro Ala Gln Gly Val Val Thr Thr
```

```
                    80                  85                  90

Leu Glu

<210> SEQ ID NO 5
<211> LENGTH: 89
<212> TYPE: PRT
<213> ORGANISM: Artificial Sequence
<220> FEATURE:
<223> OTHER INFORMATION: partial region of fibronectin named III-13

<400> SEQUENCE: 5

Asn Val Ser Pro Pro Arg Ala Arg Val Thr Asp Ala Thr Glu
 1               5                  10                  15

Thr Thr Ile Thr Ile Ser Trp Arg Thr Lys Thr Glu Thr Ile Thr
                20                  25                  30

Gly Phe Gln Val Asp Ala Val Pro Ala Asn Gly Gln Thr Pro Ile
            35                  40                  45

Gln Arg Thr Ile Lys Pro Asp Val Arg Ser Tyr Thr Ile Thr Gly
        50                  55                  60

Leu Gln Pro Gly Thr Asp Tyr Lys Ile Tyr Leu Tyr Thr Leu Asn
    65                  70                  75

Asp Asn Ala Arg Ser Ser Pro Val Val Ile Asp Ala Ser Thr
                80                  85

<210> SEQ ID NO 6
<211> LENGTH: 90
<212> TYPE: PRT
<213> ORGANISM: Artificial Sequence
<220> FEATURE:
<223> OTHER INFORMATION: partial region of fibronectin named III-14

<400> SEQUENCE: 6

Ala Ile Asp Ala Pro Ser Asn Leu Arg Phe Leu Ala Thr Thr Pro
 1               5                  10                  15

Asn Ser Leu Leu Val Ser Trp Gln Pro Pro Arg Ala Arg Ile Thr
                20                  25                  30

Gly Tyr Ile Ile Lys Tyr Glu Lys Pro Gly Ser Pro Pro Arg Glu
            35                  40                  45

Val Val Pro Arg Pro Arg Pro Gly Val Thr Glu Ala Thr Ile Thr
        50                  55                  60

Gly Leu Glu Pro Gly Thr Glu Tyr Thr Ile Tyr Val Ile Ala Leu
    65                  70                  75

Lys Asn Asn Gln Lys Ser Glu Pro Leu Ile Gly Arg Lys Lys Thr
                80                  85                  90

<210> SEQ ID NO 7
<211> LENGTH: 25
<212> TYPE: PRT
<213> ORGANISM: Artificial Sequence
<220> FEATURE:
<223> OTHER INFORMATION: partial region of fibronectin named CS-1

<400> SEQUENCE: 7

Asp Glu Leu Pro Gln Leu Val Thr Leu Pro His Pro Asn Leu His
 1               5                  10                  15

Gly Pro Glu Ile Leu Asp Val Pro Ser Thr
                20                  25

<210> SEQ ID NO 8
<211> LENGTH: 274
```

```
<212> TYPE: PRT
<213> ORGANISM: Human
<220> FEATURE:
<223> OTHER INFORMATION: fibronectin fragment named C-274

<400> SEQUENCE: 8
```

Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
             20                  25                  30

Val Arg Tyr Ser Pro Val Lys Asn Glu Glu Asp Val Ala Glu Leu
             35                  40                  45

Ser Ile Ser Pro Ser Asp Asn Ala Val Val Leu Thr Asn Leu Leu
             50                  55                  60

Pro Gly Thr Glu Tyr Val Val Ser Val Ser Ser Val Tyr Glu Gln
             65                  70                  75

His Glu Ser Thr Pro Leu Arg Gly Arg Gln Lys Thr Gly Leu Asp
             80                  85                  90

Ser Pro Thr Gly Ile Asp Phe Ser Asp Ile Thr Ala Asn Ser Phe
             95                  100                 105

Thr Val His Trp Ile Ala Pro Arg Ala Thr Ile Thr Gly Tyr Arg
             110                 115                 120

Ile Arg His His Pro Glu His Phe Ser Gly Arg Pro Arg Glu Asp
             125                 130                 135

Arg Val Pro His Ser Arg Asn Ser Ile Thr Leu Thr Asn Leu Thr
             140                 145                 150

Pro Gly Thr Glu Tyr Val Val Ser Ile Val Ala Leu Asn Gly Arg
             155                 160                 165

Glu Glu Ser Pro Leu Leu Ile Gly Gln Gln Ser Thr Val Ser Asp
             170                 175                 180

Val Pro Arg Asp Leu Glu Val Val Ala Ala Thr Pro Thr Ser Leu
             185                 190                 195

Leu Ile Ser Trp Asp Ala Pro Ala Val Thr Val Arg Tyr Tyr Arg
             200                 205                 210

Ile Thr Tyr Gly Glu Thr Gly Gly Asn Ser Pro Val Gln Glu Phe
             215                 220                 225

Thr Val Pro Gly Ser Lys Ser Thr Ala Thr Ile Ser Gly Leu Lys
             230                 235                 240

Pro Gly Val Asp Tyr Thr Ile Thr Val Tyr Ala Val Thr Gly Arg
             245                 250                 255

Gly Asp Ser Pro Ala Ser Ser Lys Pro Ile Ser Ile Asn Tyr Arg
             260                 265                 270

Thr Glu Ile Asp

```
<210> SEQ ID NO 9
<211> LENGTH: 271
<212> TYPE: PRT
<213> ORGANISM: Human
<220> FEATURE:
<223> OTHER INFORMATION: fibronectin fragment named H-271

<400> SEQUENCE: 9
```

Ala Ile Pro Ala Pro Thr Asp Leu Lys Phe Thr Gln Val Thr Pro
 1               5                  10                  15

Thr Ser Leu Ser Ala Gln Trp Thr Pro Pro Asn Val Gln Leu Thr
             20                  25                  30

-continued

```
Gly Tyr Arg Val Arg Val Thr Pro Lys Glu Lys Thr Gly Pro Met
            35                  40                  45

Lys Glu Ile Asn Leu Ala Pro Asp Ser Ser Val Val Ser
        50                  55                  60

Gly Leu Met Val Ala Thr Lys Tyr Glu Val Ser Val Tyr Ala Leu
            65                  70                  75

Lys Asp Thr Leu Thr Ser Arg Pro Ala Gln Gly Val Val Thr Thr
            80                  85                  90

Leu Glu Asn Val Ser Pro Pro Arg Arg Ala Arg Val Thr Asp Ala
            95                 100                 105

Thr Glu Thr Thr Ile Thr Ile Ser Trp Arg Thr Lys Thr Glu Thr
           110                 115                 120

Ile Thr Gly Phe Gln Val Asp Ala Val Pro Ala Asn Gly Gln Thr
           125                 130                 135

Pro Ile Gln Arg Thr Ile Lys Pro Asp Val Arg Ser Tyr Thr Ile
           140                 145                 150

Thr Gly Leu Gln Pro Gly Thr Asp Tyr Lys Ile Tyr Leu Tyr Thr
           155                 160                 165

Leu Asn Asp Asn Ala Arg Ser Ser Pro Val Val Ile Asp Ala Ser
           170                 175                 180

Thr Ala Ile Asp Ala Pro Ser Asn Leu Arg Phe Leu Ala Thr Thr
           185                 190                 195

Pro Asn Ser Leu Leu Val Ser Trp Gln Pro Pro Arg Ala Arg Ile
           200                 205                 210

Thr Gly Tyr Ile Ile Lys Tyr Glu Lys Pro Gly Ser Pro Pro Arg
           215                 220                 225

Glu Val Val Pro Arg Pro Arg Pro Gly Val Thr Glu Ala Thr Ile
           230                 235                 240

Thr Gly Leu Glu Pro Gly Thr Glu Tyr Thr Ile Tyr Val Ile Ala
           245                 250                 255

Leu Lys Asn Asn Gln Lys Ser Glu Pro Leu Ile Gly Arg Lys Lys
           260                 265                 270

Thr
```

<210> SEQ ID NO 10
<211> LENGTH: 296
<212> TYPE: PRT
<213> ORGANISM: Artificial Sequence
<220> FEATURE:
<223> OTHER INFORMATION: fibronectin fragment named H-296

<400> SEQUENCE: 10

```
Ala Ile Pro Ala Pro Thr Asp Leu Lys Phe Thr Gln Val Thr Pro
 1               5                  10                  15

Thr Ser Leu Ser Ala Gln Trp Thr Pro Pro Asn Val Gln Leu Thr
            20                  25                  30

Gly Tyr Arg Val Arg Val Thr Pro Lys Glu Lys Thr Gly Pro Met
            35                  40                  45

Lys Glu Ile Asn Leu Ala Pro Asp Ser Ser Val Val Ser
        50                  55                  60

Gly Leu Met Val Ala Thr Lys Tyr Glu Val Ser Val Tyr Ala Leu
            65                  70                  75

Lys Asp Thr Leu Thr Ser Arg Pro Ala Gln Gly Val Val Thr Thr
            80                  85                  90

Leu Glu Asn Val Ser Pro Pro Arg Arg Ala Arg Val Thr Asp Ala
```

```
                    95                  100                 105
Thr Glu Thr Thr Ile Thr Ile Ser Trp Arg Thr Lys Thr Glu Thr
                110                 115                 120
Ile Thr Gly Phe Gln Val Asp Ala Val Pro Ala Asn Gly Gln Thr
                125                 130                 135
Pro Ile Gln Arg Thr Ile Lys Pro Asp Val Arg Ser Tyr Thr Ile
                140                 145                 150
Thr Gly Leu Gln Pro Gly Thr Asp Tyr Lys Ile Tyr Leu Tyr Thr
                155                 160                 165
Leu Asn Asp Asn Ala Arg Ser Ser Pro Val Val Ile Asp Ala Ser
                170                 175                 180
Thr Ala Ile Asp Ala Pro Ser Asn Leu Arg Phe Leu Ala Thr Thr
                185                 190                 195
Pro Asn Ser Leu Leu Val Ser Trp Gln Pro Pro Arg Ala Arg Ile
                200                 205                 210
Thr Gly Tyr Ile Ile Lys Tyr Glu Lys Pro Gly Ser Pro Pro Arg
                215                 220                 225
Glu Val Val Pro Arg Pro Arg Pro Gly Val Thr Glu Ala Thr Ile
                230                 235                 240
Thr Gly Leu Glu Pro Gly Thr Glu Tyr Thr Ile Tyr Val Ile Ala
                245                 250                 255
Leu Lys Asn Asn Gln Lys Ser Glu Pro Leu Ile Gly Arg Lys Lys
                260                 265                 270
Thr Asp Glu Leu Pro Gln Leu Val Thr Leu Pro His Pro Asn Leu
                275                 280                 285
His Gly Pro Glu Ile Leu Asp Val Pro Ser Thr
                290                 295

<210> SEQ ID NO 11
<211> LENGTH: 549
<212> TYPE: PRT
<213> ORGANISM: Artificial Sequence
<220> FEATURE:
<223> OTHER INFORMATION: fibronectin fragment named CH-271

<400> SEQUENCE: 11

Pro Thr Asp Leu Arg Phe Thr Asn Ile Gly Pro Asp Thr Met Arg
  1               5                  10                  15
Val Thr Trp Ala Pro Pro Ser Ile Asp Leu Thr Asn Phe Leu
                 20                  25                  30
Val Arg Tyr Ser Pro Val Lys Asn Glu Glu Asp Val Ala Glu Leu
                 35                  40                  45
Ser Ile Ser Pro Ser Asp Asn Ala Val Val Leu Thr Asn Leu Leu
                 50                  55                  60
Pro Gly Thr Glu Tyr Val Val Ser Val Ser Ser Val Tyr Glu Gln
                 65                  70                  75
His Glu Ser Thr Pro Leu Arg Gly Arg Gln Lys Thr Gly Leu Asp
                 80                  85                  90
Ser Pro Thr Gly Ile Asp Phe Ser Asp Ile Thr Ala Asn Ser Phe
                 95                 100                 105
Thr Val His Trp Ile Ala Pro Arg Ala Thr Ile Thr Gly Tyr Arg
                110                 115                 120
Ile Arg His His Pro Glu His Phe Ser Gly Arg Pro Arg Glu Asp
                125                 130                 135
Arg Val Pro His Ser Arg Asn Ser Ile Thr Leu Thr Asn Leu Thr
```

```
                    140                 145                 150
Pro Gly Thr Glu Tyr Val Val Ser Ile Val Ala Leu Asn Gly Arg
                155                 160                 165
Glu Glu Ser Pro Leu Leu Ile Gly Gln Gln Ser Thr Val Ser Asp
                170                 175                 180
Val Pro Arg Asp Leu Glu Val Val Ala Thr Pro Thr Ser Leu
                185                 190                 195
Leu Ile Ser Trp Asp Ala Pro Ala Val Thr Val Arg Tyr Tyr Arg
                200                 205                 210
Ile Thr Tyr Gly Glu Thr Gly Gly Asn Ser Pro Val Gln Glu Phe
                215                 220                 225
Thr Val Pro Gly Ser Lys Ser Thr Ala Thr Ile Ser Gly Leu Lys
                230                 235                 240
Pro Gly Val Asp Tyr Thr Ile Thr Val Tyr Ala Val Thr Gly Arg
                245                 250                 255
Gly Asp Ser Pro Ala Ser Ser Lys Pro Ile Ser Ile Asn Tyr Arg
                260                 265                 270
Thr Glu Ile Asp Lys Pro Ser Met Ala Ile Pro Ala Pro Thr Asp
                275                 280                 285
Leu Lys Phe Thr Gln Val Thr Pro Thr Ser Leu Ser Ala Gln Trp
                290                 295                 300
Thr Pro Pro Asn Val Gln Leu Thr Gly Tyr Arg Val Arg Val Thr
                305                 310                 315
Pro Lys Glu Lys Thr Gly Pro Met Lys Glu Ile Asn Leu Ala Pro
                320                 325                 330
Asp Ser Ser Ser Val Val Val Ser Gly Leu Met Val Ala Thr Lys
                335                 340                 345
Tyr Glu Val Ser Val Tyr Ala Leu Lys Asp Thr Leu Thr Ser Arg
                350                 355                 360
Pro Ala Gln Gly Val Val Thr Thr Leu Glu Asn Val Ser Pro Pro
                365                 370                 375
Arg Arg Ala Arg Val Thr Asp Ala Thr Glu Thr Thr Ile Thr Ile
                380                 385                 390
Ser Trp Arg Thr Lys Thr Glu Thr Ile Thr Gly Phe Gln Val Asp
                395                 400                 405
Ala Val Pro Ala Asn Gly Gln Thr Pro Ile Gln Arg Thr Ile Lys
                410                 415                 420
Pro Asp Val Arg Ser Tyr Thr Ile Thr Gly Leu Gln Pro Gly Thr
                425                 430                 435
Asp Tyr Lys Ile Tyr Leu Tyr Thr Leu Asn Asp Asn Ala Arg Ser
                440                 445                 450
Ser Pro Val Val Ile Asp Ala Ser Thr Ala Ile Asp Ala Pro Ser
                455                 460                 465
Asn Leu Arg Phe Leu Ala Thr Thr Pro Asn Ser Leu Leu Val Ser
                470                 475                 480
Trp Gln Pro Pro Arg Ala Arg Ile Thr Gly Tyr Ile Ile Lys Tyr
                485                 490                 495
Glu Lys Pro Gly Ser Pro Pro Arg Glu Val Val Pro Arg Pro Arg
                500                 505                 510
Pro Gly Val Thr Glu Ala Thr Ile Thr Gly Leu Glu Pro Gly Thr
                515                 520                 525
Glu Tyr Thr Ile Tyr Val Ile Ala Leu Lys Asn Asn Gln Lys Ser
                530                 535                 540
```

Glu Pro Leu Ile Gly Arg Lys Lys Thr
                545

<210> SEQ ID NO 12
<211> LENGTH: 574
<212> TYPE: PRT
<213> ORGANISM: Artificial Sequence
<220> FEATURE:
<223> OTHER INFORMATION: fibronectin fragment named CH-296

<400> SEQUENCE: 12

Pro Thr Asp Leu Arg Phe Thr Asn Ile Gly Pro Asp Thr Met Arg
  1               5                  10                  15

Val Thr Trp Ala Pro Pro Ser Ile Asp Leu Thr Asn Phe Leu
                 20                  25                  30

Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
                 65                  70                  75

His Glu Ser Thr Pro Leu Arg Gly Arg Gln Lys Thr Gly Leu Asp
                 80                  85                  90

Ser Pro Thr Gly Ile Asp Phe Ser Asp Ile Thr Ala Asn Ser Phe
                 95                 100                 105

Thr Val His Trp Ile Ala Pro Arg Ala Thr Ile Thr Gly Tyr Arg
                110                 115                 120

Ile Arg His His Pro Glu His Phe Ser Gly Arg Pro Arg Glu Asp
                125                 130                 135

Arg Val Pro His Ser Arg Asn Ser Ile Thr Leu Thr Asn Leu Thr
                140                 145                 150

Pro Gly Thr Glu Tyr Val Val Ser Ile Val Ala Leu Asn Gly Arg
                155                 160                 165

Glu Glu Ser Pro Leu Leu Ile Gly Gln Gln Ser Thr Val Ser Asp
                170                 175                 180

Val Pro Arg Asp Leu Glu Val Val Ala Ala Thr Pro Thr Ser Leu
                185                 190                 195

Leu Ile Ser Trp Asp Ala Pro Ala Val Thr Val Arg Tyr Tyr Arg
                200                 205                 210

Ile Thr Tyr Gly Glu Thr Gly Gly Asn Ser Pro Val Gln Glu Phe
                215                 220                 225

Thr Val Pro Gly Ser Lys Ser Thr Ala Thr Ile Ser Gly Leu Lys
                230                 235                 240

Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg
                260                 265                 270

Thr Glu Ile Asp Lys Pro Ser Met Ala Ile Pro Ala Pro Thr Asp
                275                 280                 285

Leu Lys Phe Thr Gln Val Thr Pro Thr Ser Leu Ser Ala Gln Trp
                290                 295                 300

Thr Pro Pro Asn Val Gln Leu Thr Gly Tyr Arg Val Arg Val Thr
                305                 310                 315

Pro Lys Glu Lys Thr Gly Pro Met Lys Glu Ile Asn Leu Ala Pro
                320                 325                 330

```
Asp Ser Ser Ser Val Val Ser Gly Leu Met Val Ala Thr Lys
            335                 340                 345

Tyr Glu Val Ser Val Tyr Ala Leu Lys Asp Thr Leu Thr Ser Arg
            350                 355                 360

Pro Ala Gln Gly Val Val Thr Thr Leu Glu Asn Val Ser Pro Pro
            365                 370                 375

Arg Arg Ala Arg Val Thr Asp Ala Thr Glu Thr Thr Ile Thr Ile
            380                 385                 390

Ser Trp Arg Thr Lys Thr Glu Thr Ile Thr Gly Phe Gln Val Asp
            395                 400                 405

Ala Val Pro Ala Asn Gly Gln Thr Pro Ile Gln Arg Thr Ile Lys
            410                 415                 420

Pro Asp Val Arg Ser Tyr Thr Ile Thr Gly Leu Gln Pro Gly Thr
            425                 430                 435

Asp Tyr Lys Ile Tyr Leu Tyr Thr Leu Asn Asp Asn Ala Arg Ser
            440                 445                 450

Ser Pro Val Val Ile Asp Ala Ser Thr Ala Ile Asp Ala Pro Ser
            455                 460                 465

Asn Leu Arg Phe Leu Ala Thr Thr Pro Asn Ser Leu Leu Val Ser
            470                 475                 480

Trp Gln Pro Pro Arg Ala Arg Ile Thr Gly Tyr Ile Ile Lys Tyr
            485                 490                 495

Glu Lys Pro Gly Ser Pro Pro Arg Glu Val Val Pro Arg Pro Arg
            500                 505                 510

Pro Gly Val Thr Glu Ala Thr Ile Thr Gly Leu Glu Pro Gly Thr
            515                 520                 525

Glu Tyr Thr Ile Tyr Val Ile Ala Leu Lys Asn Asn Gln Lys Ser
            530                 535                 540

Glu Pro Leu Ile Gly Arg Lys Lys Thr Asp Glu Leu Pro Gln Leu
            545                 550                 555

Val Thr Leu Pro His Pro Asn Leu His Gly Pro Glu Ile Leu Asp
            560                 565                 570

Val Pro Ser Thr

<210> SEQ ID NO 13
<211> LENGTH: 302
<212> TYPE: PRT
<213> ORGANISM: Artificial Sequence
<220> FEATURE:
<223> OTHER INFORMATION: fibronectin fragment named C-CS1

<400> SEQUENCE: 13

Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
                 20                  25                  30

Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
                 65                  70                  75

His Glu Ser Thr Pro Leu Arg Gly Arg Gln Lys Thr Gly Leu Asp
                 80                  85                  90
```

Ser Pro Thr Gly Ile Asp Phe Ser Asp Ile Thr Ala Asn Ser Phe
            95                  100                 105

Thr Val His Trp Ile Ala Pro Arg Ala Thr Ile Thr Gly Tyr Arg
            110                 115                 120

Ile Arg His His Pro Glu His Phe Ser Gly Arg Pro Arg Glu Asp
            125                 130                 135

Arg Val Pro His Ser Arg Asn Ser Ile Thr Leu Thr Asn Leu Thr
            140                 145                 150

Pro Gly Thr Glu Tyr Val Val Ser Ile Val Ala Leu Asn Gly Arg
            155                 160                 165

Glu Glu Ser Pro Leu Leu Ile Gly Gln Gln Ser Thr Val Ser Asp
            170                 175                 180

Val Pro Arg Asp Leu Glu Val Val Ala Ala Thr Pro Thr Ser Leu
            185                 190                 195

Leu Ile Ser Trp Asp Ala Pro Ala Val Thr Val Arg Tyr Tyr Arg
            200                 205                 210

Ile Thr Tyr Gly Glu Thr Gly Gly Asn Ser Pro Val Gln Glu Phe
            215                 220                 225

Thr Val Pro Gly Ser Lys Ser Thr Ala Thr Ile Ser Gly Leu Lys
            230                 235                 240

Pro Gly Val Asp Tyr Thr Ile Thr Val Tyr Ala Val Thr Gly Arg
            245                 250                 255

Gly Asp Ser Pro Ala Ser Ser Lys Pro Ile Ser Ile Asn Tyr Arg
            260                 265                 270

Thr Glu Ile Asp Lys Pro Ser Asp Glu Leu Pro Gln Leu Val Thr
            275                 280                 285

Leu Pro His Pro Asn Leu His Gly Pro Glu Ile Leu Asp Val Pro
            290                 295                 300

Ser Thr

<210> SEQ ID NO 14
<211> LENGTH: 367
<212> TYPE: PRT
<213> ORGANISM: Artificial Sequence
<220> FEATURE:
<223> OTHER INFORMATION: fibronectin fragment named CHV-89

<400> SEQUENCE: 14

Pro Thr Asp Leu Arg Phe Thr Asn Ile Gly Pro Asp Thr Met Arg
 1               5                  10                  15

Val Thr Trp Ala Pro Pro Pro Ser Ile Asp Leu Thr Asn Phe Leu
            20                  25                  30

Val Arg Tyr Ser Pro Val Lys Asn Glu Glu Asp Val Ala Glu Leu
            35                  40                  45

Ser Ile Ser Pro Ser Asp Asn Ala Val Val Leu Thr Asn Leu Leu
            50                  55                  60

Pro Gly Thr Glu Tyr Val Val Ser Val Ser Ser Val Tyr Glu Gln
            65                  70                  75

His Glu Ser Thr Pro Leu Arg Gly Arg Gln Lys Thr Gly Leu Asp
            80                  85                  90

Ser Pro Thr Gly Ile Asp Phe Ser Asp Ile Thr Ala Asn Ser Phe
            95                  100                 105

Thr Val His Trp Ile Ala Pro Arg Ala Thr Ile Thr Gly Tyr Arg
            110                 115                 120

Ile Arg His His Pro Glu His Phe Ser Gly Arg Pro Arg Glu Asp

```
                    125                 130                 135
Arg Val Pro His Ser Arg Asn Ser Ile Thr Leu Thr Asn Leu Thr
            140                 145                 150

Pro Gly Thr Glu Tyr Val Val Ser Ile Val Ala Leu Asn Gly Arg
            155                 160                 165

Glu Glu Ser Pro Leu Leu Ile Gly Gln Gln Ser Thr Val Ser Asp
            170                 175                 180

Val Pro Arg Asp Leu Glu Val Val Ala Ala Thr Pro Thr Ser Leu
            185                 190                 195

Leu Ile Ser Trp Asp Ala Pro Ala Val Thr Val Arg Tyr Tyr Arg
            200                 205                 210

Ile Thr Tyr Gly Glu Thr Gly Gly Asn Ser Pro Val Gln Glu Phe
            215                 220                 225

Thr Val Pro Gly Ser Lys Ser Thr Ala Thr Ile Ser Gly Leu Lys
            230                 235                 240

Pro Gly Val Asp Tyr Thr Ile Thr Val Tyr Ala Val Thr Gly Arg
            245                 250                 255

Gly Asp Ser Pro Ala Ser Ser Lys Pro Ile Ser Ile Asn Tyr Arg
            260                 265                 270

Thr Glu Ile Asp Lys Pro Ser Met Asn Val Ser Pro Arg Arg
            275                 280                 285

Ala Arg Val Thr Asp Ala Thr Glu Thr Thr Ile Thr Ile Ser Trp
            290                 295                 300

Arg Thr Lys Thr Glu Thr Ile Thr Gly Phe Gln Val Asp Ala Val
            305                 310                 315

Pro Ala Asn Gly Gln Thr Pro Ile Gln Arg Thr Ile Lys Pro Asp
            320                 325                 330

Val Arg Ser Tyr Thr Ile Thr Gly Leu Gln Pro Gly Thr Asp Tyr
            335                 340                 345

Lys Ile Tyr Leu Tyr Thr Leu Asn Asp Asn Ala Arg Ser Ser Pro
            350                 355                 360

Val Val Ile Asp Ala Ser Thr
            365

<210> SEQ ID NO 15
<211> LENGTH: 368
<212> TYPE: PRT
<213> ORGANISM: Artificial Sequence
<220> FEATURE:
<223> OTHER INFORMATION: fibronectin fragment named CHV-90

<400> SEQUENCE: 15

Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
            20                  25                  30

Val Arg Tyr Ser Pro Val Lys Asn Glu Glu Asp Val Ala Glu Leu
            35                  40                  45

Ser Ile Ser Pro Ser Asp Asn Ala Val Val Leu Thr Asn Leu Leu
            50                  55                  60

Pro Gly Thr Glu Tyr Val Val Ser Val Ser Ser Val Tyr Glu Gln
            65                  70                  75

His Glu Ser Thr Pro Leu Arg Gly Arg Gln Lys Thr Gly Leu Asp
            80                  85                  90

Ser Pro Thr Gly Ile Asp Phe Ser Asp Ile Thr Ala Asn Ser Phe
```

```
                    95                  100                 105
Thr Val His Trp Ile Ala Pro Arg Ala Thr Ile Thr Gly Tyr Arg
                110                 115                 120

Ile Arg His His Pro Glu His Phe Ser Gly Arg Pro Arg Glu Asp
                125                 130                 135

Arg Val Pro His Ser Arg Asn Ser Ile Thr Leu Thr Asn Leu Thr
                140                 145                 150

Pro Gly Thr Glu Tyr Val Val Ser Ile Val Ala Leu Asn Gly Arg
                155                 160                 165

Glu Glu Ser Pro Leu Leu Ile Gly Gln Gln Ser Thr Val Ser Asp
                170                 175                 180

Val Pro Arg Asp Leu Glu Val Val Ala Ala Thr Pro Thr Ser Leu
                185                 190                 195

Leu Ile Ser Trp Asp Ala Pro Ala Val Thr Val Arg Tyr Tyr Arg
                200                 205                 210

Ile Thr Tyr Gly Glu Thr Gly Gly Asn Ser Pro Val Gln Glu Phe
                215                 220                 225

Thr Val Pro Gly Ser Lys Ser Thr Ala Thr Ile Ser Gly Leu Lys
                230                 235                 240

Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg
                260                 265                 270

Thr Glu Ile Asp Lys Pro Ser Met Ala Ile Asp Ala Pro Ser Asn
                275                 280                 285

Leu Arg Phe Leu Ala Thr Thr Pro Asn Ser Leu Leu Val Ser Trp
                290                 295                 300

Gln Pro Pro Arg Ala Arg Ile Thr Gly Tyr Ile Ile Lys Tyr Glu
                305                 310                 315

Lys Pro Gly Ser Pro Pro Arg Glu Val Val Pro Arg Pro Arg Pro
                320                 325                 330

Gly Val Thr Glu Ala Thr Ile Thr Gly Leu Glu Pro Gly Thr Glu
                335                 340                 345

Tyr Thr Ile Tyr Val Ile Ala Leu Lys Asn Asn Gln Lys Ser Glu
                350                 355                 360

Pro Leu Ile Gly Arg Lys Lys Thr
                365

<210> SEQ ID NO 16
<211> LENGTH: 370
<212> TYPE: PRT
<213> ORGANISM: Artificial Sequence
<220> FEATURE:
<223> OTHER INFORMATION: fibronectin fragment named CHV-92

<400> SEQUENCE: 16

Pro Thr Asp Leu Arg Phe Thr Asn Ile Gly Pro Asp Thr Met Arg
  1               5                  10                  15

Val Thr Trp Ala Pro Pro Ser Ile Asp Leu Thr Asn Phe Leu
                 20                  25                  30

Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
```

```
                65                  70                  75
His Glu Ser Thr Pro Leu Arg Gly Arg Gln Lys Thr Gly Leu Asp
                80                  85                  90

Ser Pro Thr Gly Ile Asp Phe Ser Asp Ile Thr Ala Asn Ser Phe
                95                 100                 105

Thr Val His Trp Ile Ala Pro Arg Ala Thr Ile Thr Gly Tyr Arg
               110                 115                 120

Ile Arg His His Pro Glu His Phe Ser Gly Arg Pro Arg Glu Asp
               125                 130                 135

Arg Val Pro His Ser Arg Asn Ser Ile Thr Leu Thr Asn Leu Thr
               140                 145                 150

Pro Gly Thr Glu Tyr Val Val Ser Ile Val Ala Leu Asn Gly Arg
               155                 160                 165

Glu Glu Ser Pro Leu Leu Ile Gly Gln Gln Ser Thr Val Ser Asp
               170                 175                 180

Val Pro Arg Asp Leu Glu Val Val Ala Ala Thr Pro Thr Ser Leu
               185                 190                 195

Leu Ile Ser Trp Asp Ala Pro Ala Val Thr Val Arg Tyr Tyr Arg
               200                 205                 210

Ile Thr Tyr Gly Glu Thr Gly Gly Asn Ser Pro Val Gln Glu Phe
               215                 220                 225

Thr Val Pro Gly Ser Lys Ser Thr Ala Thr Ile Ser Gly Leu Lys
               230                 235                 240

Pro Gly Val Asp Tyr Thr Ile Thr Val Tyr Ala Val Thr Gly Arg
               245                 250                 255

Gly Asp Ser Pro Ala Ser Ser Lys Pro Ile Ser Ile Asn Tyr Arg
               260                 265                 270

Thr Glu Ile Asp Lys Pro Ser Met Ala Ile Pro Ala Pro Thr Asp
               275                 280                 285

Leu Lys Phe Thr Gln Val Thr Pro Thr Ser Leu Ser Ala Gln Trp
               290                 295                 300

Thr Pro Pro Asn Val Gln Leu Thr Gly Tyr Arg Val Arg Val Thr
               305                 310                 315

Pro Lys Glu Lys Thr Gly Pro Met Lys Glu Ile Asn Leu Ala Pro
               320                 325                 330

Asp Ser Ser Ser Val Val Ser Gly Leu Met Val Ala Thr Lys
               335                 340                 345

Tyr Glu Val Ser Val Tyr Ala Leu Lys Asp Thr Leu Thr Ser Arg
               350                 355                 360

Pro Ala Gln Gly Val Val Thr Thr Leu Glu
               365                 370

<210> SEQ ID NO 17
<211> LENGTH: 457
<212> TYPE: PRT
<213> ORGANISM: Artificial Sequence
<220> FEATURE:
<223> OTHER INFORMATION: fibronectin fragment named CHV-179

<400> SEQUENCE: 17

Pro Thr Asp Leu Arg Phe Thr Asn Ile Gly Pro Asp Thr Met Arg
  1               5                  10                  15

Val Thr Trp Ala Pro Pro Pro Ser Ile Asp Leu Thr Asn Phe Leu
                 20                  25                  30

Val Arg Tyr Ser Pro Val Lys Asn Glu Glu Asp Val Ala Glu Leu
```

```
                35                  40                  45
Ser Ile Ser Pro Ser Asp Asn Ala Val Val Leu Thr Asn Leu Leu
         50                  55                  60
Pro Gly Thr Glu Tyr Val Ser Val Ser Val Tyr Glu Gln
     65                  70                  75
His Glu Ser Thr Pro Leu Arg Gly Arg Gln Lys Thr Gly Leu Asp
             80                  85                  90
Ser Pro Thr Gly Ile Asp Phe Ser Asp Ile Thr Ala Asn Ser Phe
             95                 100                 105
Thr Val His Trp Ile Ala Pro Arg Ala Thr Ile Thr Gly Tyr Arg
            110                 115                 120
Ile Arg His His Pro Glu His Phe Ser Gly Arg Pro Arg Glu Asp
            125                 130                 135
Arg Val Pro His Ser Arg Asn Ser Ile Thr Leu Thr Asn Leu Thr
            140                 145                 150
Pro Gly Thr Glu Tyr Val Val Ser Ile Val Ala Leu Asn Gly Arg
            155                 160                 165
Glu Glu Ser Pro Leu Leu Ile Gly Gln Gln Ser Thr Val Ser Asp
            170                 175                 180
Val Pro Arg Asp Leu Glu Val Val Ala Ala Thr Pro Thr Ser Leu
            185                 190                 195
Leu Ile Ser Trp Asp Ala Pro Ala Val Thr Val Arg Tyr Tyr Arg
            200                 205                 210
Ile Thr Tyr Gly Glu Thr Gly Gly Asn Ser Pro Val Gln Glu Phe
            215                 220                 225
Thr Val Pro Gly Ser Lys Ser Thr Ala Thr Ile Ser Gly Leu Lys
            230                 235                 240
Pro Gly Val Asp Tyr Thr Ile Thr Val Tyr Ala Val Thr Gly Arg
            245                 250                 255
Gly Asp Ser Pro Ala Ser Ser Lys Pro Ile Ser Ile Asn Tyr Arg
            260                 265                 270
Thr Glu Ile Asp Lys Pro Ser Met Asn Val Ser Pro Pro Arg Arg
            275                 280                 285
Ala Arg Val Thr Asp Ala Thr Glu Thr Thr Ile Thr Ile Ser Trp
            290                 295                 300
Arg Thr Lys Thr Glu Thr Ile Thr Gly Phe Gln Val Asp Ala Val
            305                 310                 315
Pro Ala Asn Gly Gln Thr Pro Ile Gln Arg Thr Ile Lys Pro Asp
            320                 325                 330
Val Arg Ser Tyr Thr Ile Thr Gly Leu Gln Pro Gly Thr Asp Tyr
            335                 340                 345
Lys Ile Tyr Leu Tyr Thr Leu Asn Asp Asn Ala Arg Ser Ser Pro
            350                 355                 360
Val Val Ile Asp Ala Ser Thr Ala Ile Asp Ala Pro Ser Asn Leu
            365                 370                 375
Arg Phe Leu Ala Thr Thr Pro Asn Ser Leu Leu Val Ser Trp Gln
            380                 385                 390
Pro Pro Arg Ala Arg Ile Thr Gly Tyr Ile Ile Lys Tyr Glu Lys
            395                 400                 405
Pro Gly Ser Pro Pro Arg Glu Val Val Pro Arg Pro Arg Pro Gly
            410                 415                 420
Val Thr Glu Ala Thr Ile Thr Gly Leu Glu Pro Gly Thr Glu Tyr
            425                 430                 435
```

```
Thr Ile Tyr Val Ile Ala Leu Lys Asn Asn Gln Lys Ser Glu Pro
                440                 445                 450

Leu Ile Gly Arg Lys Lys Thr
                455

<210> SEQ ID NO 18
<211> LENGTH: 459
<212> TYPE: PRT
<213> ORGANISM: Artificial Sequence
<220> FEATURE:
<223> OTHER INFORMATION: fibronectin fragment named CHV-181

<400> SEQUENCE: 18

Pro Thr Asp Leu Arg Phe Thr Asn Ile Gly Pro Asp Thr Met Arg
  1               5                  10                  15

Val Thr Trp Ala Pro Pro Ser Ile Asp Leu Thr Asn Phe Leu
                 20                  25                  30

Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
                 65                  70                  75

His Glu Ser Thr Pro Leu Arg Gly Arg Gln Lys Thr Gly Leu Asp
                 80                  85                  90

Ser Pro Thr Gly Ile Asp Phe Ser Asp Ile Thr Ala Asn Ser Phe
                 95                 100                 105

Thr Val His Trp Ile Ala Pro Arg Ala Thr Ile Thr Gly Tyr Arg
                110                 115                 120

Ile Arg His His Pro Glu His Phe Ser Gly Arg Pro Arg Glu Asp
                125                 130                 135

Arg Val Pro His Ser Arg Asn Ser Ile Thr Leu Thr Asn Leu Thr
                140                 145                 150

Pro Gly Thr Glu Tyr Val Val Ser Ile Val Ala Leu Asn Gly Arg
                155                 160                 165

Glu Glu Ser Pro Leu Leu Ile Gly Gln Gln Ser Thr Val Ser Asp
                170                 175                 180

Val Pro Arg Asp Leu Glu Val Val Ala Ala Thr Pro Thr Ser Leu
                185                 190                 195

Leu Ile Ser Trp Asp Ala Pro Ala Val Thr Val Arg Tyr Tyr Arg
                200                 205                 210

Ile Thr Tyr Gly Glu Thr Gly Gly Asn Ser Pro Val Gln Glu Phe
                215                 220                 225

Thr Val Pro Gly Ser Lys Ser Thr Ala Thr Ile Ser Gly Leu Lys
                230                 235                 240

Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg
                260                 265                 270

Thr Glu Ile Asp Lys Pro Ser Met Ala Ile Pro Ala Pro Thr Asp
                275                 280                 285

Leu Lys Phe Thr Gln Val Thr Pro Thr Ser Leu Ser Ala Gln Trp
                290                 295                 300

Thr Pro Pro Asn Val Gln Leu Thr Gly Tyr Arg Val Arg Val Thr
                305                 310                 315
```

Pro Lys Glu Lys Thr Gly Pro Met Lys Glu Ile Asn Leu Ala Pro
            320                 325                 330

Asp Ser Ser Ser Val Val Ser Gly Leu Met Val Ala Thr Lys
            335                 340                 345

Tyr Glu Val Ser Val Tyr Ala Leu Lys Asp Thr Leu Thr Ser Arg
            350                 355                 360

Pro Ala Gln Gly Val Val Thr Thr Leu Glu Asn Val Ser Pro Pro
            365                 370                 375

Arg Arg Ala Arg Val Thr Asp Ala Thr Glu Thr Thr Ile Thr Ile
            380                 385                 390

Ser Trp Arg Thr Lys Thr Glu Thr Ile Thr Gly Phe Gln Val Asp
            395                 400                 405

Ala Val Pro Ala Asn Gly Gln Thr Pro Ile Gln Arg Thr Ile Lys
            410                 415                 420

Pro Asp Val Arg Ser Tyr Thr Ile Thr Gly Leu Gln Pro Gly Thr
            425                 430                 435

Asp Tyr Lys Ile Tyr Leu Tyr Thr Leu Asn Asp Asn Ala Arg Ser
            440                 445                 450

Ser Pro Val Val Ile Asp Ala Ser Thr
            455

<210> SEQ ID NO 19
<211> LENGTH: 276
<212> TYPE: PRT
<213> ORGANISM: Artificial Sequence
<220> FEATURE:
<223> OTHER INFORMATION: fibronectin fragment named H-275-Cys

<400> SEQUENCE: 19

Met Ala Ala Ser Ala Ile Pro Ala Pro Thr Asp Leu Lys Phe Thr
 1               5                  10                  15

Gln Val Thr Pro Thr Ser Leu Ser Ala Gln Trp Thr Pro Pro Asn
            20                  25                  30

Val Gln Leu Thr Gly Tyr Arg Val Arg Val Thr Pro Lys Glu Lys
            35                  40                  45

Thr Gly Pro Met Lys Glu Ile Asn Leu Ala Pro Asp Ser Ser Ser
            50                  55                  60

Val Val Val Ser Gly Leu Met Val Ala Thr Lys Tyr Glu Val Ser
            65                  70                  75

Val Tyr Ala Leu Lys Asp Thr Leu Thr Ser Arg Pro Ala Gln Gly
            80                  85                  90

Val Val Thr Thr Leu Glu Asn Val Ser Pro Pro Arg Arg Ala Arg
            95                  100                 105

Val Thr Asp Ala Thr Glu Thr Thr Ile Thr Ile Ser Trp Arg Thr
            110                 115                 120

Lys Thr Glu Thr Ile Thr Gly Phe Gln Val Asp Ala Val Pro Ala
            125                 130                 135

Asn Gly Gln Thr Pro Ile Gln Arg Thr Ile Lys Pro Asp Val Arg
            140                 145                 150

```
Ser Tyr Thr Ile Thr Gly Leu Gln Pro Gly Thr Asp Tyr Lys Ile
            155                 160                 165

Tyr Leu Tyr Thr Leu Asn Asp Asn Ala Arg Ser Ser Pro Val Val
            170                 175                 180

Ile Asp Ala Ser Thr Ala Ile Asp Ala Pro Ser Asn Leu Arg Phe
            185                 190                 195

Leu Ala Thr Thr Pro Asn Ser Leu Leu Val Ser Trp Gln Pro Pro
            200                 205                 210

Arg Ala Arg Ile Thr Gly Tyr Ile Ile Lys Tyr Glu Lys Pro Gly
            215                 220                 225

Ser Pro Pro Arg Glu Val Val Pro Arg Pro Arg Pro Gly Val Thr
            230                 235                 240

Glu Ala Thr Ile Thr Gly Leu Glu Pro Gly Thr Glu Tyr Thr Ile
            245                 250                 255

Tyr Val Ile Ala Leu Lys Asn Asn Gln Lys Ser Glu Pro Leu Ile
            260                 265                 270

Gly Arg Lys Lys Thr Cys
            275
```

<210> SEQ ID NO 20
<211> LENGTH: 38
<212> TYPE: DNA
<213> ORGANISM: Artificial Sequence
<220> FEATURE:
<223> OTHER INFORMATION: synthetic PCR primer 12S

<400> SEQUENCE: 20
aaaccatggc agctagcgct attcctgcac caactgac          38

<210> SEQ ID NO 21
<211> LENGTH: 36
<212> TYPE: DNA
<213> ORGANISM: Artificial Sequence
<220> FEATURE:
<223> OTHER INFORMATION: synthetic PCR primer 14A

<400> SEQUENCE: 21
aaaggatccc taactagtct ttttccttcc aatcag          36

<210> SEQ ID NO 22
<211> LENGTH: 40
<212> TYPE: DNA
<213> ORGANISM: Artificial Sequence
<220> FEATURE:
<223> OTHER INFORMATION: synthetic PCR primer Cys-A

<400> SEQUENCE: 22
aaaagcggcc gctagcgcaa gccatggtct gtttcctgtg          40

<210> SEQ ID NO 23
<211> LENGTH: 41
<212> TYPE: DNA
<213> ORGANISM: Artificial Sequence
<220> FEATURE:
<223> OTHER INFORMATION: synthetic PCR primer Cys-S

<400> SEQUENCE: 23
aaaagcggcc gcactagtgc atagggatcc ggctgagcaa c          41

<210> SEQ ID NO 24
<211> LENGTH: 9
<212> TYPE: PRT

```
<213> ORGANISM: Artificial Sequence
<220> FEATURE:
<223> OTHER INFORMATION: Designed peptide based on matrixprotein derived
      from influenza virus

<400> SEQUENCE: 24

Gly Ile Leu Gly Phe Val Phe Thr Leu
 1               5
```